United States Patent
Weiner et al.

(10) Patent No.: US 12,195,536 B2
(45) Date of Patent: Jan. 14, 2025

(54) DNA MONOCLONAL ANTIBODIES TARGETING CTLA-4 FOR THE TREATMENT AND PREVENTION OF CANCER

(71) Applicant: THE WISTAR INSTITUTE OF ANATOMY AND BIOLOGY, Philadelphia, PA (US)

(72) Inventors: David Weiner, Merion, PA (US); Elizabeth Duperret, Philadelphia, PA (US)

(73) Assignee: The Wistar Institute of Anatomy and Biology, Philadelphia, PA (US)

(*) Notice: Subject to any disclaimer, the term of this patent is extended or adjusted under 35 U.S.C. 154(b) by 648 days.

(21) Appl. No.: 16/753,870

(22) PCT Filed: Oct. 3, 2018

(86) PCT No.: PCT/US2018/054137
§ 371 (c)(1),
(2) Date: Apr. 6, 2020

(87) PCT Pub. No.: WO2019/070834
PCT Pub. Date: Apr. 11, 2019

(65) Prior Publication Data
US 2020/0283525 A1    Sep. 10, 2020

Related U.S. Application Data

(60) Provisional application No. 62/569,470, filed on Oct. 6, 2017.

(51) Int. Cl.
| | | |
|---|---|---|
| C07K 16/28 | (2006.01) |
| A61P 35/00 | (2006.01) |
| C12N 15/63 | (2006.01) |
| A61K 9/00 | (2006.01) |
| A61K 39/00 | (2006.01) |

(52) U.S. Cl.
CPC .......... C07K 16/2818 (2013.01); A61P 35/00 (2018.01); C12N 15/63 (2013.01); A61K 9/0009 (2013.01); A61K 2039/505 (2013.01); C07K 2317/51 (2013.01); C07K 2317/515 (2013.01); C07K 2317/56 (2013.01)

(58) Field of Classification Search
CPC ............................ C12N 15/63; A61K 2039/53
See application file for complete search history.

(56) References Cited

U.S. PATENT DOCUMENTS

| | | | | |
|---|---|---|---|---|
| 7,605,238 B2* | 10/2009 | Korman | ............... | A61P 35/04 |
| | | | | 424/143.1 |
| 2010/0266617 A1* | 10/2010 | Carven | ............. | C07K 16/2818 |
| | | | | 435/69.6 |
| 2011/0293637 A1* | 12/2011 | Hacohen | ............... | A61P 35/02 |
| | | | | 424/277.1 |
| 2017/0114364 A9 | 4/2017 | Allison | | |
| 2019/0241658 A1* | 8/2019 | Frederick | ........... | C07K 16/2818 |

FOREIGN PATENT DOCUMENTS

| | | |
|---|---|---|
| JP | 2009532350 | 9/2009 |
| JP | 2014500004 | 1/2014 |
| JP | 2016533769 A | 11/2016 |
| WO | 2000037504 | 12/1998 |
| WO | 2015035190 | 3/2015 |
| WO | 2015089492 | 6/2015 |
| WO | 2016033555 | 3/2016 |
| WO | 2016089862 | 6/2016 |
| WO | 2017193094 | 11/2017 |

OTHER PUBLICATIONS

Paul, Fundamental Immunology, 3rd Edition, 1993, pp. 292-295.*
Rudikoff et al, Proc. Natl. Acad. Sci. USA, 79(6): 1979-1983, Mar. 1982.*
Colman P. M., Research in Immunology, 145:33-36, 1994.*
Casset et al, Biochemical and Biophysical Research Communications, 2003, vol. 307, pp. 198-205.*
Holm et al, Molecular Immunology, 2007, vol. 44, pp. 1075-1084.*
Duperret Elizabeth K. et al., "Synthetic DNA-Encoded Monoclonal Antibody Delivery of Anti-CTLA-4 Antibodies Induces Tumor Shrinkage In Vivo", Cancer Research, US, vol. 78, No. 22, doi: 10.1158/0008-5472.CAN-18-1429, ISSN 0008-5472, (Oct. 4, 2018), pp. 6363-6370, URL: https://cancerres.aacrjournals.org/content/78/22/6363.full-text.pdf, XP055805417.
He et al., "Remarkably similar CTLA-4 binding properties of therapeutic ipilimumab and tremelimumab antibodies", Oncotarget, (Jan. 1, 2017), vol. 8, doi: 10.18632/oncotarget.18004, pp. 67129-67139, XP055412741.
International Search Report and Written Opinion issued in App. No. PCT/US18/54137, mailing date Feb. 27, 2019, 13 pages.

* cited by examiner

*Primary Examiner* — Mark Halvorson
(74) *Attorney, Agent, or Firm* — Riverside Law LLP

(57) ABSTRACT

Disclosed herein is a composition including a recombinant nucleic acid sequence that encodes an antibody or fragment thereof that targets CTLA-4. The disclosure also provides a method of preventing and/or treating disease, such as cancer, in a subject using the composition of the invention.

15 Claims, 13 Drawing Sheets

Specification includes a Sequence Listing.

A
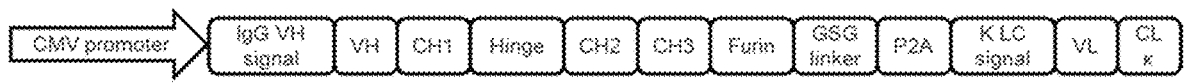
B
9D9 original
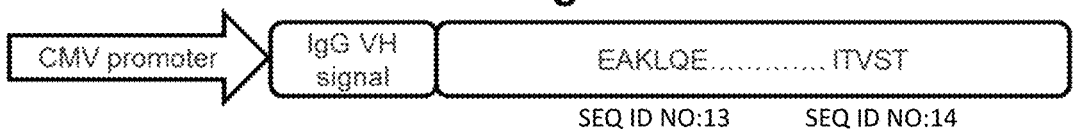
9D9 mod #2
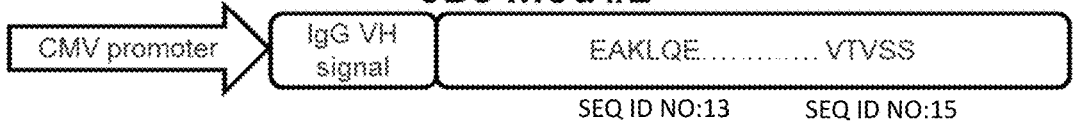
9D9 mod #3
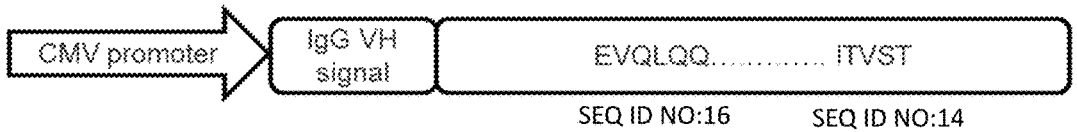
9D9 mod #4
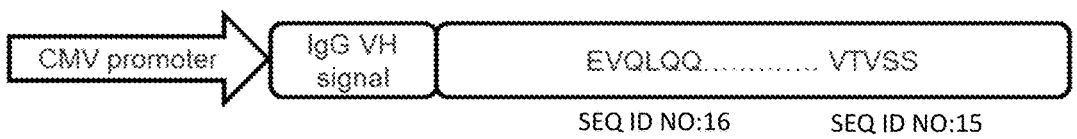
FIG. 1A – 1B

Delivery of α-HUMAN CTLA4 using DNA In vivo expression/binding

Mean trough levels of ipilimumab in patients is 21.8ug/mL at 3mg/kg dose

Synergy of mTERT DNA vaccine + αCTLA-4 DMAb ated by reference herein in their entireties.

DNA MONOCLONAL ANTIBODIES TARGETING CTLA-4 FOR THE TREATMENT AND PREVENTION OF CANCER

CROSS-REFERENCE TO RELATED APPLICATIONS

This application is a U.S. national phase application filed under 35 U.S.C. § 371 claiming priority to International Patent Application No. PCT/US18/54137, filed Oct. 3, 2018, which is entitled to priority under 35 U.S.C. § 119 (e) to U.S. Provisional Application No. 62/569,470, filed Oct. 6, 2017, the contents of each of which are incorpor

TECHNICAL FIELD

The present invention relates to a composition comprising a recombinant nucleic acid sequence for generating one or more synthetic antibodies, including antibodies targeting one or more immune checkpoint molecules (e.g., CTLA-4 and functional fragments thereof), in vivo, and a method of preventing and/or treating cancer and other conditions in a subject by administering said composition.

BACKGROUND

CTLA-4 is an important player in the CD8 T cell exhaustion that takes place in chronic immune conditions such as chronic viral infection and cancer in both experimental models and humans. These known features and function of CTLA-4 make it an appealing target for immune modulation in vaccine and therapeutic settings. Conventional antibody therapies targeting CTLA-4 are very expensive to manufacture, and the elevated cost of these therapies places a significant financial burden on the patient.

Thus, there is a need in the art for improved, cost-effective compositions and methods that target immune checkpoint molecules, such as CTLA-4, for the treatment of cancer and other conditions.

BRIEF DESCRIPTION OF THE DRAWINGS

FIG. 1, comprising FIG. 1A through FIG. 1B, depicts schematic diagrams of the anti-mouse CTLA-4 DMAb design. FIG. 1A depicts a diagram of the orientation of the antibody regions. FIG. 1B depicts a diagram of modifications that were made to the original CTLA-4 DMAb.

FIG. 2, comprising FIG. 2A depicts exemplary data demonstrating the secreted mouse IgG levels for the indicated DMAb from transfected HEK293T cells. FIG. 2B depicts exemplary data demonstrating a western blot analysis of mouse IgG from lysates (left) and supernatants (right). Red bands indicate the ladder, green bands indicate mouse IgG. FIG. 2C depicts exemplary data demonstrating binding of purified 9D9 or supernatants from transfected cells to mouse CTLA-4 protein. $IC_{50}$ is indicated in the figure legend. Individual curves from biological replicates are shown. FIG. 2D depicts exemplary data demonstrating the serum concentration of anti-CTLA-4 mouse IgG from C57Bl/6 mice injected with 100 μg of the indicated DMAb. Error bars indicate mean±SD for in vitro studies, and mean±SEM for in vivo studies. FIGS. 2A and 2C, n=at least 2 biological replicates. FIG. 2D, n=5 mice per group.

FIG. 3, comprising FIG. 3A depicts the tumor study outline for DMAb delivery using prophylactic Sa1N tumor model in A/J mice (top), and serum levels of anti-CTLA-4 mouse IgG from these mice (bottom). 400 μg DMAb was delivered by IM-EP 4 days prior to implantation of tumor cells. FIG. 3B depicts exemplary data demonstrating the tumor volume measurements and survival analysis of the mice described in 3A. FIG. 3C depicts the tumor study outline for DMAb delivery using therapeutic CT26 tumor model in Balb/c mice (top), and serum levels of anti-CTLA-4 mouse IgG from these mice (bottom). 400 μg DMAb was delivered by IM-EP 3 days after implantation of CT26 tumor cells. FIG. 3D depicts exemplary data demonstrating the tumor volume measurements and survival analysis of the mice described in 3C. Error bars indicate mean±SEM. N=10 mice per group. Shown is a representative of two independent experiments.

FIG. 4, comprising FIG. 4A depicts the tumor study outline for antibody treatment. FIG. 4B depicts serum levels of anti-CTLA-4 mouse IgG from these mice. FIG. 4C depicts exemplary data demonstrating the tumor volume measurements of the mice described in 4B. FIG. 4C depicts a survival analysis of the mice described in 4B.

FIG. 6, comprising FIG. 6A depicts the tumor study outline for dMAB delivery. FIG. 6B depicts exemplary data demonstrating the tumor volume measurements of the mice following early administration of the anti-mouse CTLA-4 DMAb. FIG. 6C depicts a survival analysis of the mice following early administration of the anti-mouse CTLA-4 DMAb.

FIG. 7, comprising FIG. 7A through FIG. 7D, depicts exemplary experimental results demonstrating that anti-mouse CTLA-4 DMAb induces T cell infiltration into tumors. FIG. 7A depicts the tumor study outline for dMAB delivery. FIG. 7B depicts immunofluorescent staining of tumors for T-cell infiltration. FIG. 7C depicts a quantification of the numbers of CD8+ and CD3+ T cells per HPF. FIGS. 7D and 7E depict a quantification of the types of TILs present.

FIG. 8, comprising FIG. 8A depicts exemplary data demonstrating the secreted human IgG levels for the indicated DMAb from transfected HEK293T cells. FIG. 8B depicts an exemplary western blot of human IgG from lysates (left) and supernatants (right). FIG. 8C depicts exemplary data demonstrating the serum concentration of human IgG over time in Balb/c mice injected with 400 μg of the indicated DMAb by IM-EP. FIG. 8D depicts exemplary data demonstrating the binding of ipi-DMAb and treme-DMAb purified from mouse serum to human CTLA-4 protein by ELISA. Curves from individual mice are shown. For in vitro experiments, error bars indicate mean±SD. For in vivo experiments, error bars indicate mean±SEM. FIG. 8A, n=2 biological replicates. FIG. 8C, n=5 mice per group. FIG. 8D, n=3 mice per group.

FIG. 10, comprising FIG. 10A depicts exemplary data demonstrating the flow cytometric staining of CD3+CD8-CD25+ human PBMCs for CTLA-4 with the indicated antibodies, with or without PMA/ionomycin stimulation. FIG. 10B depicts the quantification of the staining depicted in FIG. 10A, for 3 individual donors. FIG. 10C depicts an illustration of CTLA-4 blockade bioassay. FIG. 10D depicts results from bioassay described in FIG. 10C. The Relative Luciferase Units (RLU) are graphed relative to the RLU from no antibody control wells. Ipi-DMAb and treme-DMAb were purified from mouse serum. Error bars indicate ±SD. For FIG. 10D, curves indicate 4-parameter nonlinear fit.

DETAILED DESCRIPTION

Figures 2A, 2B, 2C, 2D:
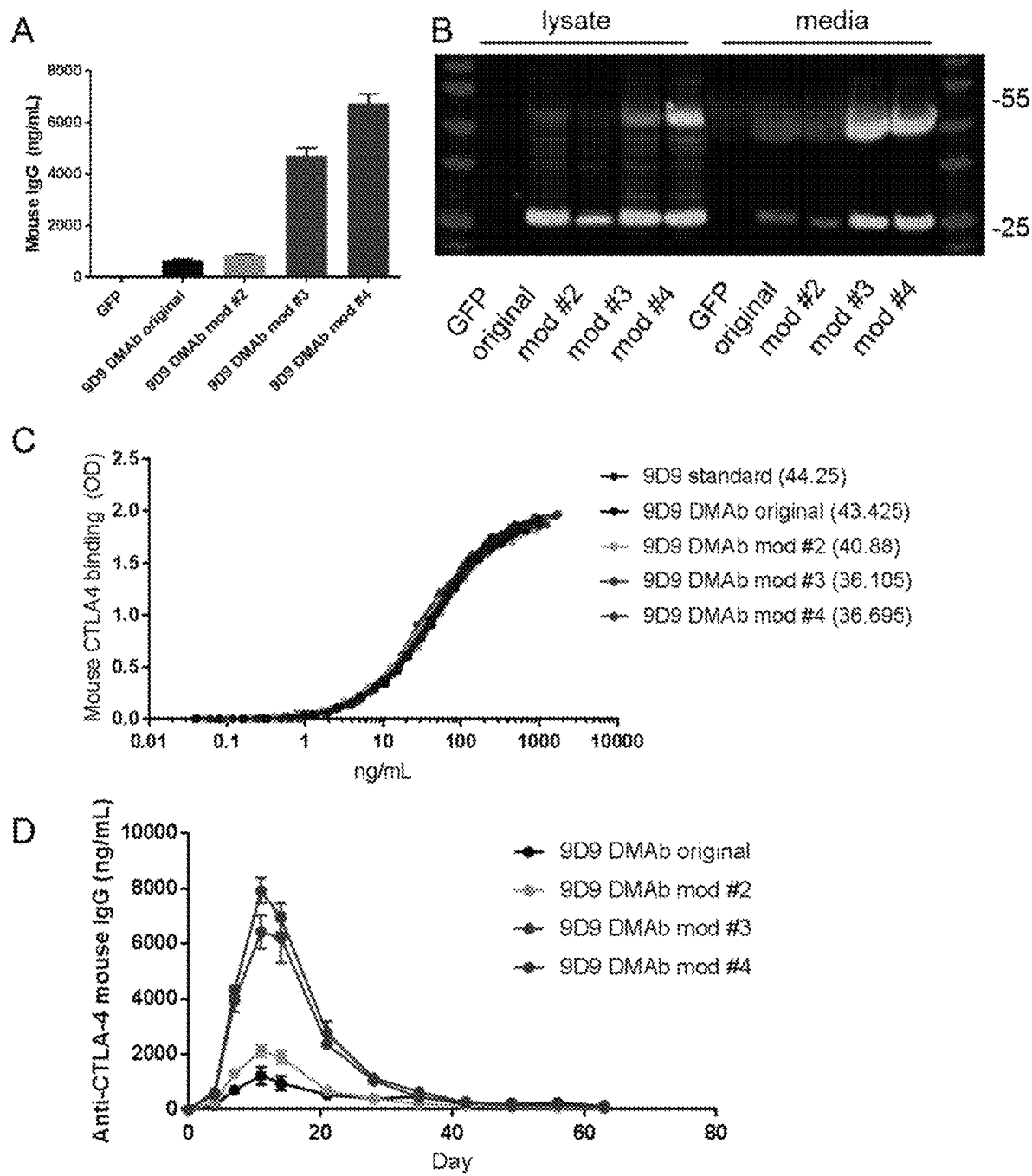
FIG. 2A through FIG. 2D, depicts exemplary experimental results demonstrating the expression and binding of mouse anti-mouse CTLA-4 DMAbs.

The present invention relates to compositions comprising a recombinant nucleic acid sequence encoding an antibody, a fragment thereof, a variant thereof, or a combination thereof. The composition can be administered to a subject in need thereof to facilitate in vivo expression and formation of a synthetic antibody.

In particular, the heavy chain and light chain polypeptides expressed from the recombinant nucleic acid sequences can assemble into the synthetic antibody. The heavy chain polypeptide and the light chain polypeptide can interact with one another such that assembly results in the synthetic antibody being capable of binding the antigen, being more immunogenic as compared to an antibody not assembled as described herein, and being capable of eliciting or inducing an immune response against the antigen.

Additionally, these synthetic antibodies are generated more rapidly in the subject than antibodies that are produced in response to antigen induced immune response. The synthetic antibodies are able to effectively bind and neutralize a range of antigens. The synthetic antibodies are also able to effectively protect against and/or promote survival of disease.

In one aspect, the present invention relates to a composition that can be used to increase or enhance an immune response, i.e., create a more effective immune response, by administering a checkpoint inhibitor, such as an engineered or synthetic antibody directed to CTLA-4 (e.g., engineered MAb in the form of synthetic DNA plasmids; "DMAb").

With respect to engineered MAb in the form of synthetic DNA plasmids, the present invention relates to compositions comprising a recombinant nucleic acid sequence encoding an antibody, a fragment thereof, a variant thereof, or a combination thereof. The composition can be administered to a subject in need thereof to facilitate in vivo expression and formation of a synthetic antibody. In one embodiment, the nucleotide sequence comprises one or more nucleotide sequences described herein. In one embodiment, the nucleotide sequence comprises sequence encoding the polypeptide sequence of SEQ ID NOs: 1, 2, 3, 4, 5, 6, or a variant thereof or a fragment thereof. In one embodiment, the nucleotide sequence comprises an RNA sequence transcribed from a DNA sequence described herein. For example, in one embodiment, the nucleotide sequence comprises an RNA sequence transcribed by a DNA sequence encoding the polypeptide sequence of SEQ ID NOs: 1, 2, 3, 4, 5, 6, or a variant thereof or a fragment thereof.

In one embodiment, the nucleotide sequence encodes an amino acid sequence having at least about 80%, at least about 85%, at least about 90%, or at least about 95% identity over the entire length of the amino acid sequence to an amino acid sequence selected from the group SEQ ID NOs: 1, 2, 3, 4, 5, 6. In one embodiment, the nucleotide sequence encodes a fragment of an amino acid sequence having at least about 80%, at least about 85%, at least about 90%, or at least about 95% identity over the entire length of the amino acid sequence to an amino acid sequence selected from the group SEQ ID NOs: 1, 2, 3, 4, 5, 6.

In one embodiment, the nucleotide sequence has at least about 80%, at least about 85%, at least about 90%, or at least about 95% identity over the entire length of the nucleotide sequence to one or more nucleotide sequences encoding one or more of SEQ ID NOs: 1, 2, 3, 4, 5, 6. In one embodiment, the nucleotide sequence is a fragment of a nucleotide sequence that has at least about 80%, at least about 85%, at least about 90%, or at least about 95% identity over the entire length of the nucleotide sequence to one or more nucleotide sequences encoding one or more of SEQ ID NOs: 1, 2, 3, 4, 5, 6.

In one embodiment, nucleotide sequence has at least about 80% identity over the entire length of at least one nucleotide sequence selected from the group of SEQ ID NOs: 7, 8, 9, 10, 11, and 12.

In some instances, the antibodies of the invention can be administered in combination with a desired composition comprising an antigen, such as TERT, to produce a synergistic effect; whereas, in other instances, the antibodies can be administered separately from the composition comprising the antigen. In some instances the antibodies of the invention comprise a DNA sequence that encodes such antibody, which includes at least the variable regions of the immunoglobulin.

The composition of the present invention can increase the immune response to the antigen of the vaccine in the subject by increasing the CD8+ T cell response, as compared to the vaccine not including checkpoint inhibitors. This increased CD8+ T cell response has cytolytic activity and secretes the cytokine interferon-gamma (IFN-γ).

The compositions provided herein can also include a pharmaceutically acceptable excipient.

Aspects of the invention also include methods for increasing an immune response in a subject in need thereof by administering any of the compositions provided herein to the subject. The methods of increasing an immune response can also include an electroporating step.

1. DEFINITIONS

Unless otherwise defined, all technical and scientific terms used herein have the same meaning as commonly understood by one of ordinary skill in the art. In case of conflict, the present document, including definitions, will control. Exemplary methods and materials are described herein, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Antibody" may mean an antibody of classes IgG, IgM, IgA, IgD or IgE, or fragments, fragments or derivatives thereof, including Fab, F(ab')2, Fd, and single chain antibodies, and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

"Antigen" refers to proteins that have the ability to generate an immune response in a host. An antigen may be recognized and bound by an antibody. An antigen may originate from within the body or from the external environment.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. See for example Chothia et al., (1989) Conformations of immunoglobulin hypervariable regions; Nature 342, p 877-883.

"Antibody fragment" or "fragment of an antibody" as used interchangeably herein refers to a portion of an intact antibody comprising the antigen-binding site or variable region. The portion does not include the constant heavy chain domains (i.e. CH2, CH3, or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"Adjuvant" as used herein means any molecule added to the vaccine described herein to enhance the immunogenicity of the antigen.

"Checkpoint inhibitor" as used herein means inhibitors or molecules that block immune checkpoints as commonly understood in the field of cancer immunotherapy. More commonly the checkpoint inhibitors are antibodies that block these immune checkpoints.

"Coding sequence" or "encoding nucleic acid" as used herein may refer to the nucleic acid (RNA or DNA molecule) that comprise a nucleotide sequence which encodes an antibody as set forth herein. The coding sequence may also comprise a DNA sequence which encodes an RNA sequence. The coding sequence may further include initiation and termination signals operably linked to regulatory elements including a promoter and polyadenylation signal capable of directing expression in the cells of an individual or mammal to whom the nucleic acid is administered. The coding sequence may further include sequences that encode signal peptides.

"Complement" or "complementary" as used herein may mean a nucleic acid may have Watson-Crick (e.g., A-T/U and C-G) or Hoogsteen base pairing between nucleotides or nucleotide analogs of nucleic acid molecules.

"Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein may refer to the use of a transmembrane electric field pulse to induce microscopic pathways (pores) in a biomembrane; their presence allows biomolecules such as plasmids, oligonucleotides, siRNA, drugs, ions, and water to pass from one side of the cellular membrane to the other.

"Endogenous antibody" as used herein may refer to an antibody that is generated in a subject that is administered an effective dose of an antigen for induction of a humoral immune response.

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

"Fragment" may mean a polypeptide fragment of an antibody that is function, i.e., can bind to desired target and have the same intended effect as a full length antibody. A fragment of an antibody may be 100% identical to the full length except missing at least one amino acid from the N and/or C terminal, in each case with or without signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length antibody, excluding any heterologous signal peptide added. The fragment may comprise a fragment of a polypeptide that is 95% or more, 96% or more, 97% or more, 98% or more or 99% or more identical to the antibody and additionally comprise an N terminal methionine or heterologous signal peptide which is not included when calculating percent identity. Fragments may further comprise an N terminal methionine and/or a signal peptide such as an immunoglobulin signal peptide, for example an IgE or IgG signal peptide. The N terminal methionine and/or signal peptide may be linked to a fragment of an antibody.

A fragment of a nucleic acid sequence that encodes an antibody may be 100% identical to the full length except missing at least one nucleotide from the 5' and/or 3' end, in each case with or without sequences encoding signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length coding sequence, excluding any heterologous signal peptide added. The fragment may comprise a fragment that encode a polypeptide that is 95% or more, 96% or more, 97% or more, 98% or more or 99% or more identical to the antibody and additionally optionally comprise sequence encoding an N terminal methionine or heterologous signal peptide which is not included when calculating percent identity. Fragments may further comprise coding sequences for an N terminal methionine and/or a signal peptide such as an immunoglobulin signal peptide, for example an IgE or IgG signal peptide. The coding sequence encoding the N terminal methionine and/or signal peptide may be linked to a fragment of coding sequence.

"Genetic construct" as used herein refers to the DNA or RNA molecules that comprise a nucleotide sequence which encodes a protein, such as an antibody. The genetic construct may also refer to a DNA molecule which transcribes an RNA. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein may mean the activation of a host's immune system, e.g., that of a mammal, in response to the introduction of one or more nucleic acids and/or peptides. The immune response can be in the form of a cellular or humoral response, or both.

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

A "peptide," "protein," or "polypeptide" as used herein can mean a linked sequence of amino acids and can be natural, synthetic, or a modification or combination of natural and synthetic.

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV 40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein may facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc) and a human). In some embodiments, the subject may be a human or a non-human. The subject or patient may be undergoing other forms of treatment.

"Substantially complementary" as used herein may mean that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

"Substantially identical" as used herein may mean that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% identical over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides or amino acids, or with respect to nucleic acids, if the first sequence is substantially complementary to the complement of the second sequence.

"Synthetic antibody" as used herein refers to an antibody that is encoded by the recombinant nucleic acid sequence described herein and is generated in a subject.

"Treatment" or "treating," as used herein can mean protecting of a subject from a disease through means of preventing, suppressing, repressing, or completely eliminating the disease. Preventing the disease involves administering a vaccine of the present invention to a subject prior to onset of the disease. Suppressing the disease involves administering a vaccine of the present invention to a subject after induction of the disease but before its clinical appearance. Repressing the disease involves administering a vaccine of the present invention to a subject after clinical appearance of the disease.

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide, may indicate that the peptide or polypeptide differs in amino acid sequence by the insertion, deletion, or conservative substitution of amino acids, but retains at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated. This applies regardless of the breadth of the range.

2. COMPOSITIONS

The invention also includes novel sequences for use for producing antibodies. In one embodiment, the antibodies of the invention can be produced in mammalian cells or for delivery in DNA or RNA vectors including bacterial, yeast, as well as viral vectors.

The present invention relates to a composition comprising a recombinant nucleic acid sequence encoding an antibody, a fragment thereof, a variant thereof, or a combination thereof. The composition, when administered to a subject in need thereof, can result in the generation of a synthetic antibody in the subject. The synthetic antibody can bind a target molecule (i.e., an antigen, such as CTLA-4) present in the subject. Such binding can neutralize the antigen, block recognition of the antigen by another molecule, for example, a protein or nucleic acid, and elicit or induce an immune response to the antigen.

In one embodiment, the composition comprises a nucleotide sequence encoding a synthetic antibody. In one embodiment, the composition comprises a nucleic acid molecule comprising a first nucleotide sequence encoding a first synthetic antibody and a second nucleotide sequence encoding a second synthetic antibody. In one embodiment, the nucleic acid molecule comprises a nucleotide sequence encoding a cleavage domain.

In one embodiment, the nucleic acid molecule comprises a nucleotide sequence encoding one or more anti-CTLA-4 antibodies.

In one embodiment, the nucleotide sequence encoding an anti-CTLA-4 antibody comprises one or more codon optimized nucleic acid sequences encoding one or more amino acid sequences as set forth in SEQ ID NOs: 1, 2, 3, 4, 5, 6, or a fragment of one or more amino acid sequences as set forth in SEQ ID NOs: 1, 2, 3, 4, 5, 6.

In one embodiment, the nucleotide sequence has at least about 80% identity over the entire length of at least one nucleotide sequence selected from the group of SEQ ID NOs: 7, 8, 9, 10, 11, and 12.

In one embodiment, the nucleotide sequence encoding an anti-CTLA-4 antibody comprises one or more RNA sequences transcribed from one or more DNA sequences encoding an amino acid sequence at least 90% homologous to one or more of SEQ ID NOs: 1, 2, 3, 4, 5, 6, or a fragment of an amino acid sequence at least 90% homologous to one or more of SEQ ID NOs: 1, 2, 3, 4, 5, 6. In one embodiment, the nucleotide sequence encoding an anti-CTLA-4 antibody comprises one or more RNA sequences transcribed from one or more DNA sequences encoding an amino acid sequence as set forth in SEQ ID NOs: 1, 2, 3, 4, 5, 6, or a fragment of an amino acid sequence as set forth in SEQ ID NOs: 1, 2, 3, 4, 5, 6.

In one embodiment, the nucleotide sequence encoding an anti-CTLA-4 antibody comprises one or more codon optimized nucleic acid sequences at least 90% homologous to one or more nucleic acid sequences encoding one or more of SEQ ID NOs: 1, 2, 3, 4, 5, 6, or a fragment of a nucleic acid sequence at least 90% homologous to one or more nucleic acid sequences encoding one or more of SEQ ID NOs: 1, 2, 3, 4, 5, 6.

The composition of the invention can treat, prevent, and/or protect against any disease, disorder, or condition associated with CTLA-4 activity. In certain embodiments, the composition can treat, prevent, and/or protect against cancer.

In one embodiment, the composition of the invention is provided in combination with at least one other agent, such as an antigen. In one embodiment, a combination can be a single formulation or can be separate formulations and administered in sequence (either antigen first and then anti-CTLA-4 antibody, or anti-CTLA-4 antibody first and then antigen). The composition can increase antigen presentation and the overall immune response to the antigen in a subject. The combination of antigen and anti-CTLA-4 antibody induces the immune system more efficiently than a composition comprising the antigen alone. This more efficient immune response provides increased efficacy in the treatment and/or prevention of a disease, such as cancer.

The composition of the invention may comprise a checkpoint inhibitor. The checkpoint inhibitor may be one or more anti-CTLA-4 antibodies. The antigen may be one or more of hTERT, mTERT, PSA, PSMA, STEAP, PSCA, and PAP, WT1, tyrosinase, NYES01, PRAME, and MAGE. The checkpoint inhibitor(s) and the antigen(s) of the composition can be administered together or separately to the subject in need thereof, in nucleic acid or polypeptide forms. In some instances, the checkpoint inhibitor(s) can be administered separately from the antigen(s) of the composition.

The composition can result in the generation of the synthetic antibody in the subject within at least about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours, 60 hours, 72 hours, 84 hours, or 96 hours. The composition can be administered before or after administration of the antigen(s) to the subject. In some embodiments, the checkpoint inhibitor(s) can be administered at least 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 60 days, or 90 days before or after administration of the antigen(s) to the subject.

In still other embodiments, the checkpoint inhibitor(s) can be administered at least 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, or 15 weeks before or after administration of the antigen(s) to the subject. In other embodiments, the checkpoint inhibitor(s) can be administered about 12 hours to about 15 weeks, about 12 hours to about 10 weeks, about 12 hours to about 5 weeks, about 12 hours to about 1 week, about 12 hours to about 60 hours, about 12 hours to about 48 hours, about 24 hours to about 15 weeks, about 60 hours to about 15 weeks, about 96 hours to about 15 weeks, about 1 day to about 15 weeks, about 5 days to about 15 weeks, about 10 days to about 15 weeks, about 15 days to about 15 weeks, about 20 days to about 15 weeks, about 25 days to about 15 weeks, about 30 days to about 15 weeks, about 1 week to about 15 weeks, about 5 weeks to about 15 weeks, or about 10 weeks to about 15 weeks before or after administration of the antigen(s) to the subject.

The composition, when administered to the subject in need thereof, can result in the generation of the synthetic antibody in the subject more quickly than the generation of an endogenous antibody in a subject who is administered an antigen to induce a humoral immune response. The composition can result in the generation of the synthetic antibody at least about 1 day, 2 days, 3 days, 4 days, 5 days, 6 days, 7 days, 8 days, 9 days, or 10 days before the generation of the endogenous antibody in the subject who was administered an antigen to induce a humoral immune response.

The composition of the present invention can have features required of effective compositions such as being safe so that the composition does not cause illness or death; being protective against illness; and providing ease of administration, few side effects, biological stability, and low cost per dose. The composition may accomplish some or all of these features by combining the antigen(s) with the checkpoint inhibitor(s), such as an anti-CTLA-4 antibody as discussed herein.

a. Checkpoint Inhibitors

Checkpoint inhibitors can be any antagonist to the various immune checkpoints, and may be antibodies that block immune checkpoints. The antibodies can be a protein including a Fab, monoclonal or polyclonal. The antibodies can also be a DNA expression construct that encodes for and can express functional antibodies. The vaccine, in addition to one or more antigens, can further comprise a CTLA-4 antibody. The antibody can be a synthetic antibody comprised of DNA sequence encoding at least the variable regions of an immunoglobulin. Such antibody can be generated by identifying or screening for the antibody described herein, which is reactive to or binds the antigen described herein. The method of identifying or screening for the antibody can use the antigen in methodologies known to those skilled in art to identify or screen for the antibody. Such methodologies can include, but are not limited to, selection of the antibody from a library (e.g., phage display) and immunization of an animal followed by isolation and/or purification of the antibody. See for example methods available in Rajan, S., and Sidhu, S., *Methods in Enzymology*, vol 502, Chapter One "Simplified Synthetic Antibody Libraries (2012), which is incorporated herein in its entirety.

Any antibodies of the invention can also be combined with one or more other checkpoint inhibitor antibodies, including antibodies against one or more of PD-1, PD-L1, LAG-3, GITR, CD40, OX40, TIM-3, 4-1BB, and others. The checkpoint inhibitors can be a known product such as, for example, ipilimumab, tremelimumab, nivolumab, pembrolizumab, pidilizumab, BMS-936559 (See ClinicalTrials.gov Identifier NCT02028403), MPDL3280A (Roche, see ClinicalTrials.gov Identifier NCT02008227), MDX1105-01 (Bristol Myers Squibb, see ClinicalTrials.gov Identifier NCT00729664), MEDI4736 (MedImmune, See ClinicalTrials.gov Identifier NCT01693562), and MK-3475 (Merck, see ClinicalTrials.gov Identifier NCT02129556).

b. Recombinant Nucleic Acid Sequence

As described above, the composition can comprise a recombinant nucleic acid sequence. The recombinant nucleic acid sequence can encode the antibody, a fragment thereof, a variant thereof, or a combination thereof. The antibody is described in more detail elsewhere herein.

The recombinant nucleic acid sequence can be a heterologous nucleic acid sequence. The recombinant nucleic acid sequence can include one or more heterologous nucleic acid sequences.

The recombinant nucleic acid sequence can be an optimized nucleic acid sequence. Such optimization can increase or alter the immunogenicity of the antibody. Optimization can also improve transcription and/or translation. Optimization can include one or more of the following: low GC content leader sequence to increase transcription; mRNA stability and codon optimization; addition of a kozak sequence (e.g., GCC ACC) for increased translation; addition of an immunoglobulin (Ig) leader sequence encoding a signal peptide; addition of an internal IRES sequence and eliminating to the extent possible cis-acting sequence motifs (i.e., internal TATA boxes).

c. Recombinant Nucleic Acid Sequence Construct

The recombinant nucleic acid sequence can include one or more recombinant nucleic acid sequence constructs. The recombinant nucleic acid sequence construct can include one or more components, which are described in more detail herein.

The recombinant nucleic acid sequence construct can include a heterologous nucleic acid sequence that encodes a heavy chain polypeptide, a fragment thereof, a variant thereof, or a combination thereof. The recombinant nucleic acid sequence construct can include a heterologous nucleic acid sequence that encodes a light chain polypeptide, a fragment thereof, a variant thereof, or a combination thereof. The recombinant nucleic acid sequence construct can also include a heterologous nucleic acid sequence that encodes a protease or peptidase cleavage site. The recombinant nucleic acid sequence construct can also include a heterologous nucleic acid sequence that encodes an internal ribosome entry site (IRES). An IRES may be either a viral IRES or a eukaryotic IRES. The recombinant nucleic acid sequence construct can include one or more leader sequences, in which each leader sequence encodes a signal peptide. The recombinant nucleic acid sequence construct can include one or more promoters, one or more introns, one or more transcription termination regions, one or more initiation codons, one or more termination or stop codons, and/or one or more polyadenylation signals. The recombinant nucleic acid sequence construct can also include one or more linker or tag sequences. The tag sequence can encode a hemagglutinin (HA) tag.

(1) Heavy Chain Polypeptide

The recombinant nucleic acid sequence construct can include the heterologous nucleic acid encoding the heavy chain polypeptide, a fragment thereof, a variant thereof, or a combination thereof. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region.

In some embodiments, the heavy chain polypeptide can include a VH region and a CH1 region. In other embodiments, the heavy chain polypeptide can include a VH region, a CH1 region, a hinge region, a CH2 region, and a CH3 region.

The heavy chain polypeptide can include a complementarity determining region ("CDR") set. The CDR set can contain three hypervariable regions of the VH region. Proceeding from N-terminus of the heavy chain polypeptide, these CDRs are denoted "CDR1," "CDR2," and "CDR3," respectively. CDR1, CDR2, and CDR3 of the heavy chain polypeptide can contribute to binding or recognition of the antigen.

(2) Light Chain Polypeptide

The recombinant nucleic acid sequence construct can include the heterologous nucleic acid sequence encoding the light chain polypeptide, a fragment thereof, a variant thereof, or a combination thereof. The light chain polypeptide can include a variable light chain (VL) region and/or a constant light chain (CL) region.

The light chain polypeptide can include a complementarity determining region ("CDR") set. The CDR set can contain three hypervariable regions of the VL region. Proceeding from N-terminus of the light chain polypeptide, these CDRs are denoted "CDR1," "CDR2," and "CDR3," respectively. CDR1, CDR2, and CDR3 of the light chain polypeptide can contribute to binding or recognition of the antigen.

(3) Protease Cleavage Site

The recombinant nucleic acid sequence construct can include heterologous nucleic acid sequence encoding a protease cleavage site. The protease cleavage site can be recognized by a protease or peptidase. The protease can be an endopeptidase or endoprotease, for example, but not limited to, furin, elastase, HtrA, calpain, trypsin, chymotrypsin, trypsin, and pepsin. The protease can be furin. In other embodiments, the protease can be a serine protease, a threonine protease, cysteine protease, aspartate protease, metalloprotease, glutamic acid protease, or any protease that cleaves an internal peptide bond (i.e., does not cleave the N-terminal or C-terminal peptide bond).

The protease cleavage site can include one or more amino acid sequences that promote or increase the efficiency of cleavage. The one or more amino acid sequences can promote or increase the efficiency of forming or generating discrete polypeptides. The one or more amino acids sequences can include a 2A peptide sequence.

(4) Linker Sequence

The recombinant nucleic acid sequence construct can include one or more linker sequences. The linker sequence can spatially separate or link the one or more components described herein. In other embodiments, the linker sequence can encode an amino acid sequence that spatially separates or links two or more polypeptides.

(5) Promoter

The recombinant nucleic acid sequence construct can include one or more promoters. The one or more promoters may be any promoter that is capable of driving gene expression and regulating gene expression. Such a promoter is a cis-acting sequence element required for transcription via a DNA dependent RNA polymerase. Selection of the promoter used to direct gene expression depends on the particular application. The promoter may be positioned about the same distance from the transcription start in the recombinant nucleic acid sequence construct as it is from the transcription start site in its natural setting. However, variation in this distance may be accommodated without loss of promoter function.

The promoter may be operably linked to the heterologous nucleic acid sequence encoding the heavy chain polypeptide and/or light chain polypeptide. The promoter may be a promoter shown effective for expression in eukaryotic cells. The promoter operably linked to the coding sequence may be a CMV promoter, a promoter from simian virus 40 (SV40), such as SV40 early promoter and SV40 later promoter, a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, human polyhedrin, or human metalothionein.

The promoter can be a constitutive promoter or an inducible promoter, which initiates transcription only when the host cell is exposed to some particular external stimulus. In the case of a multicellular organism, the promoter can also be specific to a particular tissue or organ or stage of development. The promoter may also be a tissue specific promoter, such as a muscle or skin specific promoter, natural or synthetic. Examples of such promoters are described in US patent application publication no. US20040175727, the contents of which are incorporated herein in its entirety.

The promoter can be associated with an enhancer. The enhancer can be located upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

(6) Intron

The recombinant nucleic acid sequence construct can include one or more introns. Each intron can include functional splice donor and acceptor sites. The intron can include an enhancer of splicing. The intron can include one or more signals required for efficient splicing.

(7) Transcription Termination Region

The recombinant nucleic acid sequence construct can include one or more transcription termination regions. The transcription termination region can be downstream of the coding sequence to provide for efficient termination. The transcription termination region can be obtained from the same gene as the promoter described herein or can be obtained from one or more different genes.

(8) Initiation Codon

The recombinant nucleic acid sequence construct can include one or more initiation codons. The initiation codon can be located upstream of the coding sequence. The initiation codon can be in frame with the coding sequence. The initiation codon can be associated with one or more signals required for efficient translation initiation, for example, but not limited to, a ribosome binding site.

(9) Termination Codon

The recombinant nucleic acid sequence construct can include one or more termination or stop codons. The termination codon can be downstream of the coding sequence. The termination codon can be in frame with the coding sequence. The termination codon can be associated with one or more signals required for efficient translation termination.

(10) Polyadenylation Signal

The recombinant nucleic acid sequence construct can include one or more polyadenylation signals. The polyadenylation signal can include one or more signals required for efficient polyadenylation of the transcript. The polyadenylation signal can be positioned downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 plasmid (Invitrogen, San Diego, CA).

(11) Leader Sequence

The recombinant nucleic acid sequence construct can include one or more leader sequences. The leader sequence can encode a signal peptide. The signal peptide can be an immunoglobulin (Ig) signal peptide, for example, but not limited to, an IgG signal peptide and a IgE signal peptide.

d. Arrangement of the Recombinant Nucleic Acid Sequence Construct

As described above, the recombinant nucleic acid sequence can include one or more recombinant nucleic acid sequence constructs, in which each recombinant nucleic acid sequence construct can include one or more components. The one or more components are described in detail above. The one or more components, when included in the recombinant nucleic acid sequence construct, can be arranged in any order relative to one another. In some embodiments, the one or more components can be arranged in the recombinant nucleic acid sequence construct as described herein.

(1) Arrangement 1

In one arrangement, a first recombinant nucleic acid sequence construct can include the heterologous nucleic acid sequence encoding the heavy chain polypeptide and a second recombinant nucleic acid sequence construct can include the heterologous nucleic acid sequence encoding the light chain polypeptide.

The first recombinant nucleic acid sequence construct can be placed in a vector. The second recombinant nucleic acid sequence construct can be placed in a second or separate vector. Placement of the recombinant nucleic acid sequence construct into the vector is described in more detail herein.

The first recombinant nucleic acid sequence construct can also include the promoter, intron, transcription termination region, initiation codon, termination codon, and/or polyadenylation signal. The first recombinant nucleic acid sequence construct can further include the leader sequence, in which the leader sequence is located upstream (or 5') of the heterologous nucleic acid sequence encoding the heavy chain polypeptide. Accordingly, the signal peptide encoded by the leader sequence can be linked by a peptide bond to the heavy chain polypeptide.

The second recombinant nucleic acid sequence construct can also include the promoter, initiation codon, termination codon, and polyadenylation signal. The second recombinant nucleic acid sequence construct can further include the leader sequence, in which the leader sequence is located upstream (or 5') of the heterologous nucleic acid sequence encoding the light chain polypeptide. Accordingly, the signal peptide encoded by the leader sequence can be linked by a peptide bond to the light chain polypeptide.

Accordingly, one example of arrangement 1 can include the first vector (and thus first recombinant nucleic acid sequence construct) encoding the heavy chain polypeptide that includes VH and CH1, and the second vector (and thus second recombinant nucleic acid sequence construct) encoding the light chain polypeptide that includes VL and CL. A second example of arrangement 1 can include the first vector (and thus first recombinant nucleic acid sequence construct) encoding the heavy chain polypeptide that includes VH, CH1, hinge region, CH2, and CH3, and the second vector (and thus second recombinant nucleic acid sequence construct) encoding the light chain polypeptide that includes VL and CL.

(2) Arrangement 2

In a second arrangement, the recombinant nucleic acid sequence construct can include the heterologous nucleic acid sequence encoding the heavy chain polypeptide and the heterologous nucleic acid sequence encoding the light chain polypeptide. The heterologous nucleic acid sequence encoding the heavy chain polypeptide can be positioned upstream (or 5') of the heterologous nucleic acid sequence encoding the light chain polypeptide. Alternatively, the heterologous nucleic acid sequence encoding the light chain polypeptide can be positioned upstream (or 5') of the heterologous nucleic acid sequence encoding the heavy chain polypeptide.

The recombinant nucleic acid sequence construct can be placed in the vector as described in more detail herein.

The recombinant nucleic acid sequence construct can include the heterologous nucleic acid sequence encoding the protease cleavage site and/or the linker sequence. If included in the recombinant nucleic acid sequence construct, the heterologous nucleic acid sequence encoding the protease cleavage site can be positioned between the heterologous nucleic acid sequence encoding the heavy chain polypeptide and the heterologous nucleic acid sequence encoding the light chain polypeptide. Accordingly, the protease cleavage site allows for separation of the heavy chain polypeptide and the light chain polypeptide into distinct polypeptides upon expression. In other embodiments, if the linker sequence is included in the recombinant nucleic acid sequence construct, then the linker sequence can be positioned between the heterologous nucleic acid sequence encoding the heavy chain polypeptide and the heterologous nucleic acid sequence encoding the light chain polypeptide.

The recombinant nucleic acid sequence construct can also include the promoter, intron, transcription termination region, initiation codon, termination codon, and/or polyadenylation signal. The recombinant nucleic acid sequence construct can include one or more promoters. The recombinant nucleic acid sequence construct can include two promoters such that one promoter can be associated with the heterologous nucleic acid sequence encoding the heavy chain polypeptide and the second promoter can be associated with the heterologous nucleic acid sequence encoding the light chain polypeptide. In still other embodiments, the recombinant nucleic acid sequence construct can include one promoter that is associated with the heterologous nucleic acid sequence encoding the heavy chain polypeptide and the heterologous nucleic acid sequence encoding the light chain polypeptide.

The recombinant nucleic acid sequence construct can further include two leader sequences, in which a first leader sequence is located upstream (or 5') of the heterologous nucleic acid sequence encoding the heavy chain polypeptide and a second leader sequence is located upstream (or 5') of the heterologous nucleic acid sequence encoding the light chain polypeptide. Accordingly, a first signal peptide encoded by the first leader sequence can be linked by a peptide bond to the heavy chain polypeptide and a second signal peptide encoded by the second leader sequence can be linked by a peptide bond to the light chain polypeptide.

Accordingly, one example of arrangement 2 can include the vector (and thus recombinant nucleic acid sequence construct) encoding the heavy chain polypeptide that includes VH and CH1, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A second example of arrangement of 2 can include the vector (and thus recombinant nucleic acid sequence construct) encoding the heavy chain polypeptide that includes VH and CH1, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

A third example of arrangement 2 can include the vector (and thus recombinant nucleic acid sequence construct) encoding the heavy chain polypeptide that includes VH, CH1, hinge region, CH2, and CH3, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A fourth example of arrangement of 2 can include the vector (and thus recombinant nucleic acid sequence construct) encoding the heavy chain polypeptide that includes VH, CH1, hinge region, CH2, and CH3, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

e. Expression from the Recombinant Nucleic Acid Sequence Construct

As described above, the recombinant nucleic acid sequence construct can include, amongst the one or more components, the heterologous nucleic acid sequence encoding the heavy chain polypeptide and/or the heterologous nucleic acid sequence encoding the light chain polypeptide. Accordingly, the recombinant nucleic acid sequence construct can facilitate expression of the heavy chain polypeptide and/or the light chain polypeptide.

When arrangement 1 as described above is utilized, the first recombinant nucleic acid sequence construct can facilitate the expression of the heavy chain polypeptide and the second recombinant nucleic acid sequence construct can facilitate expression of the light chain polypeptide. When arrangement 2 as described above is utilized, the recombinant nucleic acid sequence construct can facilitate the expression of the heavy chain polypeptide and the light chain polypeptide.

Upon expression, for example, but not limited to, in a cell, organism, or mammal, the heavy chain polypeptide and the light chain polypeptide can assemble into the synthetic antibody. In particular, the heavy chain polypeptide and the light chain polypeptide can interact with one another such that assembly results in the synthetic antibody being capable of binding the antigen. In other embodiments, the heavy chain polypeptide and the light chain polypeptide can interact with one another such that assembly results in the synthetic antibody being more immunogenic as compared to an antibody not assembled as described herein. In still other embodiments, the heavy chain polypeptide and the light chain polypeptide can interact with one another such that assembly results in the synthetic antibody being capable of eliciting or inducing an immune response against the antigen.

f. Vectors

The recombinant nucleic acid sequence construct described above can be placed in one or more vectors. The one or more vectors can contain an origin of replication. The one or more vectors can be a plasmid, bacteriophage, bacterial artificial chromosome or yeast artificial chromosome. The one or more vectors can be either a self-replication extra chromosomal vector, or a vector which integrates into a host genome.

Vectors include, but are not limited to, plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. In some embodiments, the vector includes linear DNA, enzymatic DNA or synthetic DNA. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

The one or more vectors can be a heterologous expression construct, which is generally a plasmid that is used to introduce a specific gene into a target cell. Once the expression vector is inside the cell, the heavy chain polypeptide and/or light chain polypeptide that are encoded by the recombinant nucleic acid sequence construct is produced by the cellular-transcription and translation machinery ribosomal complexes. The one or more vectors can express large amounts of stable messenger RNA, and therefore proteins.

(1) Expression Vector

The one or more vectors can be a circular plasmid or a linear nucleic acid. The circular plasmid and linear nucleic acid are capable of directing expression of a particular nucleotide sequence in an appropriate subject cell. The one or more vectors comprising the recombinant nucleic acid sequence construct may be chimeric, meaning that at least one of its components is heterologous with respect to at least one of its other components.

(2) Plasmid

The one or more vectors can be a plasmid. The plasmid may be useful for transfecting cells with the recombinant nucleic acid sequence construct. The plasmid may be useful for introducing the recombinant nucleic acid sequence construct into the subject. The plasmid may also comprise a regulatory sequence, which may be well suited for gene expression in a cell into which the plasmid is administered.

The plasmid may also comprise a mammalian origin of replication in order to maintain the plasmid extrachromosomally and produce multiple copies of the plasmid in a cell. The plasmid may be pVAX, pCEP4 or pREP4 from Invitrogen (San Diego, CA), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may be pSE420 (Invitrogen, San Diego, Calif.), which may be used for protein production in *Escherichia coli* (*E. coli*). The plasmid may also be p YES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNAI or pcDNA3 (Invitrogen, San Diego, Calif.), which may be used for protein production in mammalian cells such as Chinese hamster ovary (CHO) cells.

(3) RNA

In one embodiment, the nucleic acid is an RNA molecule. In one embodiment, the RNA molecule is transcribed from a DNA sequence described herein. For example, in some embodiments, the RNA molecule is encoded by a DNA sequence at least 90% homologous to a DNA sequence encoding one of SEQ ID NOs: 1, 2, 3, 4, 5, 6, or a variant thereof or a fragment thereof. Accordingly, in one embodiment, the invention provides an RNA molecule encoding one or more of the MAbs or DMAbs. The RNA may be plus-stranded. Accordingly, in some embodiments, the RNA molecule can be translated by cells without needing any intervening replication steps such as reverse transcription. A RNA molecule useful with the invention may have a 5' cap (e.g. a 7-methylguanosine). This cap can enhance in vivo translation of the RNA. The 5' nucleotide of a RNA molecule useful with the invention may have a 5' triphosphate group. In a capped RNA this may be linked to a 7-methylguanosine via a 5'-to-5' bridge. A RNA molecule may have a 3' poly-A tail. It may also include a poly-A polymerase recognition sequence (e.g. AAUAAA) near its 3' end. A RNA molecule useful with the invention may be single-stranded. A RNA molecule useful with the invention may comprise synthetic RNA. In some embodiments, the RNA molecule is a naked RNA molecule. In one embodiment, the RNA molecule is comprised within a vector.

In one embodiment, the RNA has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of RNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many RNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the RNA.

In one embodiment, the RNA has both a cap on the 5' end and a 3' poly(A) tail which determine ribosome binding, initiation of translation and stability of RNA in the cell.

In one embodiment, the RNA is a nucleoside-modified RNA. Nucleoside-modified RNA have particular advantages over non-modified RNA, including for example, increased stability, low or absent innate immunogenicity, and enhanced translation.

(4) Circular and Linear Vector

The one or more vectors may be one or more circular plasmids, which may transform a target cell by integration into the cellular genome or exist extrachromosomally (e.g., autonomous replicating plasmid with an origin of replication). The vector can be pVAX, pcDNA3.0, or provax, or any other expression vector capable of expressing the heavy chain polypeptide and/or light chain polypeptide encoded by the recombinant nucleic acid sequence construct.

Also provided herein is a linear nucleic acid, or linear expression cassette ("LEC"), that is capable of being efficiently delivered to a subject via electroporation and expressing the heavy chain polypeptide and/or light chain polypeptide encoded by the recombinant nucleic acid sequence construct. The LEC may be any linear DNA devoid of any phosphate backbone. The LEC may not contain any antibiotic resistance genes and/or a phosphate backbone. The LEC may not contain other nucleic acid sequences unrelated to the desired gene expression.

The LEC may be derived from any plasmid capable of being linearized. The plasmid may be capable of expressing the heavy chain polypeptide and/or light chain polypeptide encoded by the recombinant nucleic acid sequence construct. The plasmid can be pNP (Puerto Rico/34) or pM2 (New Caledonia/99). The plasmid may be WLV009, pVAX, pcDNA3.0, or provax, or any other expression vector capable of expressing the heavy chain polypeptide and/or light chain polypeptide encoded by the recombinant nucleic acid sequence construct.

The LEC can be perM2. The LEC can be perNP. perNP and perMR can be derived from pNP (Puerto Rico/34) and pM2 (New Caledonia/99), respectively.

(5) Viral Vectors

In one embodiment, viral vectors are provided herein which are capable of delivering a nucleic acid of the invention to a cell. The expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector comprises an origin of replication functional in at least one organism, a promoter sequence, convenient restriction endonuclease sites, and one or more selectable markers. (See, e.g., WO 01/96584; WO 01/29058; and U.S. Pat. No. 6,326,193). Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

(6) Method of Preparing the Vector

Provided herein is a method for preparing the one or more vectors in which the recombinant nucleic acid sequence construct has been placed. After the final subcloning step, the vector can be used to inoculate a cell culture in a large scale fermentation tank, using known methods in the art.

In other embodiments, after the final subcloning step, the vector can be used with one or more electroporation (EP) devices. The EP devices are described herein in more herein.

The one or more vectors can be formulated or manufactured using a combination of known devices and techniques, and may be manufactured using a plasmid manufacturing technique that is described in U.S. provisional application U.S. Ser. No. 60/939,792, which was filed on May 23, 2007. In some examples, the DNA plasmids described herein can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

3. ANTIBODY

As described herein, the recombinant nucleic acid sequence can encode the antibody, a fragment thereof, a variant thereof, or a combination thereof. The antibody can bind or react with the antigen, which is described in more detail herein.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The antibody can treat, prevent, and/or protect against disease, such as cancer, in the subject administered a composition of the invention. The antibody, by binding the antigen, can treat, prevent, and/or protect against disease in the subject administered the composition. The antibody can promote survival of the disease in the subject administered the composition. In one embodiment, the antibody can provide increased survival of the disease in the subject over the expected survival of a subject having the disease who has not been administered the antibody. In various embodiments, the antibody can provide at least about a 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or a 100% increase in survival of the disease in subjects administered the composition over the expected survival in the absence of the composition. In one embodiment, the antibody can provide increased protection against the disease in the subject over the expected protection of a subject who has not been administered the antibody. In various embodiments, the antibody can protect against disease in at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% of subjects administered the composition over the expected protection in the absence of the composition.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')2 fragment, which comprises both antigen-binding sites. Accordingly, the antibody can be the Fab or F(ab')2. The Fab can include the heavy chain polypeptide and the light chain polypeptide. The heavy chain polypeptide of the Fab can include the VH region and the CH1 region. The light chain of the Fab can include the VL region and CL region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

The antibody can be a polyclonal or monoclonal antibody. The antibody can be a chimeric antibody, a single chain antibody, an affinity matured antibody, a human antibody, a humanized antibody, or a fully human antibody. The humanized antibody can be an antibody from a non-human species that binds the desired antigen having one or more complementarity determining regions (CDRs) from the non-human species and framework regions from a human immunoglobulin molecule.

The antibody can be a bispecific antibody as described herein in more detail. The antibody can be a bifunctional antibody as also described herein in more detail.

As described above, the antibody can be generated in the subject upon administration of the composition to the subject. The antibody may have a half-life within the subject. In some embodiments, the antibody may be modified to extend or shorten its half-life within the subject. Such modifications are described herein in more detail.

The antibody can be defucosylated as described in more detail herein.

The antibody may be modified to reduce or prevent antibody-dependent enhancement (ADE) of disease associated with the antigen as described in more detail herein.

a. Bispecific Antibody

The recombinant nucleic acid sequence can encode a bispecific antibody, a fragment thereof, a variant thereof, or a combination thereof. The bispecific antibody can bind or react with two antigens, for example, two of the antigens described herein in more detail. The bispecific antibody can be comprised of fragments of two of the antibodies described herein, thereby allowing the bispecific antibody to bind or react with two desired target molecules, which may include the antigen, which is described herein in more detail, a ligand, including a ligand for a receptor, a receptor, including a ligand-binding site on the receptor, a ligand-receptor complex, and a marker, including a cancer marker.

b. Bifunctional Antibody

The recombinant nucleic acid sequence can encode a bifunctional antibody, a fragment thereof, a variant thereof, or a combination thereof. The bifunctional antibody can bind or react with the antigen described herein. The bifunctional antibody can also be modified to impart an additional functionality to the antibody beyond recognition of and binding to the antigen. Such a modification can include, but is not limited to, coupling to factor H or a fragment thereof. Factor H is a soluble regulator of complement activation and thus, may contribute to an immune response via complement-mediated lysis (CML).

c. Extension of Antibody Half-Life

As described above, the antibody may be modified to extend or shorten the half-life of the antibody in the subject. The modification may extend or shorten the half-life of the antibody in the serum of the subject.

The modification may be present in a constant region of the antibody. The modification may be one or more amino acid substitutions in a constant region of the antibody that extend the half-life of the antibody as compared to a half-life of an antibody not containing the one or more amino acid substitutions. The modification may be one or more amino acid substitutions in the CH2 domain of the antibody that extend the half-life of the antibody as compared to a half-life of an antibody not containing the one or more amino acid substitutions.

In some embodiments, the one or more amino acid substitutions in the constant region may include replacing a methionine residue in the constant region with a tyrosine residue, a serine residue in the constant region with a threonine residue, a threonine residue in the constant region with a glutamate residue, or any combination thereof, thereby extending the half-life of the antibody.

In other embodiments, the one or more amino acid substitutions in the constant region may include replacing a methionine residue in the CH2 domain with a tyrosine residue, a serine residue in the CH2 domain with a threonine residue, a threonine residue in the CH2 domain with a glutamate residue, or any combination thereof, thereby extending the half-life of the antibody.

d. Defucosylation

The recombinant nucleic acid sequence can encode an antibody that is not fucosylated (i.e., a defucosylated antibody or a non-fucosylated antibody), a fragment thereof, a variant thereof, or a combination thereof. Fucosylation includes the addition of the sugar fucose to a molecule, for example, the attachment of fucose to N-glycans, 0-glycans and glycolipids. Accordingly, in a defucosylated antibody, fucose is not attached to the carbohydrate chains of the constant region. In turn, this lack of fucosylation may improve FcγRIIIa binding and antibody directed cellular cytotoxic (ADCC) activity by the antibody as compared to the fucosylated antibody. Therefore, in some embodiments, the non-fucosylated antibody may exhibit increased ADCC activity as compared to the fucosylated antibody.

The antibody may be modified so as to prevent or inhibit fucosylation of the antibody. In some embodiments, such a modified antibody may exhibit increased ADCC activity as compared to the unmodified antibody. The modification may be in the heavy chain, light chain, or a combination thereof. The modification may be one or more amino acid substitutions in the heavy chain, one or more amino acid substitutions in the light chain, or a combination thereof.

e. Reduced ADE Response

The antibody may be modified to reduce or prevent antibody-dependent enhancement (ADE) of disease associated with the antigen, but still neutralize the antigen.

In some embodiments, the antibody may be modified to include one or more amino acid substitutions that reduce or prevent binding of the antibody to FcγR1a. The one or more amino acid substitutions may be in the constant region of the antibody. The one or more amino acid substitutions may include replacing a leucine residue with an alanine residue in the constant region of the antibody, i.e., also known herein as LA, LA mutation or LA substitution. The one or more amino acid substitutions may include replacing two leucine residues, each with an alanine residue, in the constant region of the antibody and also known herein as LALA, LALA mutation, or LALA substitution. The presence of the LALA substitutions may prevent or block the antibody from binding to FcγR1a, and thus, the modified antibody does not enhance or cause ADE of disease associated with the antigen, but still neutralizes the antigen.

4. MONOCLONAL ANTIBODIES

In one embodiment, the invention provides anti-CTLA-4 antibodies. The antibodies may be intact monoclonal antibodies, and immunologically active fragments (e.g., a Fab or (Fab)$_2$ fragment), a monoclonal antibody heavy chain, or a monoclonal antibody light chain.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

5. METHOD OF GENERATING THE SYNTHETIC ANTIBODY

The present invention also relates a method of generating the synthetic antibody. The method can include administering the composition to the subject in need thereof by using the method of delivery described in more detail herein. Accordingly, the synthetic antibody is generated in the subject or in vivo upon administration of the composition to the subject.

The method can also include introducing the composition into one or more cells, and therefore, the synthetic antibody can be generated or produced in the one or more cells. The method can further include introducing the composition into one or more tissues, for example, but not limited to, skin and muscle, and therefore, the synthetic antibody can be generated or produced in the one or more tissues.

6. CANCER ANTIGEN

The compositions and methods of the invention can be used in combination with an antigen, or fragment or variant thereof.

Markers are known proteins that are present or upregulated vis-à-vis certain cancer cells. By methodology of generating antigens that represent such markers in a way to break tolerance to self, a cancer vaccine can be generated. Such cancer vaccines can include the checkpoint inhibitor(s) to enhance the immune response.

Aspects of the present invention include compositions for enhancing an immune response against an antigen in a subject in need thereof, comprising synthetic antibody in combination with a synthetic antigen capable of generating an immune response in the subject, or a biologically functional fragment or variant thereof. In some embodiments, the antigen comprises mTERT. In some embodiments, the antigen comprises hTERT.

The synthetic antigen can be an isolated DNA that encodes for the antigen. In one embodiment, the antigen is a tumor associated surface antigen. Illustrative examples of a tumor associated surface antigen are CD10, CD19, CD20, CD22, CD33, Fms-like tyrosine kinase 3 (FLT-3, CD135), chondroitin sulfate proteoglycan 4 (CSPG4, melanoma-associated chondroitin sulfate proteoglycan), Epidermal growth factor receptor (EGFR), Her2neu, Her3, IGFR, CD133, IL3R, fibroblast activating protein (FAP), CDCP1, Derlin1, Tenascin, frizzled 1-10, the vascular antigens VEGFR2 (KDR/FLK1), VEGFR3 (FLT4, CD309), PDGFR-.alpha. (CD140a), PDGFR-.beta. (CD140b) Endoglin, CLEC14, Tem1-8, and Tie2. Further examples may include A33, CAMPATH-1 (CDw52), Carcinoembryonic antigen (CEA), Carboanhydrase IX (MN/CA IX), CD21, CD25, CD30, CD34, CD37, CD44v6, CD45, CD133, de2-7 EGFR, EGFRvIII, EpCAM, Ep-CAM, Folate-binding protein, G250, Fms-like tyrosine kinase 3 (FLT-3, CD135), c-Kit (CD117), CSF1R (CD115), HLA-DR, IGFR, IL-2 receptor, IL3R, MCSP (Melanoma-associated cell surface chondroitin sulphate proteoglycane), Muc-1, Prostate-specific membrane antigen (PSMA), Prostate stem cell antigen (PSCA), Prostate specific antigen (PSA), and TAG-72. Examples of antigens expressed on the extracellular matrix of tumors are tenascin and the fibroblast activating protein (FAP).

In one embodiment, the synthetic antigen can be selected from the group including: hTERT, PSA, PSMA, STEAP, PSCA, and PAP, WT1, tyrosinase, NYES01, PRAME, and MAGE. The following are some exemplary cancer antigens:

a. hTERT hTERT is a human telomerase reverse transcriptase that synthesizes a TTAGGG tag on the end of telomeres to prevent cell death due to chromosomal shortening. Hyperproliferative cells with abnormally high expression of hTERT may be targeted by immunotherapy. Recent studies demonstrate that hTERT expression in dendritic cells transfected with hTERT genes can induce CD8+ cytotoxic T cells and elicit CD4+ T cells in an antigen-specific fashion.

hTERT can be administered in vectors described herein, and combined with checkpoint inhibitors in various vaccination schedules, including that in the Example, herein.

b. Prostate Antigens

The following are antigens capable of eliciting an immune response in a mammal against a prostate antigen. The consensus antigen can comprise epitopes that make them particularly effective as immunogens against prostate cancer cells can be induced. The consensus prostate antigen can comprise the full length translation product, a variant thereof, a fragment thereof or a combination thereof.

The prostate antigens can include one or more of the following: PSA antigen, PSMA antigen, STEAP antigen, PSCA antigen, Prostatic acid phosphatase (PAP) antigen, and other known prostate cancer markers. Proteins may comprise sequences homologous to the prostate antigens, fragments of the prostate antigens and proteins with sequences homologous to fragments of the prostate antigens.

The prostate antigens can be administered in vectors described herein, and combined with checkpoint inhibitors in various vaccination schedules, including that in the Example, herein.

c. WT1

The antigen can be Wilm's tumor suppressor gene 1 (WT1), a fragment thereof, a variant thereof, or a combination thereof. WT1 is a transcription factor containing at the N-terminus, a proline/glutamine-rich DNA-binding domain and at the C-terminus, four zinc finger motifs. WT1 plays a role in the normal development of the urogenital system and interacts with numerous factors, for example, p53, a known tumor suppressor and the serine protease HtrA2, which cleaves WT1 at multiple sites after treatment with a cytotoxic drug.

Mutation of WT1 can lead to tumor or cancer formation, for example, Wilm's tumor or tumors expressing WT1. Wilm's tumor often forms in one or both kidneys before metastasizing to other tissues, for example, but not limited to, liver tissue, urinary tract system tissue, lymph tissue, and lung tissue. Accordingly, Wilm's tumor can be considered a metastatic tumor. Wilm's tumor usually occurs in younger children (e.g., less than 5 years old) and in both sporadic and hereditary forms. Accordingly, the vaccine can be used for treating subjects suffering from Wilm's tumor. The vaccine can also be used for treating subjects with cancers or tumors that express WT1 for preventing development of such tumors in subjects. The WT1 antigen can differ from the native, "normal" WT1 gene, and thus, provide therapy or prophylaxis against an WT1 antigen-expressing tumor. Proteins may comprise sequences homologous to the WT1 antigens, fragments of the WT1 antigens and proteins with sequences homologous to fragments of the WT1 antigens.

The WT1 antigens can be administered in vectors described herein, and combined with checkpoint inhibitors in various vaccination schedules, including that in the Example, herein.

d. Tyrosinase Antigen

The antigen tyrosinase (Tyr) antigen is an important target for immune mediated clearance by inducing (1) humoral immunity via B cell responses to generate antibodies that block monocyte chemoattractant protein-1 (MCP-1) production, thereby retarding myeloid derived suppressor cells (MDSCs) and suppressing tumor growth; (2) increase cytotoxic T lymphocyte such as $CD8^+$ (CTL) to attack and kill tumor cells; (3) increase T helper cell responses; (4) and increase inflammatory responses via IFN-$\gamma$ and TFN-$\alpha$ or all of the aforementioned.

Tyrosinase is a copper-containing enzyme that can be found in plant and animal tissues. Tyrosinase catalyzes the production of melanin and other pigments by the oxidation of phenols such as tyrosine. In melanoma, tyrosinase can become unregulated, resulting in increased melanin synthesis. Tyrosinase is also a target of cytotoxic T cell recognition in subjects suffering from melanoma. Accordingly, tyrosinase can be an antigen associated with melanoma.

The antigen can comprise protein epitopes that make them particularly effective as immunogens against which anti-Tyr immune responses can be induced. The Tyr antigen can comprise the full-length translation product, a variant thereof, a fragment thereof or a combination thereof.

The Tyr antigen can comprise a consensus protein. The Tyr antigen induces antigen-specific T-cell and high titer antibody responses both systemically against all cancer and tumor related cells. As such, a protective immune response is provided against tumor formation by vaccines comprising the Tyr consensus antigen. Accordingly, any user can design a vaccine of the present invention to include a Tyr antigen to provide broad immunity against tumor formation, metastasis of tumors, and tumor growth. Proteins may comprise sequences homologous to the Tyr antigens, fragments of the Tyr antigens and proteins with sequences homologous to fragments of the Tyr antigens.

The Tyr antigens can be administered in vectors described herein, and combined with checkpoint inhibitors in various vaccination schedules, including that in the Example, herein.

e. NYES01

NY-ESO-1 is a cancer-testis antigen expressed in various cancers where it can induce both cellular and humoral immunity. Gene expression studies have shown upregulation of the gene for NY-ESO-1, CTAG1B, in myxoid and round cell liposarcomas. Proteins may comprise sequences homologous to the NYES01 antigens, fragments of the NYES01 antigens and proteins with sequences homologous to fragments of the NYES01 antigens.

The NYES01 antigens can be administered in vectors described herein, and combined with checkpoint inhibitors in various vaccination schedules, including that in the Example, herein.

f. PRAME

Melanoma antigen preferentially expressed in tumors (PRAME antigen) is a protein that in humans is encoded by the PRAME gene. This gene encodes an antigen that is predominantly expressed in human melanomas and that is recognized by cytolytic T lymphocytes. It is not expressed in normal tissues, except testis. The gene is also expressed in acute leukemias. Five alternatively spliced transcript variants encoding the same protein have been observed for this gene. Proteins may comprise sequences homologous to the PRAME antigens, fragments of the PRAME antigens and proteins with sequences homologous to fragments of the PRAME antigens.

The PRAME antigens can be administered in vectors described herein, and combined with checkpoint inhibitors in various vaccination schedules, including that in the Example, herein.

g. MAGE

MAGE stands for Melanoma-associated Antigen, and in particular melanoma associated antigen 4 (MAGEA4). MAGE-A4 is expressed in male germ cells and tumor cells of various histological types such as gastrointestinal, esophageal and pulmonary carcinomas. MAGE-A4 binds the oncoprotein, Gankyrin. This MAGE-A4 specific binding is mediated by its C-terminus. Studies have shown that exogenous MAGE-A4 can partly inhibit the adhesion-independent growth of Gankyrin-overexpressing cells in vitro and suppress the formation of migrated tumors from these cells in nude mice. This inhibition is dependent upon binding between MAGE-A4 and Gankyrin, suggesting that interactions between Gankyrin and MAGE-A4 inhibit Gankyrin-mediated carcinogenesis. It is likely that MAGE expression in tumor tissue is not a cause, but a result of tumor genesis, and MAGE genes take part in the immune process by targeting early tumor cells for destruction.

Melanoma-associated antigen 4 protein (MAGEA4) can be involved in embryonic development and tumor transformation and/or progression. MAGEA4 is normally expressed in testes and placenta. MAGEA4, however, can be expressed in many different types of tumors, for example, melanoma, head and neck squamous cell carcinoma, lung carcinoma, and breast carcinoma. Accordingly, MAGEA4 can be antigen associated with a variety of tumors.

The MAGEA4 antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-$\gamma$) and/or tumor necrosis factor alpha (TNF-$\alpha$). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-$\beta$, tumor associated macrophages, tumor associated fibroblasts.

The MAGEA4 antigen can comprise protein epitopes that make them particularly effective as immunogens against which anti-MAGEA4 immune responses can be induced. The MAGEA4 antigen can comprise the full length translation product, a variant thereof, a fragment thereof or a combination thereof. The MAGEA4 antigen can comprise a consensus protein.

The nucleic acid sequence encoding the consensus MAGEA4 antigen can be optimized with regards to codon usage and corresponding RNA transcripts. The nucleic acid encoding the consensus MAGEA4 antigen can be codon and RNA optimized for expression. In some embodiments, the nucleic acid sequence encoding the consensus MAGEA4 antigen can include a Kozak sequence (e.g., GCC ACC) to increase the efficiency of translation. The nucleic acid encoding the consensus MAGEA4 antigen can include multiple stop codons (e.g., TGA TGA) to increase the efficiency of translation termination.

The MAGE antigens can be administered in vectors described herein, and combined with checkpoint inhibitors in various vaccination schedules, including that in the Example, herein.

h. Tumor Antigen

In the context of the present invention, "tumor antigen" or "hyperproliferative disorder antigen" or "antigen associated with a hyperproliferative disorder," refers to antigens that are common to specific hyperproliferative disorders such as cancer. The antigens discussed herein are merely included by way of example. The list is not intended to be exclusive and further examples will be readily apparent to those of skill in the art.

Tumor antigens are proteins that are produced by tumor cells that elicit an immune response, particularly T-cell mediated immune responses. The selection of the antigen binding moiety of the invention will depend on the particular type of cancer to be treated. Tumor antigens are well known in the art and include, for example, a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

In one embodiment, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

The type of tumor antigen referred to in the invention may also be a tumor-specific antigen (TSA) or a tumor-associated antigen (TAA). A TSA is unique to tumor cells and does not occur on other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSA or TAA antigens include the following: Differentiation antigens such as MART-1/MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

7. EXCIPIENTS AND OTHER COMPONENTS OF THE COMPOSITION

The composition may further comprise a pharmaceutically acceptable excipient. The pharmaceutically acceptable excipient can be functional molecules such as vehicles, adjuvants, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate may be present in the composition at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the composition. The composition may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the composition is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be an adjuvant in addition to the checkpoint inhibitor antibodies of the invention. The additional adjuvant can be other genes that are expressed in an alternative plasmid or are delivered as proteins in combination with the plasmid above in the composition. The adjuvant may be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, PD-1, IL-10, IL-12, IL-18, or a combination thereof.

Other genes that can be useful as adjuvants in addition to the antibodies of the invention include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, IL-22, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The composition may further comprise a genetic facilitator agent as described in U.S. Ser. No. 021,579 filed Apr. 1, 1994, which is fully incorporated by reference.

The composition may comprise DNA at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, composition according to the present invention comprises about 5 nanogram to about 1000 micrograms of DNA. In some preferred embodiments, composition can contain about 10 nanograms to about 800 micrograms of DNA. In some preferred embodiments, the composition can contain about 0.1 to about 500 micrograms of DNA. In some preferred embodiments, the composition can contain about 1 to about 350 micrograms of DNA. In some preferred embodiments, the composition can contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of DNA.

The composition can be formulated according to the mode of administration to be used. An injectable pharmaceutical composition can be sterile, pyrogen free and particulate free. An isotonic formulation or solution can be used. Additives for isotonicity can include sodium chloride, dextrose, mannitol, sorbitol, and lactose. The composition can comprise a vasoconstriction agent. The isotonic solutions can include phosphate buffered saline. The composition can further comprise stabilizers including gelatin and albumin. The stabilizers can allow the formulation to be stable at room or ambient temperature for extended periods of time, including LGS or polycations or polyanions.

8. METHOD OF VACCINATION

The present invention is also directed to a method of increasing an immune response in a subject. Increasing the immune response can be used to treat and/or prevent disease in the subject. The method can include administering the herein disclosed vaccine to the subject. The subject administered the vaccine can have an increased or boosted immune response as compared to a subject administered the antigen alone. In some embodiments, the immune response can be increased by about 0.5-fold to about 15-fold, about 0.5-fold to about 10-fold, or about 0.5-fold to about 8-fold. Alternatively, the immune response in the subject administered the vaccine can be increased by at least about 0.5-fold, at least about 1.0-fold, at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, or at least about 15.0-fold.

In still other alternative embodiments, the immune response in the subject administered the vaccine can be increased about 50% to about 1500%, about 50% to about 1000%, or about 50% to about 800%. In other embodiments, the immune response in the subject administered the vaccine can be increased by at least about 50%, at least about 100%, at least about 150%, at least about 200%, at least about 250%, at least about 300%, at least about 350%, at least about 400%, at least about 450%, at least about 500%, at least about 550%, at least about 600%, at least about 650%, at least about 700%, at least about 750%, at least about 800%, at least about 850%, at least about 900%, at least about 950%, at least about 1000%, at least about 1050%, at least about 1100%, at least about 1150%, at least about 1200%, at least about 1250%, at least about 1300%, at least about 1350%, at least about 1450%, or at least about 1500%.

The vaccine dose can be between 1 μg to 10 mg active component/kg body weight/time, and can be 20 μg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, or 10.

9. METHOD OF DELIVERY OF THE COMPOSITION

The present invention also relates to a method of delivering the composition to the subject in need thereof. The method of delivery can include, administering the composition to the subject. Administration can include, but is not limited to, DNA injection with and without in vivo electroporation, liposome mediated delivery, and nanoparticle facilitated delivery.

The mammal receiving delivery of the composition may be human, primate, non-human primate, cow, cattle, sheep, goat, antelope, bison, water buffalo, bison, bovids, deer, hedgehogs, elephants, llama, alpaca, mice, rats, and chicken.

The composition may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal, intranasal, intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The composition may be administered by traditional syringes, needleless injection devices, "microprojectile bombardment gone guns", or other physical methods such as electroporation ("EP"), "hydrodynamic method", or ultrasound.

a. Electroporation

Administration of the composition via electroporation may be accomplished using electroporation devices that can be configured to deliver to a desired tissue of a mammal, a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (Inovio Pharmaceuticals, Plymouth Meeting, PA) or Elgen electroporator (Inovio Pharmaceuticals, Plymouth Meeting, PA) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 µs, 20 µs, 10 µs or 1 µs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the composition of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the composition include those provided in co-pending and co-owned U.S. patent application Ser. No. 11/874,072, filed Oct. 17, 2007, which claims the benefit under 35 USC 119(e) to U.S. Provisional Application Ser. No. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments, that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

10. CANCER THERAPY

The invention provides methods of treating or preventing cancer, or of treating and preventing growth or metastasis of tumors. Related aspects of the invention provide methods of preventing, aiding in the prevention, and/or reducing metastasis of hyperplastic or tumor cells in an individual.

One aspect of the invention provides a method of inhibiting metastasis in an individual in need thereof, the method comprising administering to the individual an effective amount of a composition of the invention. The invention further provides a method of inhibiting metastasis in an individual in need thereof, the method comprising administering to the individual an effective metastasis-inhibiting amount of any one of the compositions described herein.

In some embodiments of treating or preventing cancer, or of treating and preventing metastasis of tumors in an individual in need thereof, a second agent is administered to the individual, such as an antineoplastic agent. In some embodiments, the second agent comprises a second metastasis-inhibiting agent, such as a plasminogen antagonist, or an adenosine deaminase antagonist. In other embodiments, the second agent is an angiogenesis inhibiting agent.

The compositions of the invention can be used to prevent, abate, minimize, control, and/or lessen cancer in humans and animals. The compositions of the invention can also be used to slow the rate of primary tumor growth. The compositions of the invention when administered to a subject in need of treatment can be used to stop the spread of cancer cells. As such, the compositions of the invention can be administered as part of a combination therapy with one or more drugs or other pharmaceutical agents. When used as part of the combination therapy, the decrease in metastasis and reduction in primary tumor growth afforded by the compositions of the invention allows for a more effective and efficient use of any pharmaceutical or drug therapy being used to treat the patient. In addition, control of metastasis by the compositions of the invention affords the subject a greater ability to concentrate the disease in one location.

In one embodiment, the invention provides methods for preventing metastasis of malignant tumors or other cancerous cells as well as to reduce the rate of tumor growth. The methods comprise administering an effective amount of one or more of the compositions of the invention to a subject diagnosed with a malignant tumor or cancerous cells or to a subject having a tumor or cancerous cells.

The following are non-limiting examples of cancers that can be treated by the methods and compositions of the invention: Acute Lymphoblastic; Acute Myeloid Leukemia; Adrenocortical Carcinoma; Adrenocortical Carcinoma, Childhood; Appendix Cancer; Basal Cell Carcinoma; Bile Duct Cancer, Extrahepatic; Bladder Cancer; Bone Cancer; Osteosarcoma and Malignant Fibrous Histiocytoma; Brain Stem Glioma, Childhood; Brain Tumor, Adult; Brain Tumor, Brain Stem Glioma, Childhood; Brain Tumor, Central Nervous System Atypical Teratoid/Rhabdoid Tumor, Childhood; Central Nervous System Embryonal Tumors; Cerebellar Astrocytoma; Cerebral Astrocytotna/Malignant Glioma; Craniopharyngioma; Ependymoblastoma; Ependymoma; Medulloblastoma; Medulloepithelioma; Pineal Parenchymal Tumors of intermediate Differentiation; Supratentorial Primitive Neuroectodermal Tumors and Pineoblastoma; Visual Pathway and Hypothalamic Glioma; Brain and Spinal Cord Tumors; Breast Cancer; Bronchial Tumors; Burkitt Lymphoma; Carcinoid Tumor; Carcinoid Tumor, Gastrointestinal; Central Nervous System Atypical Teratoid/Rhabdoid Tumor; Central Nervous System Embryonal Tumors; Central Nervous System Lymphoma; Cerebellar Astrocytoma Cerebral Astrocytoma/Malignant Glioma, Childhood; Cervical Cancer; Chordoma, Childhood; Chronic Lymphocytic Leukemia; Chronic Myelogenous Leukemia; Chronic Myeloproliferative Disorders; Colon Cancer; Colorectal Cancer; Craniopharyngioma; Cutaneous T-Cell Lymphoma; Esophageal Cancer; Ewing Family of Tumors; Extragonadal Germ Cell Tumor; Extrahepatic Bile Duct Cancer; Eye Cancer, intraocular Melanoma; Eye Cancer, Retinoblastoma; Gallbladder Cancer; Gastric (Stomach) Cancer; Gastrointestinal Carcinoid Tumor; Gastrointestinal Stromal Tumor (GIST); Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer; Histiocytosis, Langerhans Cell; Hodgkin Lymphoma; Hypopharyngeal Cancer; Hypothalamic and Visual Pathway Glioma; intraocular Melanoma; Islet Cell Tumors; Kidney (Renal Cell) Cancer; Langerhans Cell Histiocytosis; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin; Lymphoma, Non-Hodgkin; Lymphoma, Primary Central Nervous System;

Macroglobulinemia, Waldenstrom; Malignant Fibrous Histiocvtoma of Bone and Osteosarcoma; Medulloblastoma; Melanoma; Melanoma, intraocular (Eye); Merkel Cell Carcinoma; Mesothelioma; Metastatic Squamous Neck Cancer with Occult Primary; Mouth Cancer; Multiple Endocrine Neoplasia Syndrome, (Childhood); Multiple Myeloma/Plasma Cell Neoplasm; Mycosis; Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Neuroblastoma; Non-Small Cell Lung Cancer; Oral Cancer; Oral Cavity Cancer; Oropharyngeal Cancer; Osteosarcoma and Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer, Islet Cell Tumors; Papillomatosis; Parathyroid Cancer; Penile Cancer; Pharyngeal Cancer; Pheochromocytoma; Pineal Parenchymal Tumors of Intermediate Differentiation; Pineoblastoma and Supratentorial Primitive Neuroectodermal Tumors; Pituitary Tumor; Plasma Celt Neoplasm/Multiple Myeloma; Pleuropulmonary Blastoma; Primary Central Nervous System Lymphoma; Prostate Cancer; Rectal Cancer; Renal Cell (Kidney) Cancer; Renal Pelvis and Ureter, Transitional Cell Cancer; Respiratory Tract Carcinoma Involving the NUT Gene on Chromosome 15; Retinoblastoma; Rhabdomyosarcoma; Salivary Gland Cancer; Sarcoma, Ewing Family of Tumors; Sarcoma, Kaposi; Sarcoma, Soft Tissue; Sarcoma, Uterine; Sezary Syndrome; Skin Cancer (Nonmelanoma); Skin Cancer (Melanoma); Skin Carcinoma, Merkel Cell; Small Cell Lung Cancer; Small Intestine Cancer; Soft Tissue Sarcoma; Squamous Cell Carcinoma, Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Throat Cancer; Thymoma and Thymic Carcinoma; Thyroid Cancer; Transitional Cell Cancer of the Renal Pelvis and Ureter; Trophoblastic Tumor, Gestational; Urethral Cancer; Uterine Cancer, Endometrial; Uterine Sarcoma; Vaginal Cancer; Vulvar Cancer; Waldenstrom Macroglobulinemia; and Wilms Tumor.

In one embodiment, the invention provides a method to treat cancer metastasis comprising treating the subject prior to, concurrently with, or subsequently to the treatment with a composition of the invention, with a complementary therapy for the cancer, such as surgery, chemotherapy, chemotherapeutic agent, radiation therapy, or hormonal therapy or a combination thereof.

Chemotherapeutic agents include cytotoxic agents (e.g., 5-fluorouracil, cisplatin, carboplatin, methotrexate, daunorubicin, doxorubicin, vincristine, vinblastine, oxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozoci), cytotoxic alkylating agents (e.g., busulfan, chlorambucil, cyclophosphamide, melphalan, or ethylesulfonic acid), alkylating agents (e.g., asaley, AZQ, BCNU, busulfan, bisulphan, carboxyphthalatoplatinum, CBDCA, CCNU, CHIP, chlorambucil, chlorozotocin, cis-platinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864), antimitotic agents (e.g., allocolchicine, Halichondrin M, colchicine, colchicine derivatives, dolastatin 10, maytansine, rhizoxin, paclitaxel derivatives, paclitaxel, thiocolchicine, trityl cysteine, vinblastine sulfate, and vincristine sulfate), plant alkaloids (e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere), biologicals (e.g., alpha interferon, BCG, G-CSF, GM-CSF, and interleukin-2), topoisomerase I inhibitors (e.g., camptothecin, camptothecin derivatives, and morpholinodoxorubicin), topoisomerase II inhibitors (e.g., mitoxantron, amonafide, m-AMSA, anthrapyrazole derivatives, pyrazoloacridine, bisantrene HCL, daunorubicin, deoxydoxorubicin, menogaril, N,N-dibenzyl daunomycin, oxanthrazole, rubidazone, VM-26 and VP-16), and synthetics (e.g., hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium).

Antiproliferative agents are compounds that decrease the proliferation of cells. Antiproliferative agents include alkylating agents, antimetabolites, enzymes, biological response modifiers, miscellaneous agents, hormones and antagonists, androgen inhibitors (e.g., flutamide and leuprolide acetate), antiestrogens (e.g., tamoxifen citrate and analogs thereof, toremifene, droloxifene and roloxifene), Additional examples of specific antiproliferative agents include, but are not limited to levamisole, gallium nitrate, granisetron, sargramostim strontium-89 chloride, filgrastim, pilocarpine, dexrazoxane, and ondansetron.

The compounds of the invention can be administered alone or in combination with other anti-tumor agents, including cytotoxic/antineoplastic agents and anti-angiogenic agents. Cytotoxic/anti-neoplastic agents are defined as agents which attack and kill cancer cells. Some cytotoxic/anti-neoplastic agents are alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents are antimetabolites for tumor cells, e.g., cytosine arabinoside, fluorouracil, methotrexate, mercaptopuirine, azathioprime, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (*vinca* alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents are well known to those of skill in the art. Suitable anti-angiogenic agents for use in the methods and compositions of the invention include anti-VEGF antibodies, including humanized and chimeric antibodies, anti-VEGF aptamers and antisense oligonucleotides. Other known inhibitors of angiogenesis include angiostatin, endostatin, interferons, interleukin 1 (including alpha and beta) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Other anti-cancer agents that can be used in combination with the compositions of the invention include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. In one embodiment, the anti-cancer drug is 5-fluorouracil, taxol, or leucovorin.

The present invention is further illustrated in the following Examples. It should be understood that these Examples, while indicating exemplary embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

11. EXAMPLES

Example 1

Targeting Immune Suppression in Tumors with Immune Checkpoint Blockade Using DNA Monoclonal Antibodies (DMAb)

Here a novel platform for the administration of immune checkpoint blockade antibodies through the use of DNA plasmids encoding IgG is described. The CELLECTRA electroporation approach described here has been widely used in clinical DNA vaccine trials, has a favorable safety and tolerability profile, and would be more rapid and cost efficient for mAb delivery compared to intravenous injection, which may broaden the applications that can be used for checkpoint antibodies (Trimble et al., 2015, Lancet, 386(10008):2078-2088; Tebas et al., 2017, N Engl J Med. EPub ahead of print). In these pre-clinical studies, engineered DMAbs were efficient at driving in vivo expression of anti-CTLA-4 mAbs, and exhibited properties of IgG encoded CTLA-4 mAb. The DMAbs were capable of inducing potent anti-tumor immunity and CD8 T cell infiltration while decreasing Treg infiltration. These results suggest that this technology could be used for novel therapeutic approaches that are currently limited for biologic mAbs, such as maintenance therapies.

Both DNA plasmid and viral delivery approaches have been used in pre-clinical models to deliver therapeutic mAbs for cancer therapy (Jiang et al., 2006, Clin Cancer Res, 12(20 Pt 1):6179-6185; Watanabe et al., 2010, Gene Ther, 17(8):1042-1051; Shi et al., 2006, Cancer Res, 66:11946-53). However, these approaches thus far have focused on antibodies targeting cancer surface antigens or angiogenic factors. While viral vectors can drive high expression, their use is limited to seronegative individuals, they can genetically mark patients, and they are difficult to re-administer due to seroconversion (Hollevoet and Declerck, 2017, J Transl Med. BioMed Central, 15:131). Here, it is reported that the DMAb approach for immune checkpoint delivery can result in significant and prolonged in vivo expression from as little as a single dose.

Immune checkpoint blockade combination therapies are showing synergy in the clinic for certain indications (Ribas and Wolchok, 2018, American Association for the Advancement of Science, 359:1350-1355). While combination therapy between ipilimumab and nivolumab is highly effective in melanoma patients, it also results in even more toxicity compared to monotherapy (Wolchok et al., 2017, N Engl J Med. Massachusetts Medical Society, 377:1345-1356). Unfortunately, the full scope of this toxicity was difficult to predict using pre-clinical mouse or non-human primate models (Keler et al., 2003, J Immunol. American Association of Immunologists; 171:6251-6259; Selby et al., 2016, PLoS One, 2016; 11:e0161779). Due to this toxicity concern, next generation versions of ipilimumab that can be selectively activated within tumors are currently being developed and tested in clinical trials (Arce Vargas et al., 2018, Cancer Cell, 33(4):649-663; Korman et al., 2017, Cancer Res, 77:SY09-01). Additional designs are being developed to enhance the effector function induced by these antibodies, including Fc mutations that enhance binding to the human FcγRIIIa as well as non-fucosylated versions with enhanced antibody-dependent cell-mediated cytotoxicity activity (Arce Vargas et al., 2018, Cancer Cell, 33(4):649-663; Lazar et al., Proc Natl Acad Sci USA, 103(11):4005-4010). These important antibody improvements may provide expanded uses for CTLA-4 targeted antibodies in the future (e.g., combination therapy with anti-PD1 DMAbs or with vaccines.)

The materials and methods used for the experiments are now described

Cell Culture and Transfection

HEK293T cells, CT26 and Sa1N tumor cells were obtained from ATCC, which performs thorough testing and authentication of their cell lines using morphology, karyotyping and PCR based approaches. They were maintained in Dulbecco's Modified Eagle Medium (DMEM) supplemented with 10% fetal bovine serum (FBS). They were both routinely tested for Mycoplasma contamination, and maintained at low passage (<20 passages) in cell culture. Only Sa1N or CT26 cells at lower than passage 5 were implanted into mice. HEK293T cells were transfected with GeneJammer transfection reagent according to the manufacturer's recommendations (Agilent). Cells and conditioned media were harvested 48 hours after transfection using RIPA lysis buffer (Cell Signaling Technology) containing EDTA-free protease inhibitor (Roche) for analysis by western blot.

DNA Plasmid Construction

The amino acid sequences for 9D9, ipilimumab and tremelimumab were obtained from published patents or available DrugBank sequences (U.S. Pat. No. 9,868,961B2 for 9D9). The nucleotide sequence for the mouse IgG2b (9D9) was codon optimized for mouse to enhance mammalian expression, and the nucleotide sequences for the human IgG1 (ipilimumab) and IgG2 (tremelimumab) were optimized for both mouse and human codon biases. All sequences were also RNA optimized and included a Kozak sequence. Plasmids were cloned into the modified pVax1 plasmid with a human cytomegalovirus promoter and bovine growth hormone polyA sequence (GenScript). Both heavy and light chains were encoded in the same plasmid, separated by a furin cleavage site (RGRKRRS; SEQ ID NO:17) and a P2A peptide to ensure cleavage. Additional sequence modifications for 9D9 were made based on sequence alignment to the mouse germline IGHV1-19*01 sequence, and are indicated in FIG. 1 and Table 1.

TABLE 1

Sequences for DMAbs used in these experiments.

| SEQ ID NO: | Type | Description |
|---|---|---|
| 1 | Amino Acid | 9D9 DMAb original |
| 2 | Amino Acid | 9D9 DMAb mod #2 |
| 3 | Amino Acid | 9D9 DMAb mod #3 |
| 4 | Amino Acid | 9D9 DMAb mod #4 |
| 5 | Amino Acid | Tremelimumab DMAb |
| 6 | Amino Acid | Ipilimumab DMAb |
| 7 | Nucleotide | 9D9 DMAb original |
| 8 | Nucleotide | 9D9 DMAb mod #2 |
| 9 | Nucleotide | 9D9 DMAb mod #3 |
| 10 | Nucleotide | 9D9 DMAb mod #4 |
| 11 | Nucleotide | Tremelimumab DMAb |
| 12 | Nucleotide | Ipilimumab DMAb |

DMAb Injection and Mouse Tumor Studies

C57Bl/6, Balb/c and A/J mice were purchased from Jackson laboratories. DNA plasmids were formulated with 12 Units of hyaluronidase enzyme (Sigma-Aldrich) in 30 µL total injection volume. Formulated DNA plasmid was injected at one site (100 µg) in the tibialis anterior (TA) muscle, or at 4 sites (100 µg per site) in both TA muscles and quadriceps muscles. Following plasmid injection, the muscles were pulsed with two 0.1 Amp electric constant current square-wave pulses using the CELLECTRA®-3P device (Inovio Pharmaceuticals). For tumor challenge studies, A/J or Balb/c mice were implanted subcutaneously with 10 million Sa1N tumor cells or 500,000 CT26 tumor cells, respectively, in PBS on the right flank. As human antibodies are immunogenic in immune competent mice, their expression was studied in Balb/c mice that were depleted of CD4+ and CD8+ T cells transiently at the time of DMAb injection (using a 200 µg injection of clone GK1.5 and clone YTS 169.4, BioXCell). For tumor studies, mice were euthanized when tumors reached 1.5 cm in diameter. All mice still alive at the end of study cleared their tumors completely.

Human Peripheral Blood Mononuclear Cell (PBMC) Isolation

Human blood was obtained from consenting adult healthy volunteers through the Wistar Phlebotomy core under Institutional Review Board (IRB) approved protocol #21801304. Written informed consent was obtained from all patients, and studies were conducted in accordance with recognized ethical guidelines. Whole blood was collected in heparinized tubes and subsequently layered on top of an equal volume of histopaque 1083 (Sigma-Aldrich).

CTLA-4 Blockade Luciferase Assay

T cell activation after CTLA-4 blockade was assessed using the CTLA-4 Blockade Bioassay (Promega), according to manufacturer's instructions. Ipilimumab and tremelimumab DMAb was purified from individual mice for this assay (n=3 mice for each DMAb), using the Nab Protein A/G Spin Kit (ThermoFisher), and was concentrated using Amicon Ultra Centrifugal Filters (Millipore Sigma). Luciferase activity was measured using the Synergy2 plate reader (Biotek).

Western Blot

Western blot analysis was performed using NuPAGE reagents (ThermoFisher Scientific) and PVDF membranes (Millipore). Odyssey blocking buffer was used for blocking and antibody incubation. Detection antibodies (IRDye800RD goat anti-mouse and IRDye800RD goat anti-human) were diluted at 1:10,000 dilution in Odyssey blocking buffer containing 0.1% Tween-20 and 0.01% SDS. Membranes were imaged using the LiCor Odyssey CLx. The Odyssey One-Color Protein molecular weight marker was used as a ladder in the 680RD channel (red).

ELISA Assay

For quantification of human IgG antibodies in culture or in mouse serum, 96-well Nunc MaxiSorp plates were coated with 10 µg/mL of goat anti-human IgG Fc fragment (Bethyl) overnight at 4° C. Plates were blocked with 10% fetal calf serum (FCS) in PBS for 1 hour at room temperature. Both primary and secondary antibodies were incubated for 1 hour at room temperature. Standard curves consisting of a known concentration of human IgG (Bethyl) were used for quantitation as a primary antibody on each ELISA plate. HRP-conjugated goat anti-human kappa light chain (Bethyl) was used at a 1:20,000 dilution for secondary antibody incubation. Plates were washed four times with PBS-T (0.2% Tween-20 in PBS) between antibody incubations. Plates were developed using SigmaFastOPD (Sigma-Aldrich) development for 10 minutes at room temperature. Development was stopped after 10 minutes using 1M H2SO4. Absorbance (OD 450 nm) was measured using a Synergy2 plate reader at OD450 (Biotek).

Mouse IgG was quantified in cell culture using the same basic procedure, with the following antibodies: 10 µg/mL of goat anti-mouse IgG Fc fragment for coat protein (Bethyl), purified mouse IgG (Bethyl) for standard curve, and HRP conjugated goat anti-mouse light chain antibody (Millipore) at a 1:20,000 dilution.

Anti-CTLA-4 mouse IgG was quantified in cell culture or mouse serum with a binding ELISA using the same basic procedure with the following reagents: 1 µg/mL of mouse CTLA-4 protein for coat protein (MyBioSource), recombinant 9D9 (BioXCell) for standard curve, and HRP conjugated goat anti-mouse light chain antibody (Millipore) at 1:5,000 dilution. For this binding ELISA, plates were developed for 20 minutes.

Immunofluorescence Staining

For immunofluorescence staining, Sa1N tumors were harvested and frozen in O.C.T. (Tissue-Tek) on dry ice. Frozen tissue was stored at −80° C. Tissue was sectioned onto PermaFrost slides. Frozen tissue was fixed with 4% paraformaldehyde (in PBS) for 15 minutes at room temperature, washed with PBS and permeabilized with 0.5% Triton X-100 for 15 minutes at room temperature. Tissue was blocked for 1 hour at room temperature in 2.5% BSA and 5% horse serum in PBS. Slides were incubated in Avidin/Biotin Blocking Kit buffers (Vector Labs) prior to primary antibody incubation. The following primary antibodies were used: CD8α-biotin (Biolegend, clone 53-6.7, 1:2000) and CD3ε-biotin (Biolegend, clone 145-2C11, 1:2000). Primary antibody was incubated overnight at 4° C. in 2.5% BSA and 5% horse serum in PBS in a humidified chamber. The TSA-Biotin kit (Perkin Elmer) was used for signal amplification, followed by secondary antibody incubation in 1% horse serum in PBS for 30 minutes at room temperature (Streptavidin AF488, 1:500). Slides were mounted with Prolong Gold Antifade, and imaged using a Zeiss LSM Confocal microscope at the University of Pennsylvania Cell and Developmental Biology Microscopy Core. Numbers of CD3 and CD8 cells were counted using Fiji/ImageJ software.

Human Peripheral Blood Mononuclear Cell (PBMC) Stimulation

Cells were spun, and PBMCs were collected from the buffy coat for stimulation with Cell Stimulation Cocktail containing a mixture of phorbol 12-myristate 13-acetate (PMA) and ionomycin (eBioscience). Cells were stimulated in RPMI 1640 media containing 10% FBS, 1% Penicillin/Streptomycin, 0.5 mM sodium pyruvate, 50 µM β-mercaptoethanol, 1% glutamax/glutamine and 0.1 U/mL IL-2 (Peprotech).

Mouse TIL Isolation

Mouse Sa1N tumors were minced using a scalpel, and incubated in a tumor dissociation enzyme mix consisting of: 170 mg/L Collagenase I, II and IV (ThermoFisher), 12.5 mg/L DNAse I (Roche), 25 mg/L Elastase (Worthington) in 50% RPMI+10% FBS and 50% Hyclone L-15 Leibowitz medium (ThermoFisher). Tumors were incubated in this mixture with end-over-end mixing for 1 hour at 37° C., and then filtered twice through a 40 µm filter prior to plating for staining.

Staining of Human PBMCs and Mouse TILs for Flow Cytometry

The following antibodies were used for human T cell staining: CD4 BV510 (OKT4, 1:200, biolegend), CD8 ApcCy7 (SK1, 1:200, biolegend), CD25 APC (BC96, 1:200, biolegend), CD3 BV650 (SP34-2, 1:200, biolegend), CD152 PE (1:100, BD Biosciences) and anti-human PE (1:100, biolegend). The following antibodies were used for mouse TIL staining: CD45 FITC (30-F11, 1:200, biolegend), FoxP3 APC (FJK-16s, 1:100, ebioscience), CD44 AF700 (IM7, 1:200, biolegend), CD8 APC-Cy7 (53-6.7, 1:200, biolegend), CD3 PE-Cy5 (145-2C11, 1:100, BD Pharmingen), CD25 PE-Cy7 (PC61.5, 1:100, ebioscience), CD69 BV605 (H1.2F3, 1:200, biolegend), and PD-1 BV711 (29F.1A12, 1:100, biolegend). First, cells were washed and incubated with LIVE/DEAD violet (ThermoFisher), and subsequently incubated with surface antibodies in 1% FBS in PBS for 30 minutes at room temperature. Cells were then fixed and permeabilized (BD Biosciences) for 15 minutes at 4° C. Cells were then incubated with CD3 antibody (human samples) or FoxP3 antibody (mouse samples) in fixation/permeabilization wash buffer for 1 hour at 4° C. Samples were run on an LSR18 flow cytometer (BD Biosciences), and data was analyzed using FlowJo software (TreeStar).

The results of the experiments are now described

Design, Expression and Binding of Mouse Anti-Mouse CTLA-4 DMAbs

The mouse anti-mouse CTLA-4 9D9 clone was used to encode in the optimized DNA expression system, based on its previously described anti-tumor activity (Selby et al., Cancer Immunol Res. 2013; 1:32-42; Arce Vargas et al., 2018, Cancer Cell, 33(4):649-663). The design for this DMAb plasmid was built off prior DMAb work in the infectious disease space, and is described in detail in the methods section (Elliot et al., 2017, NPJ Vaccines, 2:18; Patel et al., 2017, Nat Commun, 8:637).

Transfected HEK293T cells were able to produce and secrete 9D9 DMAb antibody in vitro, detected by ELISA and western blot (FIG. 2A,B). However, expression of this DMAb was low (~660 ng/mL) compared to other previously examined DMAbs (Elliot et al., 2017, NPJ Vaccines, 2:18; Patel et al., 2017, Nat Commun, 8:637). Therefore several modifications were engineered into the DMAb to improve expression, including modification of the beginning and end of the heavy chain sequence FIG. 1A,B. While modification of the end sequence alone (mod #2) only slightly improved antibody production in vitro, modification of the beginning sequence or both sequences significantly improved antibody production, with nearly a 10-fold improvement in antibody secretion to the media for mod #4 (FIG. 2B). These framework modifications did not alter the binding to mouse CTLA-4 protein by ELISA, with similar $IC_{50}$ values compared to recombinant 9D9 (range 36.105-44.25 ng/mL) (FIG. 2C).

Next, expression of these DMAbs was tested in C57Bl/6 mice through delivery by IM-EP (100 µg) (FIG. 2D). Similar to the in vitro results, the original 9D9 DMAb produced antibody in the serum at relatively low levels (~1.2 µg/mL of serum) (FIG. 2D). All three modified DMAbs expressed at higher levels, with the mod #4 producing levels of ~7.9 µg/mL, over 6-fold higher than the original DMAb sequence (FIG. 2D). These important framework modifications therefore greatly improved both in vitro and in vivo expression of this DMAb without altering binding to mouse CTLA-4 protein.

Anti-Tumor Activity of Anti-Mouse CTLA-4 DMAb in Multiple Tumor Models

Figures 3A, 3B, 3C, 3D:
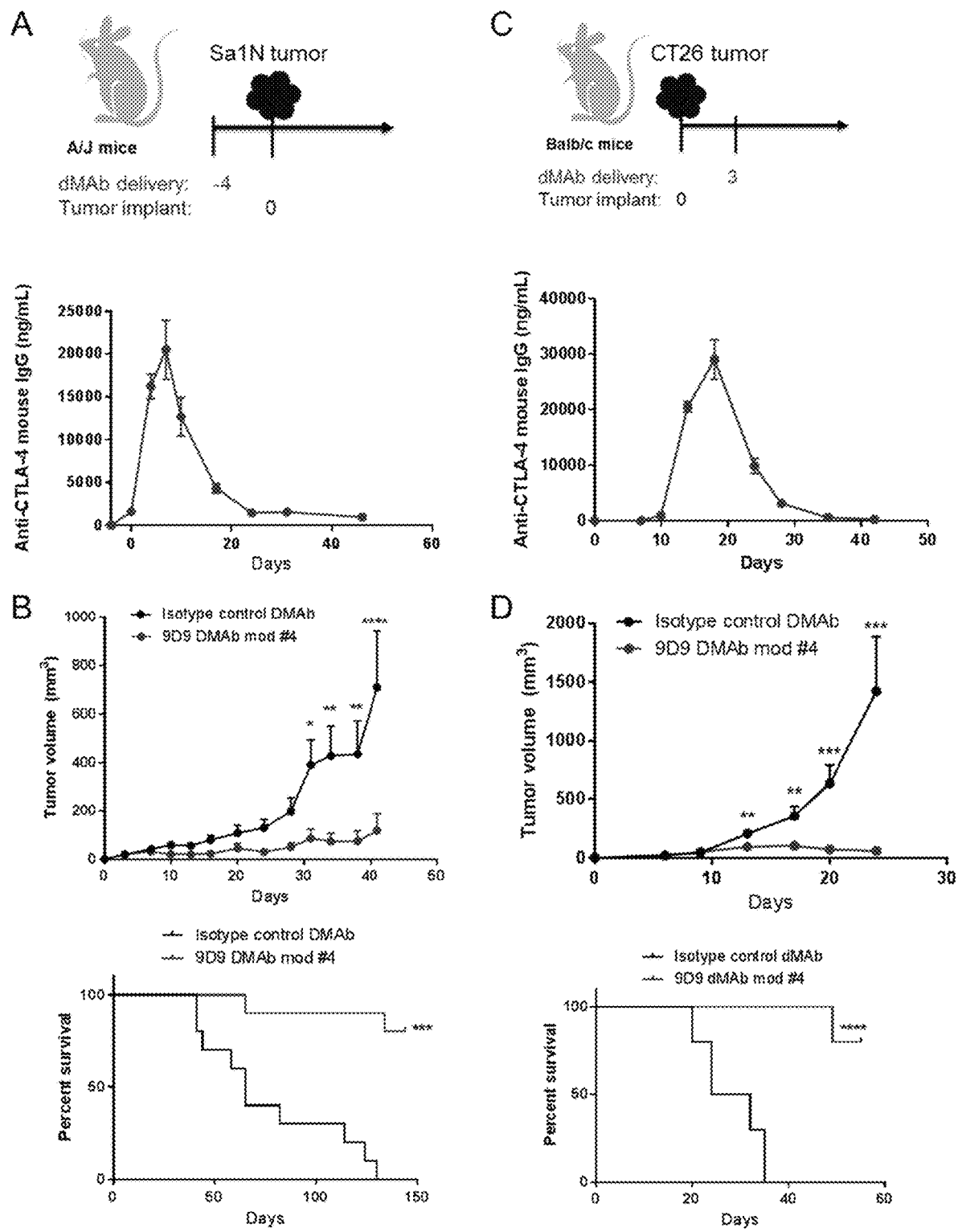
FIG. 3A through FIG. 3D, depicts exemplary experimental results demonstrating the anti-tumor activity of anti-CTLA-4 DMAb in Sa1N and CT26 tumor models.
Figures 4A, 4B, 4C, 4D:
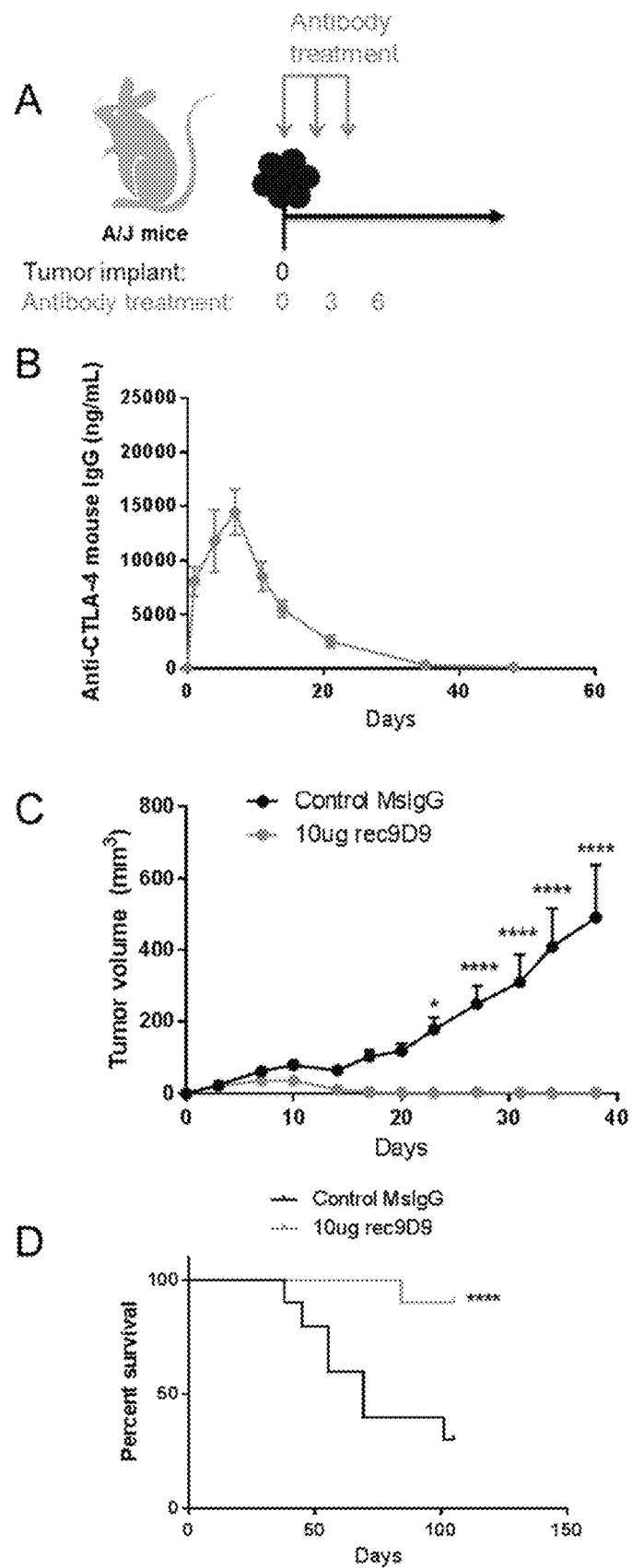
FIG. 4A through FIG. 4D, depicts exemplary experimental results demonstrating the efficacy of recombinant 9D9 antibody in Sa1N tumor model.
Figure 5:
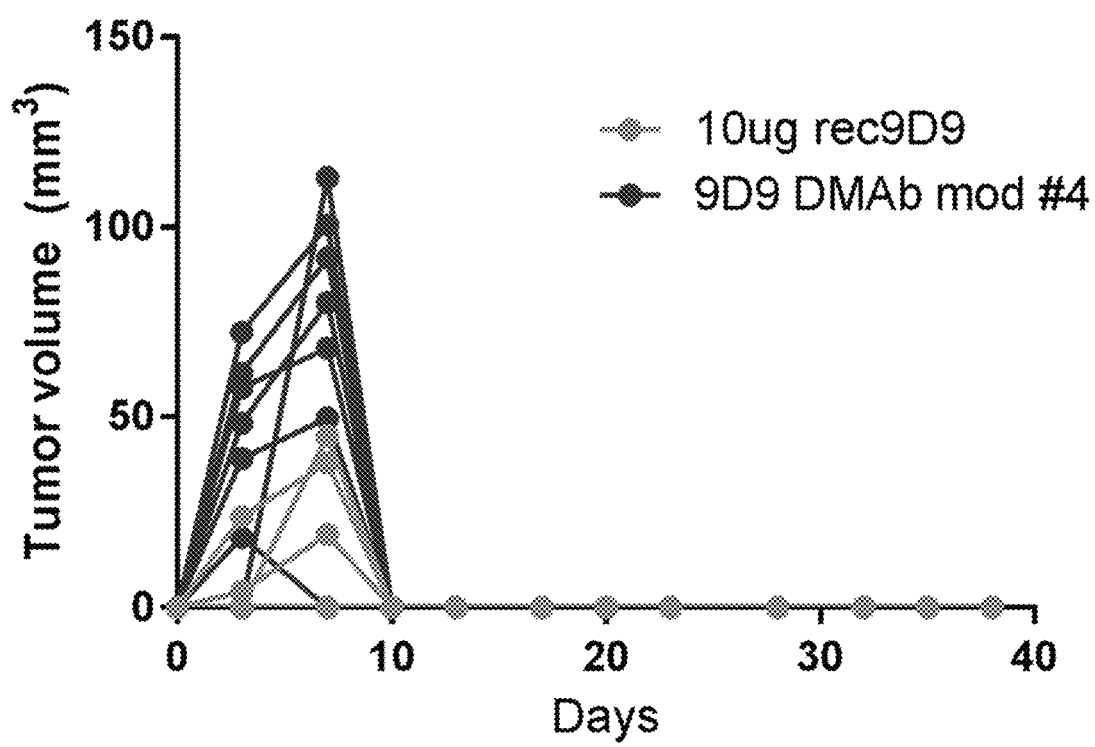
FIG. 5 depicts exemplary experimental results demonstrating mouse anti-mouse CTLA-4 DMAb induces immune memory and protection from tumor re-challenge.
Figures 6A, 6B, 6C:
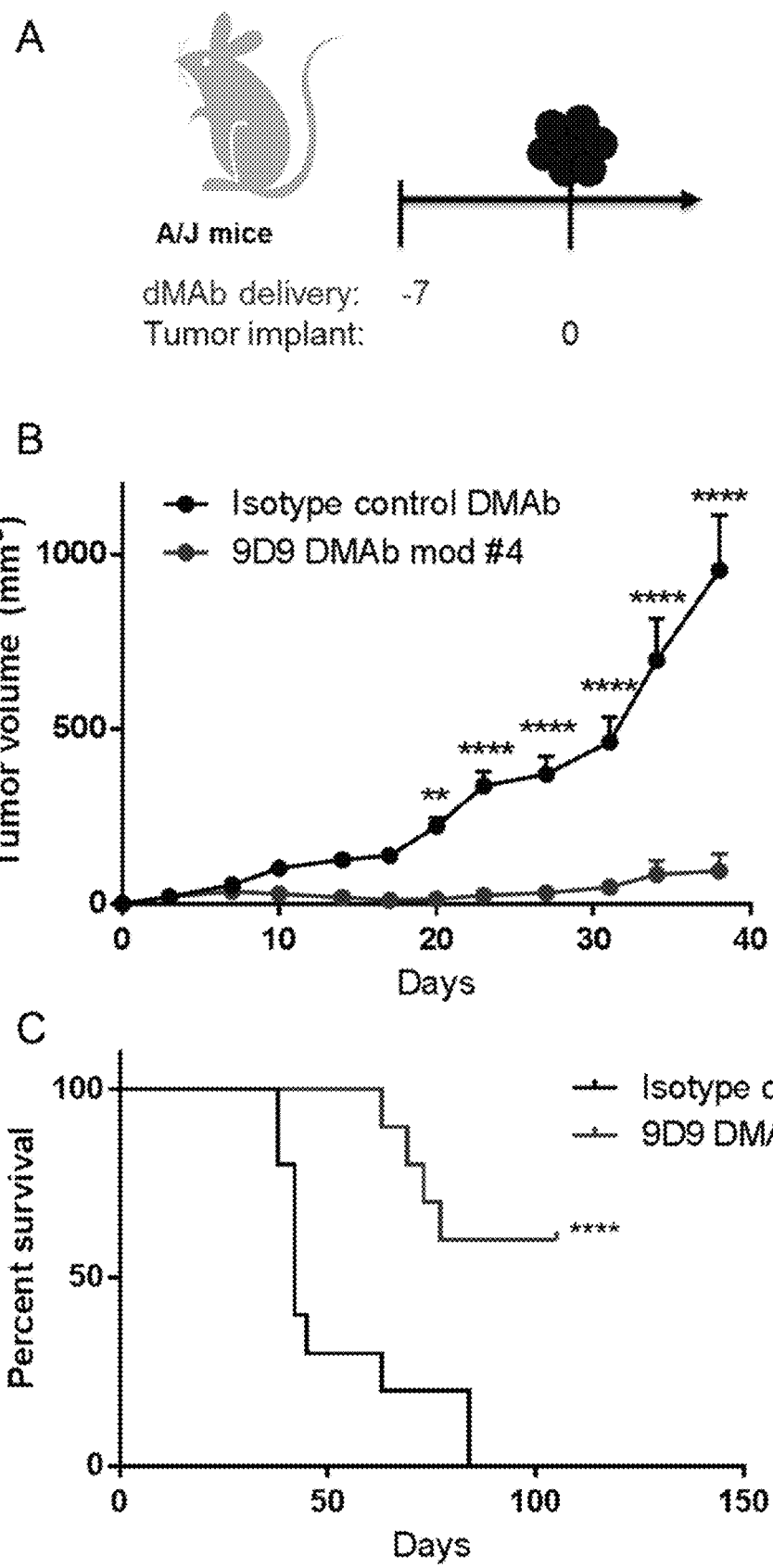
FIG. 6A through FIG. 6C, depicts exemplary experimental results demonstrating the efficacy of mouse anti-mouse CTLA-4 DMAb when delivered at an earlier time point.

Next, the highest expressing 9D9 DMAb (9D9 DMAb mod #4) was studied in mouse tumor challenge models. The Sa1N fibrosarcoma model was utilized first, which is one of the first models used to demonstrate anti-tumor immunity from CTLA-4 blockade (Leach et al., 1996, Science, 271: 1734-1736). Anti-tumor activity of the 9D9 DMAb was compared to that of the recombinant 9D9 antibody (FIG. 3A). Because DMAbs take a few days to be secreted from the muscle tissue, DMAb delivery was started 4 days earlier than recombinant 9D9. One injection of DNA (400 µg) was compared to three injections of recombinant 9D9 antibody, delivered three days apart (10 µg per injection). Similar kinetics of expression were observed (FIG. 3A, FIG. 4A,B), indicating prolonged duration of expression of the DMAb. Upon challenge with Sa1N tumor cells, both the 9D9 DMAb and the recombinant 9D9 were effective at inducing tumor clearance compared to control groups (FIG. 3B, FIG. 4C). Tumors grew in all mice initially upon implantation; however, upon DMAb delivery, 8/10 mice cleared their tumors (FIG. 3B). Upon recombinant 9D9 delivery, 9/10 mice completely cleared their tumors (FIG. 4D). Due to the immunogenic nature of this tumor, 3/10 mice in the mouse IgG control group also cleared their tumors spontaneously (FIG. 4D). To test for immunologic memory after DMAb exposure, the mice that cleared their tumors were re-challenged 6 months after the initial treatment (FIG. 5). 100% of the mice that were previously treated with either recombinant 9D9 antibody or 9D9 DMAb cleared the re-implanted tumors (FIG. 6). It is also demonstrated that earlier DMAb administration (7 days prior to tumor implantation) was also effective at inducing tumor clearance in 6/10 mice (FIG. 6A-6C). In summary, anti-CTLA4 DMAbs exhibit prolonged serum antibody levels exhibiting an injection sparing effect with similar anti-tumor activity compared to recombinant mAb.

Figures 7A, 7B, 7C, 7D, 7E:
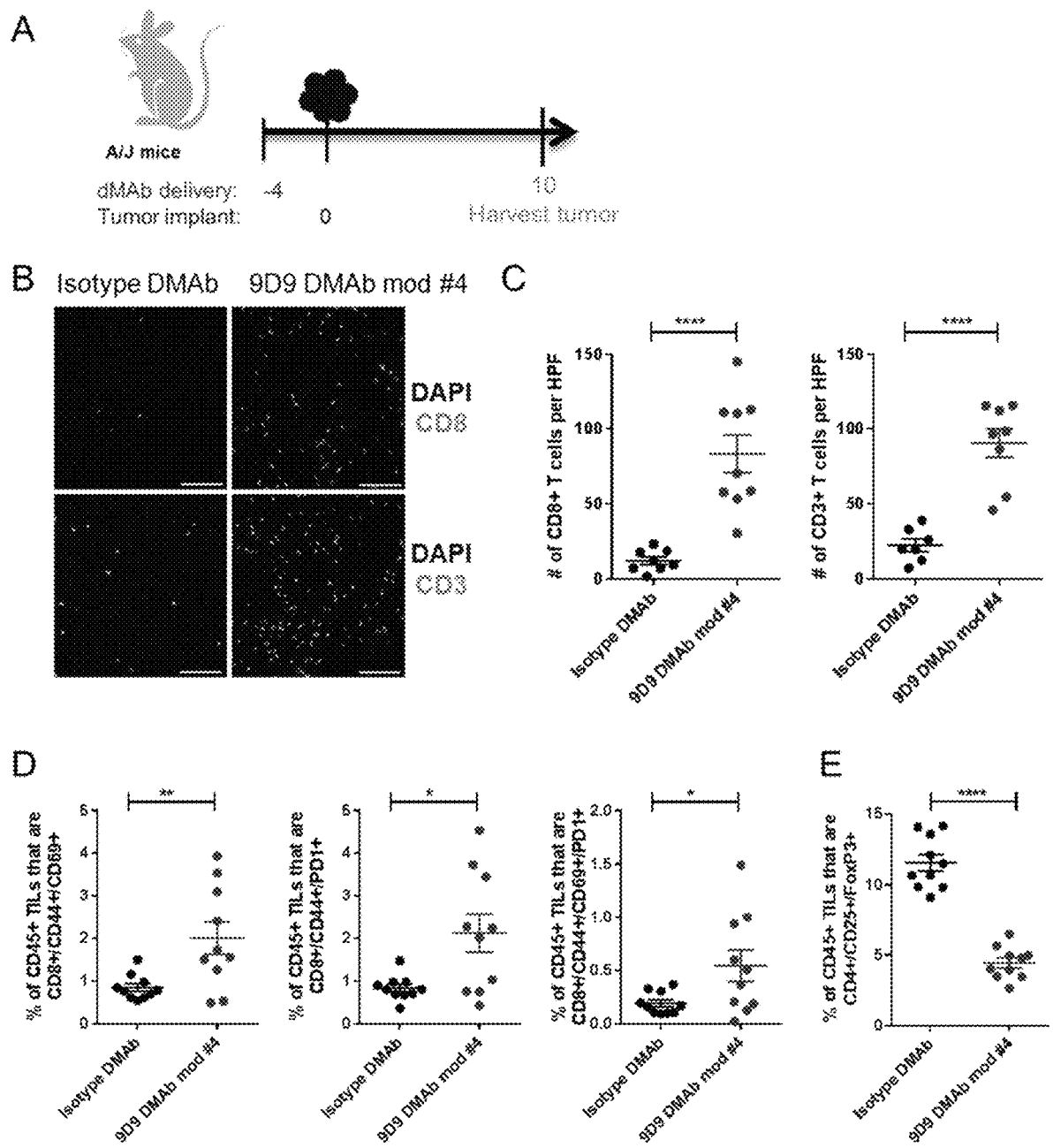

Next, the impact of 9D9 DMAb on the tumor microenvironment prior to tumor clearance at day 10 (FIG. 7A) was tested. At this early time point, tumors from both groups were similar sizes. The 9D9 DMAb induced higher levels of global lymphocyte infiltration (CD3+ cells) as well as specifically CD8+ T cell infiltration, compared to isotype control mice, indicating potent immune stimulatory capacity driven by the DMAb (FIG. 7B,C). In addition, the CD8+ T cells infiltrating the 9D9 DMAb-treated tumors expressed higher levels of activation markers, including CD44, CD69 and PD1 (FIG. 7D). Importantly, tumors treated with the 9D9 DMAb had a significantly lower proportion of regulatory T cells (CD4+/CD25+/FoxP3+) (FIG. 7E).

Next, the efficacy of this DMAb was tested in a therapeutic setting in the CT26 tumor model. For this model, DMAb administration was begun 3 days after tumor implantation (FIG. 3C). The 9D9 DMAb exhibited high expression in this mouse strain (FIG. 3C), and was effective at controlling tumor growth in this therapeutic setting, inducing tumor clearance in 8/10 mice (FIG. 3D). These results support the versatility of this DMAb platform across multiple mouse strains and tumor models.

Expression and Binding of Human Anti-Human CTLA-4 DMAbs

Figures 8A, 8B, 8C, 8D:
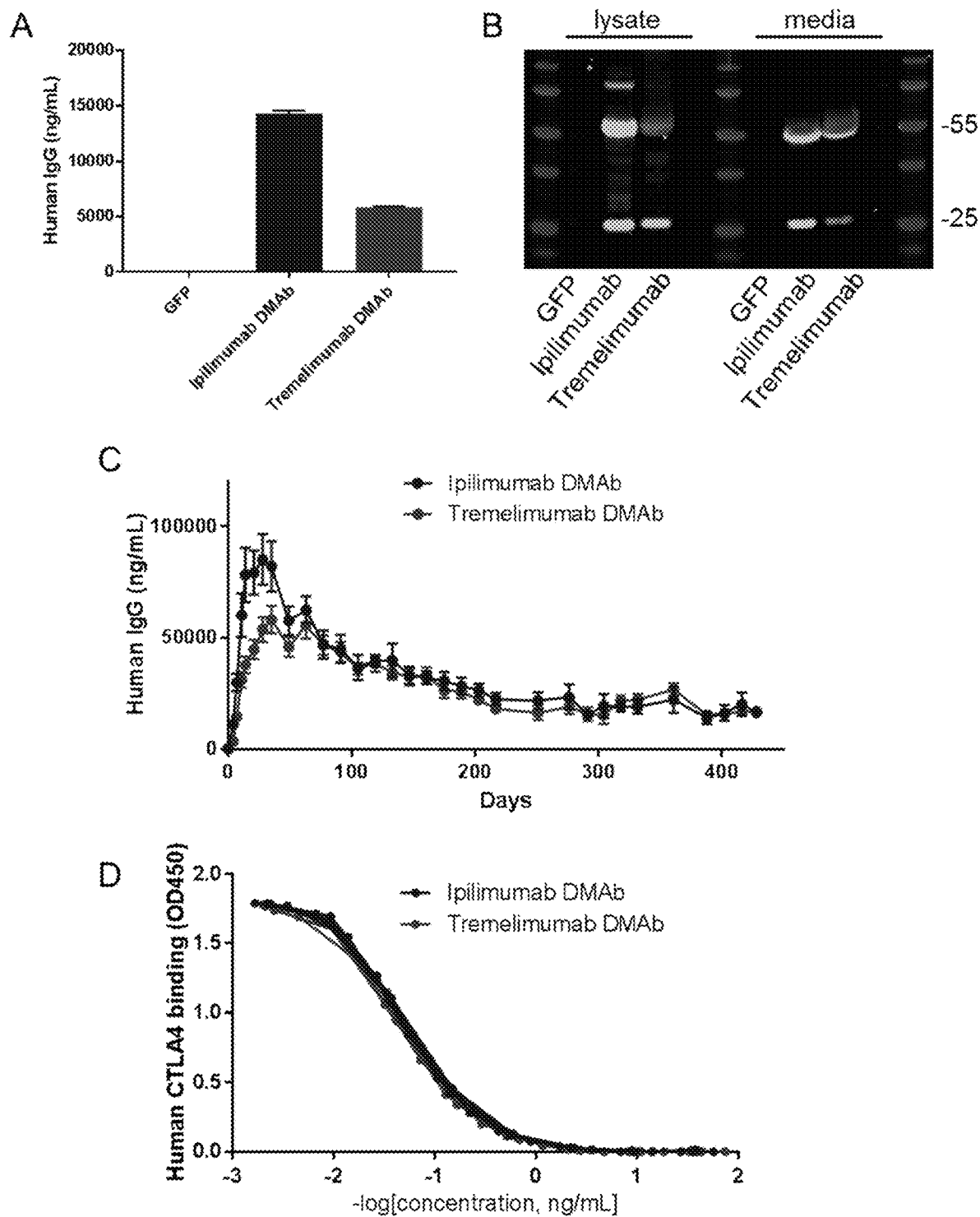
FIG. 8A through FIG. 8D, depicts exemplary experimental results demonstrating the expression and binding of human anti-human CTLA-4 DMAbs.

Next, both in vitro and in vivo production of clinically relevant ipilimumab and tremelimumab DMAbs (ipi-DMAb and treme-DMAb) was tested (FIG. 8). Both of these DMAbs were expressed and secreted at very high levels into the media of transfected cells in vitro (~14.3 µg/mL for ipi-DMAb and ~5.8 µg/mL for treme-DMAb, FIG. 8A). In addition, both heavy and light chains were clearly visible in both lysate and media by western blot (FIG. 8B).

Figure 9:
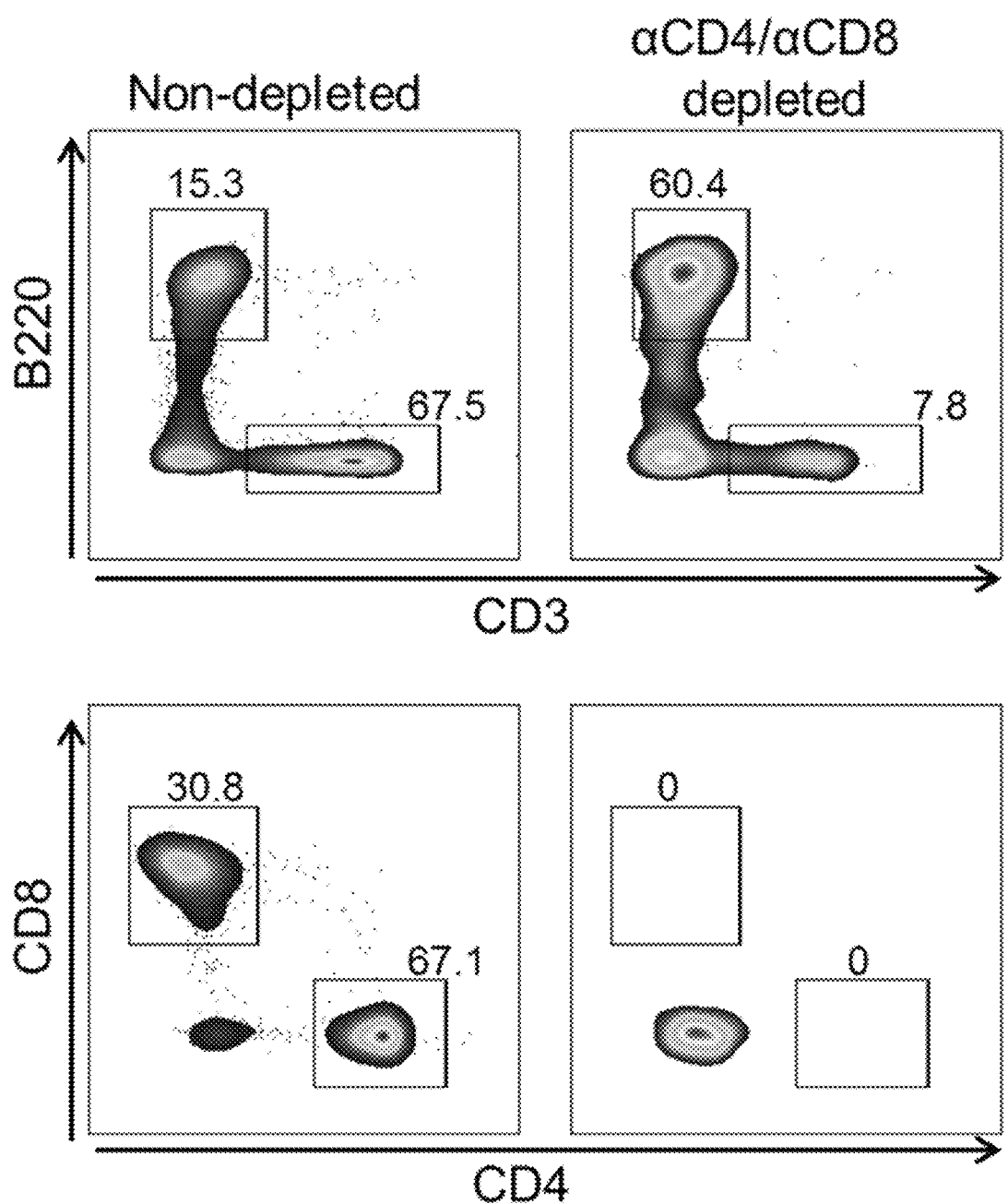
FIG. 9 depicts exemplary experimental results demonstrating the efficiency of CD4 and CD8 depletion antibodies.

Dosing of 400 µg of formulated DNA in the tibialis anterior and quadriceps muscles of Balb/c mice demonstrated robust expression of both DMAbs, with potent peak expression levels of ~85 µg/mL for ipi-DMAb and ~58 µg/mL for treme-DMAb (FIG. 8C). These studies were done in mice depleted of CD4 and CD8 T cells to eliminate the anti-human immune response (FIG. 9). Both DMAbs produced mAb for prolonged periods of over one year (FIG. 8C). Importantly, the DMAb harbored in the serum of the treated animals bound robustly to human CTLA-4 by ELISA (FIG. 8D).

Functionality of Human Anti-Human CTLA-4 DMAbs

Figures 10A, 10B, 10C, 10D:
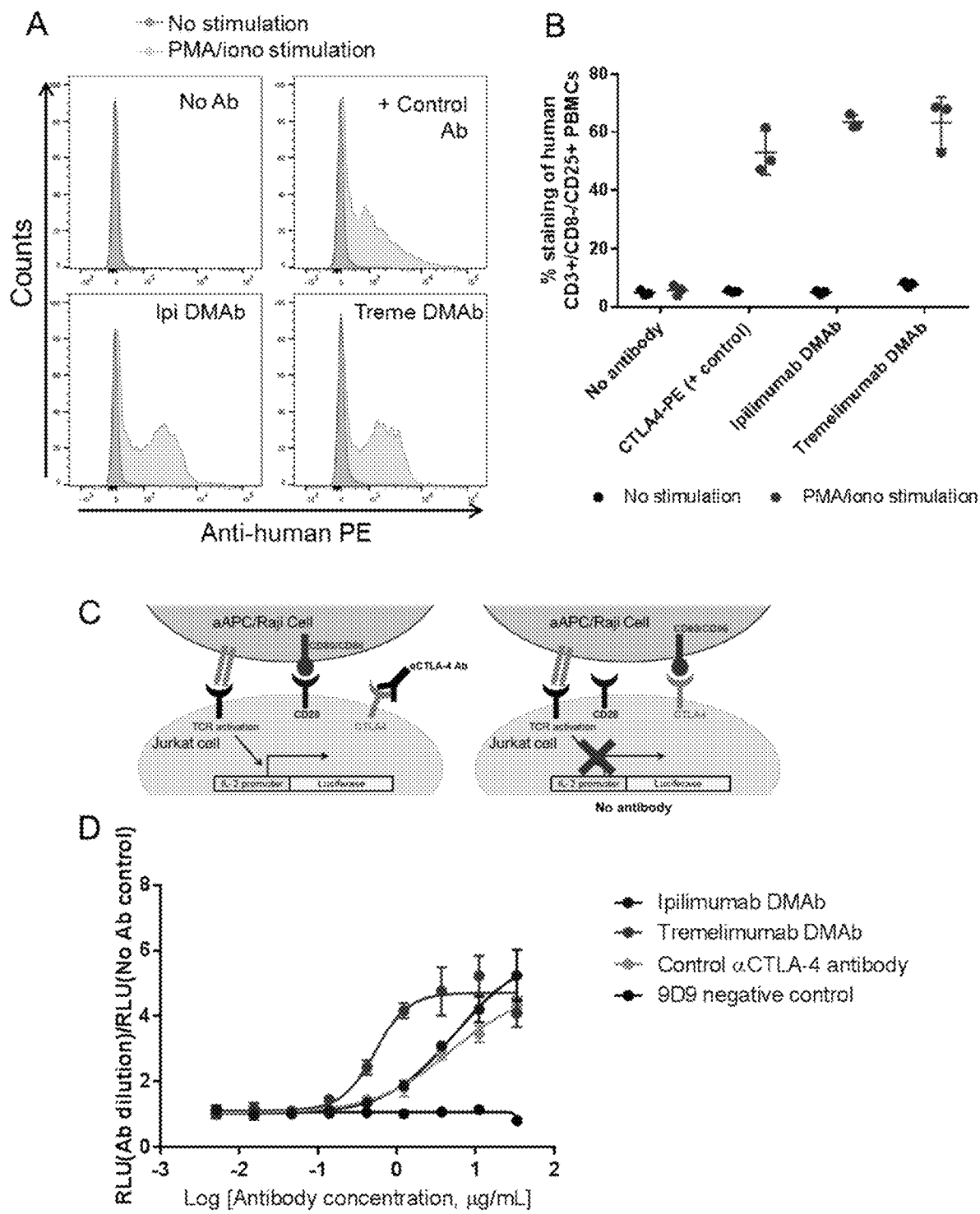
FIG. 10A through FIG. 10D, depicts exemplary experimental results demonstrating the functionality of human anti-human CTLA-4 DMAbs.

Functionality of the ipi-DMAb and treme-DMAbs was assessed using in vitro human T cell assays (FIG. 10). Peripheral blood mononuclear cells (PBMCs) were isolated from three healthy donors, and stimulated with PMA/ionomycin to induce CTLA-4 surface expression on regulatory T cells (FIG. 10A) (Jago et al., 2004, Clin Exp Immunol, 136:463-471). Because CD4 surface expression is down-regulated upon stimulation with PMA/ionomycin, regulatory T cells (Tregs) were classified as CD3+, CD8− and CD25+ PBMCs. Similar to the positive control anti-human CTLA-4 antibody, in vivo produced ipi-DMAb and treme-DMAb efficiently stained stimulated Tregs, but not unstimulated Tregs (FIG. 10A,B).

Figure 11:
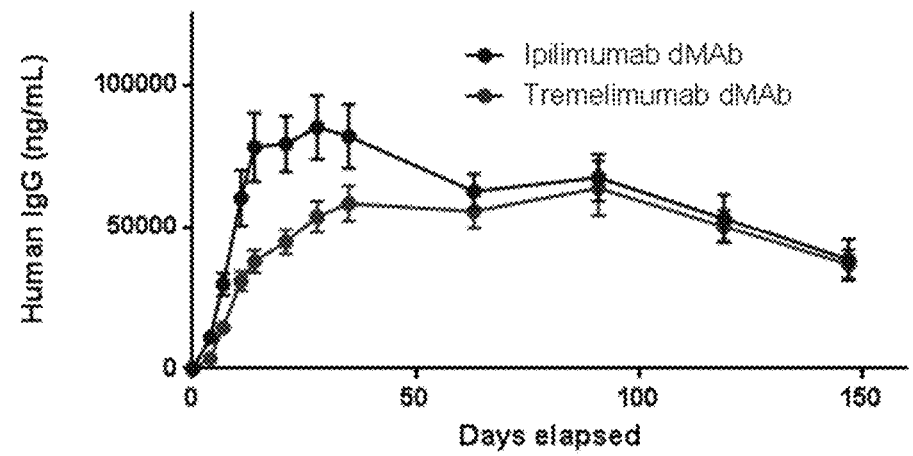
FIG. 11 depicts results from example experiments, demonstrating delivery of anti-human CTLA-4 using DNA (in viro expression and binding).
Figure 11:
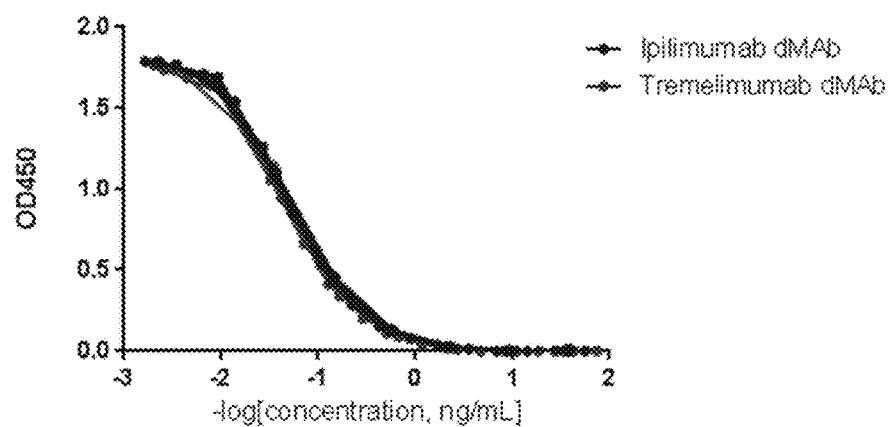

A functional T cell activation assay was utilized to test the ability of the DMAbs to induce T cell activation in vitro. For this assay, aAPC/Raji cells were coincubated with Jurkat cells that were transduced with a construct expressing luciferase off of the IL-2 promoter (FIG. 10C). Upon efficient blockade of the CTLA-4/CD80/CD86 interaction, these Jurkat cells can be efficiently activated and express luciferase (FIG. 10C). It was found that ipi-DMAb, treme-DMAb and the positive control αCTLA-4 antibody induced luciferase expression in a dose-dependent manner (FIG. 10D). As expected, the negative control antibody (9D9) did not induce luciferase expression (FIG. 10D). Interestingly, the treme-DMAb induced luciferase expression at lower concentrations compared to the ipi-DMAb, potentially indicating more potent blocking function (FIG. 10D). Together, these results demonstrate that anti-CTLA-4 antibodies produced by DNA plasmids in vivo are functional. The functionality of these in vivo expressed antibodies was confirmed as well (FIG. 11).

Example 2

Synergy of mTERT DNA Vaccine with Anti-CTLA-4 Checkpoint Inhibitor

Figure 12:
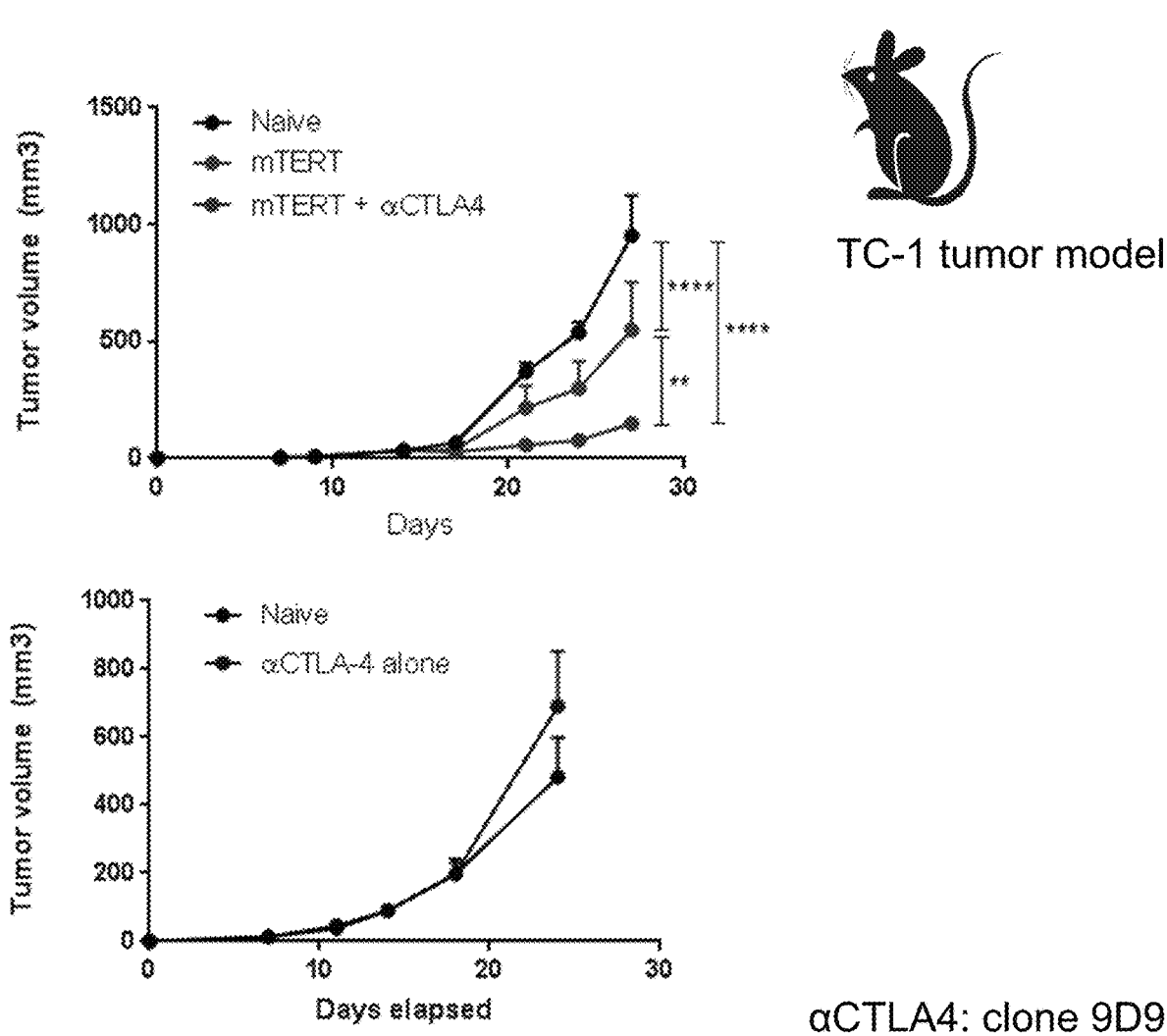
FIG. 12 depicts results from example experiments, demonstrating synergy of mTERT DNA vaccine+αCTLA-4 recombinant antibody.

The TC-1 mouse tumor model was used to investigate potential synergy between an mTERT DNA vaccine and an anti-CTLA-4 recombinant antibody. As depicted in FIG. 12, tumor volume was reduced in cohorts that received mTERT DNA vaccine in combination with recombinant anti-CTLA-4 antibody (clone 9D9), compared to Naïve mice or mice that received mTERT DNA vaccine alone.

Figure 13:
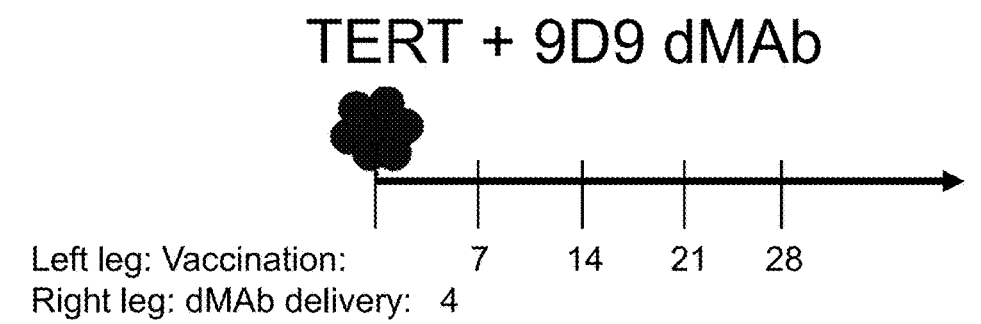
FIG. 13 depicts results from example experiments, demonstrating synergy of mTERT DNA vaccine+αCTLA-4 DMAb.
Figure 13:
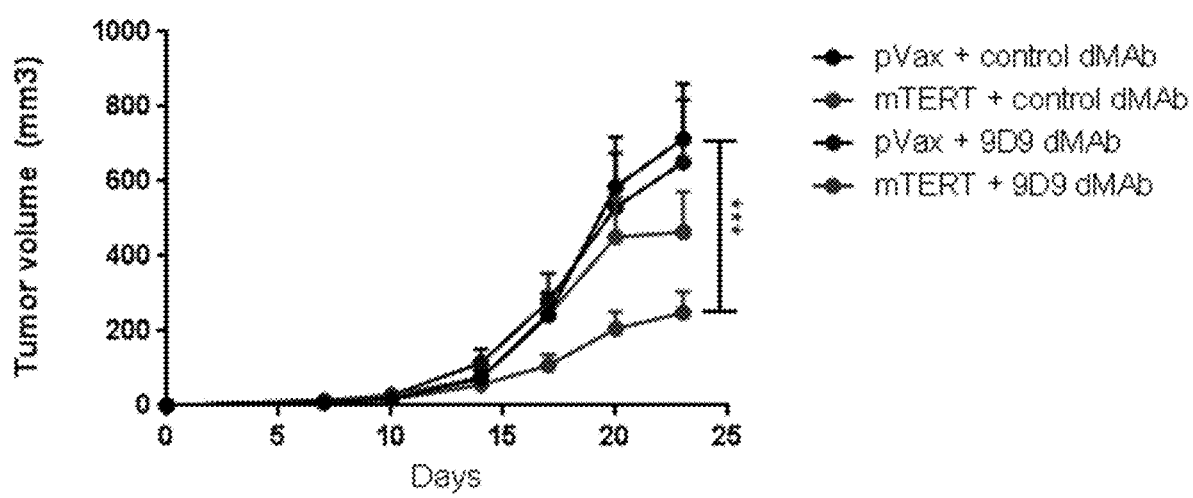

In another experiment, the TC-1 mouse tumor model was used to investigate potential synergy between an mTERT DNA vaccine and an anti-CTLA-4 DMAb. As depicted in FIG. 13, tumor volume was reduced in cohorts that received mTERT DNA vaccine in combination with 9D9, compared to all other groups (pVax+control DMAb, mTERT+control DMAb, pVax+9D9 DMAb).

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition for generating one or more anti-CTLA-4 antibodies or antigen binding fragments thereof in a subject, comprising one or more nucleic acid molecules encoding one or more anti-CTLA-4 antibodies or antigen binding fragments thereof, comprising a nucleotide sequence encoding an amino acid sequence selected from the group of SEQ ID NOs: 1, 2, 3, and 4, without the leader sequence.

2. The composition of claim 1, comprising a nucleotide sequence encoding a cleavage domain.

3. The composition of claim 1, comprising a nucleotide sequence encoding a variable heavy chain region and a variable light chain region of the antibody.

4. The composition of claim 1, comprising a nucleotide sequence encoding a polypeptide comprising a constant heavy chain region and a polypeptide comprising a constant light chain region.

5. The composition of claim 1, comprising a nucleotide sequence encoding a polypeptide comprising a variable heavy chain region; a constant heavy chain region; a cleavage domain; a variable light chain region; and a constant light chain region.

6. The composition of claim 1, comprising a nucleotide sequence having at least about 80% identity over the entire length of at least one nucleotide sequence selected from the group of SEQ ID NOs: 7, 8, 9, and 10, without the leader sequence.

7. The composition of claim 1, wherein the one or more nucleic acid molecules are engineered to be in an expression vector.

8. The composition of claim 7, further comprising a pharmaceutically acceptable excipient.

9. The composition of claim 1, further comprising a nucleotide sequence encoding an antigen.

10. The composition of claim 9, wherein the antigen is a cancer antigen.

11. A method of treating a cancer in a subject, the method comprising administering to the subject the composition of claim 1.

12. The method of claim 11, wherein administering the composition comprises an electroporating step.

13. A method for increasing an immune response in a subject in need thereof, the method comprising administering the composition of claim 1 to the subject.

14. The method of claim 13, further comprising a subsequent step of administering to the subject a composition comprising an antigen.

15. The method of claim 14, wherein administering comprises an electroporation step at the site of administration.

* * * * *

SEQUENCE LISTING

<160> NUMBER OF SEQ ID NOS: 17

<210> SEQ ID NO 1
<211> LENGTH: 740
<212> TYPE: PRT
<213> ORGANISM: Artificial Sequence
<220> FEATURE:
<223> OTHER INFORMATION: Chemically synthesized, 9D9 DMAb original

<400> SEQUENCE: 1

```
Met Asp Trp Thr Trp Arg Ile Leu Phe Leu Val Ala Ala Thr Gly
1               5                   10                  15

Thr His Ala Glu Ala Lys Leu Gln Glu Ser Gly Pro Val Leu Val Lys
            20                  25                  30

Pro Gly Ala Ser Val Lys Met Ser Cys Lys Ala Ser Gly Tyr Thr Phe
        35                  40                  45

Thr Asp Tyr Tyr Met Asn Trp Val Lys Gln Ser His Gly Lys Ser Leu
    50                  55                  60

Glu Trp Ile Gly Val Ile Asn Pro Tyr Asn Gly Asp Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Asn Ser Leu Thr Ser Glu Asp Ser Ala Val
            100                 105                 110

Tyr Tyr Cys Ala Arg Tyr Tyr Gly Ser Trp Phe Ala Tyr Trp Gly Gln
        115                 120                 125

Gly Thr Leu Ile Thr Val Ser Thr Ala Lys Thr Thr Pro Pro Ser Val
    130                 135                 140

Tyr Pro Leu Ala Pro Gly Cys Gly Asp Thr Thr Gly Ser Ser Val Thr
145                 150                 155                 160

Leu Gly Cys Leu Val Lys Gly Tyr Phe Pro Glu Ser Val Thr Val Thr
                165                 170                 175

Trp Asn Ser Gly Ser Leu Ser Ser Val His Thr Phe Pro Ala Leu
            180                 185                 190

Leu Gln Ser Gly Leu Tyr Thr Met Ser Ser Ser Val Thr Val Pro Ser
        195                 200                 205

Ser Thr Trp Pro Ser Gln Thr Val Thr Cys Ser Val Ala His Pro Ala
    210                 215                 220

Ser Ser Thr Thr Val Asp Lys Lys Leu Glu Pro Ser Gly Pro Ile Ser
225                 230                 235                 240

Thr Ile Asn Pro Cys Pro Pro Cys Lys Glu Cys His Lys Cys Pro Ala
                245                 250                 255

Pro Asn Leu Glu Gly Gly Pro Ser Val Phe Ile Phe Pro Pro Asn Ile
            260                 265                 270

Lys Asp Val Leu Met Ile Ser Leu Thr Pro Lys Val Thr Cys Val Val
        275                 280                 285

Val Asp Val Ser Glu Asp Asp Pro Asp Val Gln Ile Ser Trp Phe Val
    290                 295                 300

Asn Asn Val Glu Val His Thr Ala Gln Thr Gln Thr His Arg Glu Asp
305                 310                 315                 320

Tyr Asn Ser Thr Ile Arg Val Val Ser Thr Leu Pro Ile Gln His Gln
                325                 330                 335

Asp Trp Met Ser Gly Lys Glu Phe Lys Cys Lys Val Asn Asn Lys Asp
            340                 345                 350
```

```
Leu Pro Ser Pro Ile Glu Arg Thr Ile Ser Lys Ile Lys Gly Leu Val
            355                 360                 365

Arg Ala Pro Gln Val Tyr Ile Leu Pro Pro Ala Glu Gln Leu Ser
370                 375                 380

Arg Lys Asp Val Ser Leu Thr Cys Leu Val Val Gly Phe Asn Pro Gly
385                 390                 395                 400

Asp Ile Ser Val Glu Trp Thr Ser Asn Gly His Thr Glu Glu Asn Tyr
                405                 410                 415

Lys Asp Thr Ala Pro Val Leu Asp Ser Asp Gly Ser Tyr Phe Ile Tyr
                420                 425                 430

Ser Lys Leu Asn Met Lys Thr Ser Lys Trp Glu Lys Thr Asp Ser Phe
            435                 440                 445

Ser Cys Asn Val Arg His Glu Gly Leu Lys Asn Tyr Tyr Leu Lys Lys
            450                 455                 460

Thr Ile Ser Arg Ser Pro Gly Lys Arg Gly Lys Arg Arg Ser Gly
465                 470                 475                 480

Ser Gly Ala Thr Asn Phe Ser Leu Leu Lys Gln Ala Gly Asp Val Glu
                485                 490                 495

Glu Asn Pro Gly Pro Met Val Leu Gln Thr Gln Val Phe Ile Ser Leu
            500                 505                 510

Leu Leu Trp Ile Ser Gly Ala Tyr Gly Asp Ile Val Met Thr Gln Thr
            515                 520                 525

Thr Leu Ser Leu Pro Val Ser Leu Gly Asp Gln Ala Ser Ile Ser Cys
            530                 535                 540

Arg Ser Ser Gln Ser Ile Val His Ser Asn Gly Asn Thr Tyr Leu Glu
545                 550                 555                 560

Trp Tyr Leu Gln Lys Pro Gly Gln Ser Pro Lys Leu Leu Ile Tyr Lys
                565                 570                 575

Val Ser Asn Arg Phe Ser Gly Val Pro Asp Arg Phe Ser Gly Ser Gly
                580                 585                 590

Ser Gly Thr Asp Phe Thr Leu Lys Ile Ser Arg Val Glu Ala Glu Asp
            595                 600                 605

Leu Gly Val Tyr Tyr Cys Phe Gln Gly Ser His Val Pro Tyr Thr Phe
            610                 615                 620

Gly Gly Gly Thr Lys Leu Glu Ile Lys Arg Ala Asp Ala Ala Pro Thr
625                 630                 635                 640

Val Ser Ile Phe Pro Pro Ser Ser Glu Gln Leu Thr Ser Gly Gly Ala
                645                 650                 655

Ser Val Val Cys Phe Leu Asn Asn Phe Tyr Pro Lys Asp Ile Asn Val
                660                 665                 670

Lys Trp Lys Ile Asp Gly Ser Glu Arg Gln Asn Gly Val Leu Asn Ser
            675                 680                 685

Trp Thr Asp Gln Asp Ser Lys Asp Ser Thr Tyr Ser Met Ser Ser Thr
690                 695                 700

Leu Thr Leu Thr Lys Asp Glu Tyr Glu Arg His Asn Ser Tyr Thr Cys
705                 710                 715                 720

Glu Ala Thr His Lys Thr Ser Thr Ser Pro Ile Val Lys Ser Phe Asn
                725                 730                 735

Arg Asn Glu Cys
            740

<210> SEQ ID NO 2
<211> LENGTH: 740
```

```
<212> TYPE: PRT
<213> ORGANISM: Artificial Sequence
<220> FEATURE:
<223> OTHER INFORMATION: Chemically synthesized, 9D9 DMAb mod #2

<400> SEQUENCE: 2

Met Asp Trp Thr Trp Arg Ile Leu Phe Leu Val Ala Ala Ala Thr Gly
1               5                   10                  15

Thr His Ala Glu Ala Lys Leu Gln Glu Ser Gly Pro Val Leu Val Lys
            20                  25                  30

Pro Gly Ala Ser Val Lys Met Ser Cys Lys Ala Ser Gly Tyr Thr Phe
        35                  40                  45

Thr Asp Tyr Tyr Met Asn Trp Val Lys Gln Ser His Gly Lys Ser Leu
    50                  55                  60

Glu Trp Ile Gly Val Ile Asn Pro Tyr Asn Gly Asp Thr Ser Tyr Asn
65                  70                  75                  80

Gln Lys Phe Lys Gly Lys Ala Thr Leu Thr Val Asp Lys Ser Ser Ser
            85                  90                  95

Thr Ala Tyr Met Glu Leu Asn Ser Leu Thr Ser Glu Asp Ser Ala Val
        100                 105                 110

Tyr Tyr Cys Ala Arg Tyr Tyr Gly Ser Trp Phe Ala Tyr Trp Gly Gln
    115                 120                 125

Gly Thr Leu Val Thr Val Ser Ser Ala Lys Thr Thr Pro Pro Ser Val
130                 135                 140

Tyr Pro Leu Ala Pro Gly Cys Gly Asp Thr Thr Gly Ser Ser Val Thr
145                 150                 155                 160

Leu Gly Cys Leu Val Lys Gly Tyr Phe Pro Glu Ser Val Thr Val Thr
            165                 170                 175

Trp Asn Ser Gly Ser Leu Ser Ser Val His Thr Phe Pro Ala Leu
        180                 185                 190

Leu Gln Ser Gly Leu Tyr Thr Met Ser Ser Ser Val Thr Val Pro Ser
    195                 200                 205

Ser Thr Trp Pro Ser Gln Thr Val Thr Cys Ser Val Ala His Pro Ala
210                 215                 220

Ser Ser Thr Thr Val Asp Lys Lys Leu Glu Pro Ser Gly Pro Ile Ser
225                 230                 235                 240

Thr Ile Asn Pro Cys Pro Pro Cys Lys Glu Cys His Lys Cys Pro Ala
            245                 250                 255

Pro Asn Leu Glu Gly Gly Pro Ser Val Phe Ile Phe Pro Pro Asn Ile
        260                 265                 270

Lys Asp Val Leu Met Ile Ser Leu Thr Pro Lys Val Thr Cys Val Val
    275                 280                 285

Val Asp Val Ser Glu Asp Asp Pro Asp Val Gln Ile Ser Trp Phe Val
290                 295                 300

Asn Asn Val Glu Val His Thr Ala Gln Thr Gln Thr His Arg Glu Asp
305                 310                 315                 320

Tyr Asn Ser Thr Ile Arg Val Val Ser Thr Leu Pro Ile Gln His Gln
            325                 330                 335

Asp Trp Met Ser Gly Lys Glu Phe Lys Cys Lys Val Asn Asn Lys Asp
        340                 345                 350

Leu Pro Ser Pro Ile Glu Arg Thr Ile Ser Lys Ile Lys Gly Leu Val
    355                 360                 365

Arg Ala Pro Gln Val Tyr Ile Leu Pro Pro Ala Glu Gln Leu Ser
370                 375                 380
```

```
Arg Lys Asp Val Ser Leu Thr Cys Leu Val Val Gly Phe Asn Pro Gly
385                 390                 395                 400

Asp Ile Ser Val Glu Trp Thr Ser Asn Gly His Thr Glu Glu Asn Tyr
            405                 410                 415

Lys Asp Thr Ala Pro Val Leu Asp Ser Asp Gly Ser Tyr Phe Ile Tyr
            420                 425                 430

Ser Lys Leu Asn Met Lys Thr Ser Lys Trp Glu Lys Thr Asp Ser Phe
        435                 440                 445

Ser Cys Asn Val Arg His Glu Gly Leu Lys Asn Tyr Tyr Leu Lys Lys
    450                 455                 460

Thr Ile Ser Arg Ser Pro Gly Lys Arg Gly Lys Arg Arg Ser Gly
465                 470                 475                 480

Ser Gly Ala Thr Asn Phe Ser Leu Leu Lys Gln Ala Gly Asp Val Glu
                485                 490                 495

Glu Asn Pro Gly Pro Met Val Leu Gln Thr Gln Val Phe Ile Ser Leu
            500                 505                 510

Leu Leu Trp Ile Ser Gly Ala Tyr Gly Asp Ile Val Met Thr Gln Thr
        515                 520                 525

Thr Leu Ser Leu Pro Val Ser Leu Gly Asp Gln Ala Ser Ile Ser Cys
530                 535                 540

Arg Ser Ser Gln Ser Ile Val His Ser Asn Gly Asn Thr Tyr Leu Glu
545                 550                 555                 560

Trp Tyr Leu Gln Lys Pro Gly Gln Ser Pro Lys Leu Leu Ile Tyr Lys
                565                 570                 575

Val Ser Asn Arg Phe Ser Gly Val Pro Asp Arg Phe Ser Gly Ser Gly
            580                 585                 590

Ser Gly Thr Asp Phe Thr Leu Lys Ile Ser Arg Val Glu Ala Glu Asp
        595                 600                 605

Leu Gly Val Tyr Tyr Cys Phe Gln Gly Ser His Val Pro Tyr Thr Phe
    610                 615                 620

Gly Gly Gly Thr Lys Leu Glu Ile Lys Arg Ala Asp Ala Ala Pro Thr
625                 630                 635                 640

Val Ser Ile Phe Pro Pro Ser Ser Glu Gln Leu Thr Ser Gly Gly Ala
                645                 650                 655

Ser Val Val Cys Phe Leu Asn Asn Phe Tyr Pro Lys Asp Ile Asn Val
            660                 665                 670

Lys Trp Lys Ile Asp Gly Ser Glu Arg Gln Asn Gly Val Leu Asn Ser
        675                 680                 685

Trp Thr Asp Gln Asp Ser Lys Asp Ser Thr Tyr Ser Met Ser Ser Thr
690                 695                 700

Leu Thr Leu Thr Lys Asp Glu Tyr Glu Arg His Asn Ser Tyr Thr Cys
705                 710                 715                 720

Glu Ala Thr His Lys Thr Ser Thr Ser Pro Ile Val Lys Ser Phe Asn
                725                 730                 735

Arg Asn Glu Cys
            740

<210> SEQ ID NO 3
<211> LENGTH: 740
<212> TYPE: PRT
<213> ORGANISM: Artificial Sequence
<220> FEATURE:
<223> OTHER INFORMATION: Chemically synthesized, 9D9 DMAb mod #3
```

-continued

<400> SEQUENCE: 3

Met Asp Trp Thr Trp Arg Ile Leu Phe Leu Val Ala Ala Thr Gly
1               5                   10                  15

Thr His Ala Glu Val Gln Leu Gln Gln Ser Gly Pro Val Leu Val Lys
            20                  25                  30

Pro Gly Ala Ser Val Lys Met Ser Cys Lys Ala Ser Gly Tyr Thr Phe
        35                  40                  45

Thr Asp Tyr Tyr Met Asn Trp Val Lys Gln Ser His Gly Lys Ser Leu
    50                  55                  60

Glu Trp Ile Gly Val Ile Asn Pro Tyr Asn Gly Asp Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Asn Ser Leu Thr Ser Glu Asp Ser Ala Val
            100                 105                 110

Tyr Tyr Cys Ala Arg Tyr Gly Ser Trp Phe Ala Tyr Trp Gly Gln
        115                 120                 125

Gly Thr Leu Ile Thr Val Ser Thr Ala Lys Thr Thr Pro Pro Ser Val
130                 135                 140

Tyr Pro Leu Ala Pro Gly Cys Gly Asp Thr Thr Gly Ser Ser Val Thr
145                 150                 155                 160

Leu Gly Cys Leu Val Lys Gly Tyr Phe Pro Glu Ser Val Thr Val Thr
                165                 170                 175

Trp Asn Ser Gly Ser Leu Ser Ser Ser Val His Thr Phe Pro Ala Leu
            180                 185                 190

Leu Gln Ser Gly Leu Tyr Thr Met Ser Ser Ser Val Thr Val Pro Ser
        195                 200                 205

Ser Thr Trp Pro Ser Gln Thr Val Thr Cys Ser Val Ala His Pro Ala
    210                 215                 220

Ser Ser Thr Thr Val Asp Lys Lys Leu Glu Pro Ser Gly Pro Ile Ser
225                 230                 235                 240

Thr Ile Asn Pro Cys Pro Pro Cys Lys Glu Cys His Lys Cys Pro Ala
                245                 250                 255

Pro Asn Leu Glu Gly Gly Pro Ser Val Phe Ile Phe Pro Pro Asn Ile
            260                 265                 270

Lys Asp Val Leu Met Ile Ser Leu Thr Pro Lys Val Thr Cys Val Val
        275                 280                 285

Val Asp Val Ser Glu Asp Asp Pro Asp Val Gln Ile Ser Trp Phe Val
    290                 295                 300

Asn Asn Val Glu Val His Thr Ala Gln Thr Gln Thr His Arg Glu Asp
305                 310                 315                 320

Tyr Asn Ser Thr Ile Arg Val Val Ser Thr Leu Pro Ile Gln His Gln
                325                 330                 335

Asp Trp Met Ser Gly Lys Glu Phe Lys Cys Lys Val Asn Asn Lys Asp
            340                 345                 350

Leu Pro Ser Pro Ile Glu Arg Thr Ile Ser Lys Ile Lys Gly Leu Val
        355                 360                 365

Arg Ala Pro Gln Val Tyr Ile Leu Pro Pro Ala Glu Gln Leu Ser
    370                 375                 380

Arg Lys Asp Val Ser Leu Thr Cys Leu Val Val Gly Phe Asn Pro Gly
385                 390                 395                 400

```
Asp Ile Ser Val Glu Trp Thr Ser Asn Gly His Thr Glu Asn Tyr
            405                 410                 415

Lys Asp Thr Ala Pro Val Leu Asp Ser Asp Gly Ser Tyr Phe Ile Tyr
            420                 425                 430

Ser Lys Leu Asn Met Lys Thr Ser Lys Trp Glu Lys Thr Asp Ser Phe
            435                 440                 445

Ser Cys Asn Val Arg His Glu Gly Leu Lys Asn Tyr Tyr Leu Lys Lys
450                 455                 460

Thr Ile Ser Arg Ser Pro Gly Lys Arg Gly Arg Lys Arg Arg Ser Gly
465                 470                 475                 480

Ser Gly Ala Thr Asn Phe Ser Leu Leu Lys Gln Ala Gly Asp Val Glu
            485                 490                 495

Glu Asn Pro Gly Pro Met Val Leu Gln Thr Gln Val Phe Ile Ser Leu
            500                 505                 510

Leu Leu Trp Ile Ser Gly Ala Tyr Gly Asp Ile Val Met Thr Gln Thr
            515                 520                 525

Thr Leu Ser Leu Pro Val Ser Leu Gly Asp Gln Ala Ser Ile Ser Cys
            530                 535                 540

Arg Ser Ser Gln Ser Ile Val His Ser Asn Gly Asn Thr Tyr Leu Glu
545                 550                 555                 560

Trp Tyr Leu Gln Lys Pro Gly Gln Ser Pro Lys Leu Leu Ile Tyr Lys
            565                 570                 575

Val Ser Asn Arg Phe Ser Gly Val Pro Asp Arg Phe Ser Gly Ser Gly
            580                 585                 590

Ser Gly Thr Asp Phe Thr Leu Lys Ile Ser Arg Val Glu Ala Glu Asp
            595                 600                 605

Leu Gly Val Tyr Tyr Cys Phe Gln Gly Ser His Val Pro Tyr Thr Phe
            610                 615                 620

Gly Gly Gly Thr Lys Leu Glu Ile Lys Arg Ala Asp Ala Ala Pro Thr
625                 630                 635                 640

Val Ser Ile Phe Pro Pro Ser Ser Glu Gln Leu Thr Ser Gly Gly Ala
            645                 650                 655

Ser Val Val Cys Phe Leu Asn Asn Phe Tyr Pro Lys Asp Ile Asn Val
            660                 665                 670

Lys Trp Lys Ile Asp Gly Ser Glu Arg Gln Asn Gly Val Leu Asn Ser
            675                 680                 685

Trp Thr Asp Gln Asp Ser Lys Asp Ser Thr Tyr Ser Met Ser Ser Thr
            690                 695                 700

Leu Thr Leu Thr Lys Asp Glu Tyr Glu Arg His Asn Ser Tyr Thr Cys
705                 710                 715                 720

Glu Ala Thr His Lys Thr Ser Thr Ser Pro Ile Val Lys Ser Phe Asn
            725                 730                 735

Arg Asn Glu Cys
            740

<210> SEQ ID NO 4
<211> LENGTH: 740
<212> TYPE: PRT
<213> ORGANISM: Artificial Sequence
<220> FEATURE:
<223> OTHER INFORMATION: Chemically synthesized, 9D9 DMAb mod #4

<400> SEQUENCE: 4

Met Asp Trp Thr Trp Arg Ile Leu Phe Leu Val Ala Ala Ala Thr Gly
1               5                   10                  15
```

```
Thr His Ala Glu Val Gln Leu Gln Gln Ser Gly Pro Val Leu Val Lys
            20                  25                  30

Pro Gly Ala Ser Val Lys Met Ser Cys Lys Ala Ser Gly Tyr Thr Phe
        35                  40                  45

Thr Asp Tyr Tyr Met Asn Trp Val Lys Gln Ser His Gly Lys Ser Leu
50                  55                  60

Glu Trp Ile Gly Val Ile Asn Pro Tyr Asn Gly Asp Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Asn Ser Leu Thr Ser Glu Asp Ser Ala Val
            100                 105                 110

Tyr Tyr Cys Ala Arg Tyr Tyr Gly Ser Trp Phe Ala Tyr Trp Gly Gln
        115                 120                 125

Gly Thr Leu Val Thr Val Ser Ser Ala Lys Thr Thr Pro Pro Ser Val
    130                 135                 140

Tyr Pro Leu Ala Pro Gly Cys Gly Asp Thr Thr Gly Ser Ser Val Thr
145                 150                 155                 160

Leu Gly Cys Leu Val Lys Gly Tyr Phe Pro Glu Ser Val Thr Val Thr
                165                 170                 175

Trp Asn Ser Gly Ser Leu Ser Ser Val His Thr Phe Pro Ala Leu
            180                 185                 190

Leu Gln Ser Gly Leu Tyr Thr Met Ser Ser Val Thr Val Pro Ser
        195                 200                 205

Ser Thr Trp Pro Ser Gln Thr Val Thr Cys Ser Val Ala His Pro Ala
    210                 215                 220

Ser Ser Thr Thr Val Asp Lys Lys Leu Glu Pro Ser Gly Pro Ile Ser
225                 230                 235                 240

Thr Ile Asn Pro Cys Pro Pro Cys Lys Glu Cys His Lys Cys Pro Ala
                245                 250                 255

Pro Asn Leu Glu Gly Gly Pro Ser Val Phe Ile Phe Pro Pro Asn Ile
            260                 265                 270

Lys Asp Val Leu Met Ile Ser Leu Thr Pro Lys Val Thr Cys Val Val
        275                 280                 285

Val Asp Val Ser Glu Asp Asp Pro Asp Val Gln Ile Ser Trp Phe Val
    290                 295                 300

Asn Asn Val Glu Val His Thr Ala Gln Thr Gln Thr His Arg Glu Asp
305                 310                 315                 320

Tyr Asn Ser Thr Ile Arg Val Val Ser Thr Leu Pro Ile Gln His Gln
                325                 330                 335

Asp Trp Met Ser Gly Lys Glu Phe Lys Cys Lys Val Asn Asn Lys Asp
            340                 345                 350

Leu Pro Ser Pro Ile Glu Arg Thr Ile Ser Lys Ile Lys Gly Leu Val
        355                 360                 365

Arg Ala Pro Gln Val Tyr Ile Leu Pro Pro Ala Glu Gln Leu Ser
    370                 375                 380

Arg Lys Asp Val Ser Leu Thr Cys Leu Val Val Gly Phe Asn Pro Gly
385                 390                 395                 400

Asp Ile Ser Val Glu Trp Thr Ser Asn Gly His Thr Glu Glu Asn Tyr
                405                 410                 415

Lys Asp Thr Ala Pro Val Leu Asp Ser Asp Gly Ser Tyr Phe Ile Tyr
            420                 425                 430
```

```
Ser Lys Leu Asn Met Lys Thr Ser Lys Trp Glu Lys Thr Asp Ser Phe
        435                 440                 445

Ser Cys Asn Val Arg His Glu Gly Leu Lys Asn Tyr Tyr Leu Lys Lys
450                 455                 460

Thr Ile Ser Arg Ser Pro Gly Lys Arg Gly Lys Arg Arg Ser Gly
465                 470                 475                 480

Ser Gly Ala Thr Asn Phe Ser Leu Leu Lys Gln Ala Gly Asp Val Glu
            485                 490                 495

Glu Asn Pro Gly Pro Met Val Leu Gln Thr Gln Val Phe Ile Ser Leu
                500                 505                 510

Leu Leu Trp Ile Ser Gly Ala Tyr Gly Asp Ile Val Met Thr Gln Thr
        515                 520                 525

Thr Leu Ser Leu Pro Val Ser Leu Gly Asp Gln Ala Ser Ile Ser Cys
530                 535                 540

Arg Ser Ser Gln Ser Ile Val His Ser Asn Gly Asn Thr Tyr Leu Glu
545                 550                 555                 560

Trp Tyr Leu Gln Lys Pro Gly Gln Ser Pro Lys Leu Leu Ile Tyr Lys
                565                 570                 575

Val Ser Asn Arg Phe Ser Gly Val Pro Asp Arg Phe Ser Gly Ser Gly
            580                 585                 590

Ser Gly Thr Asp Phe Thr Leu Lys Ile Ser Arg Val Glu Ala Glu Asp
        595                 600                 605

Leu Gly Val Tyr Tyr Cys Phe Gln Gly Ser His Val Pro Tyr Thr Phe
        610                 615                 620

Gly Gly Gly Thr Lys Leu Glu Ile Lys Arg Ala Asp Ala Ala Pro Thr
625                 630                 635                 640

Val Ser Ile Phe Pro Pro Ser Ser Glu Gln Leu Thr Ser Gly Gly Ala
                645                 650                 655

Ser Val Val Cys Phe Leu Asn Asn Phe Tyr Pro Lys Asp Ile Asn Val
            660                 665                 670

Lys Trp Lys Ile Asp Gly Ser Glu Arg Gln Asn Gly Val Leu Asn Ser
        675                 680                 685

Trp Thr Asp Gln Asp Ser Lys Asp Ser Thr Tyr Ser Met Ser Ser Thr
690                 695                 700

Leu Thr Leu Thr Lys Asp Glu Tyr Glu Arg His Asn Ser Tyr Thr Cys
705                 710                 715                 720

Glu Ala Thr His Lys Thr Ser Thr Ser Pro Ile Val Lys Ser Phe Asn
                725                 730                 735

Arg Asn Glu Cys
            740

<210> SEQ ID NO 5
<211> LENGTH: 733
<212> TYPE: PRT
<213> ORGANISM: Artificial Sequence
<220> FEATURE:
<223> OTHER INFORMATION: Chemically synthesized, Tremelimumab DMAb

<400> SEQUENCE: 5

Met Asp Trp Thr Trp Arg Ile Leu Phe Leu Val Ala Ala Ala Thr Gly
1               5                   10                  15

Thr His Ala Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45
```

-continued

```
Ser Ser Tyr Gly Met His Trp Val Arg Gln Ala Pro Gly Lys Gly Leu
    50                  55                  60

Glu Trp Val Ala Val Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Pro Arg Gly Ala Thr Leu Tyr Tyr Tyr Tyr
        115                 120                 125

Tyr Gly Met Asp Val Trp Gly Gln Gly Thr Thr Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Gln Phe Asn Trp Tyr Val Asp Gly
    290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460
```

```
Ser Leu Ser Pro Gly Lys Arg Gly Arg Lys Arg Arg Ser Gly Ser Gly
465                 470                 475                 480

Ala Thr Asn Phe Ser Leu Leu Lys Gln Ala Gly Asp Val Glu Glu Asn
                485                 490                 495

Pro Gly Pro Met Val Leu Gln Thr Gln Val Phe Ile Ser Leu Leu Leu
            500                 505                 510

Trp Ile Ser Gly Ala Tyr Gly Asp Ile Gln Met Thr Gln Ser Pro Ser
        515                 520                 525

Ser Leu Ser Ala Ser Val Gly Asp Arg Val Thr Ile Thr Cys Arg Ala
530                 535                 540

Ser Gln Ser Ile Asn Ser Tyr Leu Asp Trp Tyr Gln Gln Lys Pro Gly
545                 550                 555                 560

Lys Ala Pro Lys Leu Leu Ile Tyr Ala Ala Ser Ser Leu Gln Ser Gly
                565                 570                 575

Val Pro Ser Arg Phe Ser Gly Ser Gly Ser Gly Thr Asp Phe Thr Leu
            580                 585                 590

Thr Ile Ser Ser Leu Gln Pro Glu Asp Phe Ala Thr Tyr Tyr Cys Gln
        595                 600                 605

Gln Tyr Tyr Ser Thr Pro Phe Thr Phe Gly Pro Gly Thr Lys Val Glu
610                 615                 620

Ile Lys Arg Thr Val Ala Ala Pro Ser Val Phe Ile Phe Pro Pro Ser
625                 630                 635                 640

Asp Glu Gln Leu Lys Ser Gly Thr Ala Ser Val Val Cys Leu Leu Asn
                645                 650                 655

Asn Phe Tyr Pro Arg Glu Ala Lys Val Gln Trp Lys Val Asp Asn Ala
            660                 665                 670

Leu Gln Ser Gly Asn Ser Gln Glu Ser Val Thr Glu Gln Asp Ser Lys
        675                 680                 685

Asp Ser Thr Tyr Ser Leu Ser Asn Thr Leu Thr Leu Ser Lys Ala Asp
690                 695                 700

Tyr Glu Lys His Lys Val Tyr Ala Cys Glu Val Thr His Gln Gly Leu
705                 710                 715                 720

Ser Ser Pro Val Thr Lys Ser Phe Asn Arg Gly Glu Cys
                725                 730

<210> SEQ ID NO 6
<211> LENGTH: 731
<212> TYPE: PRT
<213> ORGANISM: Artificial Sequence
<220> FEATURE:
<223> OTHER INFORMATION: Chemically synthesized, Ipilimumab DMAb

<400> SEQUENCE: 6

Met Asp Trp Thr Trp Arg Ile Leu Phe Leu Val Ala Ala Ala Thr Gly
1               5                   10                  15

Thr His Ala Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Ser Tyr Thr Met His Trp Val Arg Gln Ala Pro Gly Lys Gly Leu
        50                  55                  60

Glu Trp Val Thr Phe Ile Ser Tyr Asp Gly Asn Asn Lys Tyr Tyr Ala
65                  70                  75                  80

Asp Ser Val Lys Gly Arg Phe Thr Ile Ser Arg Asp Asn Ser Lys Asn
                85                  90                  95
```

```
Thr Leu Tyr Leu Gln Met Asn Ser Leu Arg Ala Glu Asp Thr Ala Ile
            100                 105                 110
Tyr Tyr Cys Ala Arg Thr Gly Trp Leu Gly Pro Phe Asp Tyr Trp Gly
        115                 120                 125
Gln Gly Thr Leu Val Thr Val Ser Ser Ala Ser Thr Lys Gly Pro Ser
130                 135                 140
Val Phe Pro Leu Ala Pro Ser Ser Lys Ser Thr Ser Gly Gly Thr Ala
145                 150                 155                 160
Ala Leu Gly Cys Leu Val Lys Asp Tyr Phe Pro Glu Pro Val Thr Val
                165                 170                 175
Ser Trp Asn Ser Gly Ala Leu Thr Ser Gly Val His Thr Phe Pro Ala
            180                 185                 190
Val Leu Gln Ser Ser Gly Leu Tyr Ser Leu Ser Ser Val Val Thr Val
        195                 200                 205
Pro Ser Ser Ser Leu Gly Thr Gln Thr Tyr Ile Cys Asn Val Asn His
    210                 215                 220
Lys Pro Ser Asn Thr Lys Val Asp Lys Lys Val Glu Pro Lys Ser Cys
225                 230                 235                 240
Asp Lys Thr His Thr Cys Pro Pro Cys Pro Ala Pro Glu Leu Leu Gly
                245                 250                 255
Gly Pro Ser Val Phe Leu Phe Pro Pro Lys Pro Lys Asp Thr Leu Met
            260                 265                 270
Ile Ser Arg Thr Pro Glu Val Thr Cys Val Val Val Asp Val Ser His
        275                 280                 285
Glu Asp Pro Glu Val Lys Phe Asn Trp Tyr Val Asp Gly Val Glu Val
    290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
            340                 345                 350
Glu Lys Thr Ile Ser Lys Ala Lys Gly Gln Pro Arg Glu Pro Gln Val
        355                 360                 365
Tyr Thr Leu Pro Pro Ser Arg Asp Glu Leu Thr Lys Asn Gln Val Ser
370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
    450                 455                 460
Pro Gly Lys Arg Gly Arg Lys Arg Arg Ser Gly Ser Gly Ala Thr Asn
465                 470                 475                 480
Phe Ser Leu Leu Lys Gln Ala Gly Asp Val Glu Glu Asn Pro Gly Pro
                485                 490                 495
Met Val Leu Gln Thr Gln Val Phe Ile Ser Leu Leu Leu Trp Ile Ser
            500                 505                 510
```

```
Gly Ala Tyr Gly Glu Ile Val Leu Thr Gln Ser Pro Gly Thr Leu Ser
            515                 520                 525
Leu Ser Pro Gly Glu Arg Ala Thr Leu Ser Cys Arg Ala Ser Gln Ser
        530                 535                 540
Val Gly Ser Ser Tyr Leu Ala Trp Tyr Gln Gln Lys Pro Gly Gln Ala
545                 550                 555                 560
Pro Arg Leu Leu Ile Tyr Gly Ala Phe Ser Arg Ala Thr Gly Ile Pro
                565                 570                 575
Asp Arg Phe Ser Gly Ser Gly Ser Gly Thr Asp Phe Thr Leu Thr Ile
            580                 585                 590
Ser Arg Leu Glu Pro Glu Asp Phe Ala Val Tyr Tyr Cys Gln Gln Tyr
        595                 600                 605
Gly Ser Ser Pro Trp Thr Phe Gly Gln Gly Thr Lys Val Glu Ile Lys
    610                 615                 620
Arg Thr Val Ala Ala Pro Ser Val Phe Ile Phe Pro Pro Ser Asp Glu
625                 630                 635                 640
Gln Leu Lys Ser Gly Thr Ala Ser Val Val Cys Leu Leu Asn Asn Phe
                645                 650                 655
Tyr Pro Arg Glu Ala Lys Val Gln Trp Lys Val Asp Asn Ala Leu Gln
            660                 665                 670
Ser Gly Asn Ser Gln Glu Ser Val Thr Glu Gln Asp Ser Lys Asp Ser
        675                 680                 685
Thr Tyr Ser Leu Ser Ser Thr Leu Thr Leu Ser Lys Ala Asp Tyr Glu
    690                 695                 700
Lys His Lys Val Tyr Ala Cys Glu Val Thr His Gln Gly Leu Ser Ser
705                 710                 715                 720
Pro Val Thr Lys Ser Phe Asn Arg Gly Glu Cys
                725                 730
```

<210> SEQ ID NO 7
<211> LENGTH: 2226
<212> TYPE: DNA
<213> ORGANISM: Artificial Sequence
<220> FEATURE:
<223> OTHER INFORMATION: Chemically synthesized, pGX93115 (9D9 dMAb
      original)

<400> SEQUENCE: 7

| | | |
|---|---|---|
| atggactgga cttggaggat tctgtttctg gtcgccgctg ccactggaac ccacgcagag | 60 |
| gcaaaactgc aggaatcagg ccccgtgctg gtgaagccag agccagcgt gaagatgtcc | 120 |
| tgcaaggctt ctggctacac cttcacagac tactacatga actgggtgaa gcagagccac | 180 |
| ggcaagtccc tggagtggat cggagtgatc aaccccctaca acggcgacac ctcctacaac | 240 |
| cagaagttta agggaaaggc caccctgaca gtggataaga gctcctctac cgcttacatg | 300 |
| gagctgaact ccctgacatc tgaggacagc gccgtgtact actgtgctcg gtactacggc | 360 |
| tcctggttcg cctactgggg acagggcaca ctgatcaccg tgtctaccgc taagaccaca | 420 |
| cccccagcg tgtacccact ggctcctgga tgcggcgata ccacaggcag ctccgtgacc | 480 |
| ctgggctgtc tggtgaaggg atacttccca gagtctgtga ccgtgacatg aacagcggc | 540 |
| agcctgagca gcagcgtgca cacctttccc gctctgctgc agagcggcct gtacacaatg | 600 |
| tctagctccg tgaccgtgcc ctctagcaca tggccttccc agaccgtgac atgctctgtg | 660 |
| gcccacccag cttcctctac cacagtggac aagaagctgg agccatctgg ccccatcagc | 720 |
| accatcaacc cctgccctcc atgcaaggag tgccacaagt gtcctgcccc aaacctggag | 780 |

```
ggcggacctt ccgtgttcat ctttccccct aacatcaagg atgtgctgat gatctctctg    840
acccctaagg tgacatgcgt ggtggtggac gtgagcgagg acgatccaga tgtgcagatc    900
tcctggttcg tgaacaacgt ggaggtgcac accgctcaga cccagacaca ccgggaggac    960
tacaacagca ccatccgcgt ggtgtccaca ctgcctatcc agcaccagga ctggatgagc   1020
ggaaaggagt ttaagtgcaa ggtgaacaac aaggatctgc cctcccctat cgagaggaca   1080
atctctaaga tcaagggcct ggtgagagcc ccacaggtgt acatcctgcc accccctgct   1140
gagcagctga gcaggaagga cgtgtccctg acctgtctgg tggtgggctt caaccctgga   1200
gatatctctg tggagtggac cagcaacgga cacacagagg agaactacaa ggacacagcc   1260
ccagtgctgg actccgatgg ctcttacttc atctacagca agctgaacat gaagacctcc   1320
aagtgggaga gacagattc tttagctgc aacgtgcggc acgagggcct gaagaactac   1380
tacctgaaga agaccatctc ccgctctccc ggcaagaggg aaggaagag gagaagcggc   1440
agcggcgcca caaacttctc cctgctgaag caggctggag acgtggagga aacccaggc   1500
cccatggtgc tgcagaccca ggtgtttatc tctctgctgc tgtggatcag cggcgcctac   1560
ggagacatcg tgatgacaca gaccacactg tccctgcccg tgagcctggg cgatcaggct   1620
tctatcagct gtagaagctc ccagagcatc gtgcactcca acggaaacac ctacctggag   1680
tggtacctgc agaagcctgg ccagagccca aagctgctga tctacaaggt gtctaacagg   1740
ttcagcggcg tgcccgacag attttccgga tctggcagcg gaaccgattt cacactgaag   1800
atcagcaggg tggaggccga ggatctggga gtgtactact gcttccaggg ctcccacgtg   1860
ccttacacct tggcggagg cacaaagctg gagatcaaga gctgacgc tgctccaaca   1920
gtgtctatct ttccacccctc tagcgagcag ctgacctccg gaggcgcctc tgtggtgtgc   1980
ttcctgaaca ctttttaccc caaggacatc aacgtgaagt ggaagatcga tggctctgag   2040
cggcagaacg gagtgctgaa cagctggacc gaccaggata gcaaggactc cacatactct   2100
atgtcctcta ccctgacact gaccaaggat gagtacgagc gccacaactc ctacacatgc   2160
gaggcaaccc ataaaacttc aaccagccca atcgtcaaat ccttcaacag aaatgagtgc   2220
tgataa                                                               2226
```

<210> SEQ ID NO 8
<211> LENGTH: 2226
<212> TYPE: DNA
<213> ORGANISM: Artificial Sequence
<220> FEATURE:
<223> OTHER INFORMATION: Chemically synthesized, pGX93116 (9D9 dMAb mod #2)

<400> SEQUENCE: 8

```
atggactgga cttggaggat tctgtttctg gtcgccgctg ccactggaac ccacgcagag     60
gcaaaactgc aggaatcagg ccccgtgctg gtgaagccag agccagcgt gaagatgtcc    120
tgcaaggctt ctggctacac cttcacagac tactacatga actgggtgaa gcagagccac    180
ggcaagtccc tggagtggat cggagtgatc aaccccctaca cggcgacac ctcctacaac    240
cagaagttta aggaaaggc caccctgaca gtggataaga gctcctctac cgcttacatg    300
gagctgaact ccctgacatc tgaggacagc gccgtgtact actgtgctcg gtactacggc    360
tcctggttcg cctactgggg acagggcaca ctggtgaccg tgtcttctgc taagaccaca    420
cccccagcg tgtacccact ggctcctgga tgcggcgata ccacaggcag ctccgtgacc    480
ctgggctgtc tggtgaaggg atacttccca gagtctgtga ccgtgacatg gaacagcggc    540
```

| | |
|---|---|
| agcctgagca gcagcgtgca cacctttccc gctctgctgc agagcggcct gtacacaatg | 600 |
| tctagctccg tgaccgtgcc ctctagcaca tggccttccc agaccgtgac atgtctgtg | 660 |
| gcccacccag cttcctctac cacagtggac aagaagctgg agccatctgg ccccatcagc | 720 |
| accatcaacc cctgccctcc atgcaaggag tgccacaagt gtcctgcccc aaacctggag | 780 |
| ggcggacctt ccgtgttcat ctttccccct aacatcaagg atgtgctgat gatctctctg | 840 |
| accccctaagg tgcatgcgt ggtggtggac gtgagcgagg acgatccaga tgtgcagatc | 900 |
| tcctggttcg tgaacaacgt ggaggtgcac accgctcaga cccagacaca ccgggaggac | 960 |
| tacaacagca ccatccgcgt ggtgtccaca ctgcctatcc agcaccagga ctggatgagc | 1020 |
| ggaaaggagt ttaagtgcaa ggtgaacaac aaggatctgc cctcccctat cgagaggaca | 1080 |
| atctctaaga tcaagggcct ggtgagagcc ccacaggtgt acatcctgcc acccctgct | 1140 |
| gagcagctga gcaggaagga cgtgtccctg acctgtctgg tggtgggctt caaccctgga | 1200 |
| gatatctctg tggagtggac cagcaacgga cacacagagg agaactacaa ggacacagcc | 1260 |
| ccagtgctgg actccgatgg ctcttacttc atctacagca agctgaacat gaagacctcc | 1320 |
| aagtgggaga gacagattc tttttagctgc aacgtgcggc acgagggcct gaagaactac | 1380 |
| tacctgaaga gaccatctc ccgctctccc ggcaagaggg gaaggaagag gagaagcggc | 1440 |
| agcggcgcca caaacttctc cctgctgaag caggctggag acgtggagga gaacccaggc | 1500 |
| cccatggtgc tgcagaccca ggtgtttatc tctctgctgc tgtggatcag cggcgcctac | 1560 |
| ggagacatcg tgatgacaca gaccacactg tccctgcccg tgagcctggg cgatcaggct | 1620 |
| tctatcagct gtagaagctc ccagagcatc gtgcactcca acggaaacac ctacctggag | 1680 |
| tggtacctgc agaagcctgg ccagagccca aagctgctga tctacaaggt gtctaacagg | 1740 |
| ttcagcggcg tgcccgacag atttttccgga tctggcagcg gaaccgattt cacactgaag | 1800 |
| atcagcaggg tggaggccga ggatctggga gtgtactact gcttccaggg ctcccacgtg | 1860 |
| ccttacacct ttggcggagg cacaaagctg gagatcaaga gctgacgc tgctccaaca | 1920 |
| gtgtctatct ttccacccctc tagcgagcag ctgacctccg gaggcgcctc tgtggtgtgc | 1980 |
| ttcctgaaca ctttttaccc caaggacatc aacgtgaagt ggaagatcga tggctctgag | 2040 |
| cggcagaacg gagtgctgaa cagctggacc gaccaggata gcaaggactc cacatactct | 2100 |
| atgtcctcta cccctgacact gaccaaggat gagtacgagc gccacaactc ctacacatgc | 2160 |
| gaggcaaccc ataaaacttc aaccagccca atcgtcaaat ccttcaacag aaatgagtgc | 2220 |
| tgataa | 2226 |

<210> SEQ ID NO 9
<211> LENGTH: 2226
<212> TYPE: DNA
<213> ORGANISM: Artificial Sequence
<220> FEATURE:
<223> OTHER INFORMATION: Chemically synthesized, pGX93117 (9D9 dMAb mod #3)

<400> SEQUENCE: 9

| | |
|---|---|
| atggactgga cttggaggat tctgtttctg gtcgccgctg ccactggaac ccacgcagag | 60 |
| gtgcagctgc agcaatcagg ccccgtgctg gtgaagccag agccagcgt gaagatgtcc | 120 |
| tgcaaggctt ctggctacac cttcacagac tactacatga actgggtgaa gcagagccac | 180 |
| ggcaagtccc tggagtggat cggagtgatc aaccccctaca cggcgacac ctcctacaac | 240 |
| cagaagttta gggaaaggc caccctgaca gtggataaga gctcctctac cgcttacatg | 300 |

```
gagctgaact ccctgacatc tgaggacagc gccgtgtact actgtgctcg gtactacggc      360
tcctggttcg cctactgggg acagggcaca ctgatcaccg tgtctaccgc taagaccaca      420 cccccagcg tgtacccact ggctcctgga tgcggcgata ccacaggcag ctccgtgacc      480
ctgggctgtc tggtgaaggg atacttccca gagtctgtga ccgtgacatg aacagcggc      540 agcctgagca gcagcgtgca ccctttcccc gctctgctgc agagcggcct gtacacaatg      600
tctagctccg tgaccgtgcc ctctagcaca tggccttccc agaccgtgac atgctctgtg      660
gcccacccag cttcctctac cacagtggac aagaagctgg agccatctgg ccccatcagc      720
accatcaacc cctgccctcc atgcaaggag tgccacaagt gtcctgcccc aaacctggag      780
ggcggacctt ccgtgttcat cttcccccct aacatcaagg atgtgctgat gatctctctg      840 accctaagg tgacatgcgt ggtggtggac gtgagcgagg acgatccaga tgtgcagatc      900
tcctggttcg tgaacaacgt ggaggtgcac accgctcaga cccagacaca ccgggaggac      960
tacaacagca ccatccgcgt ggtgtccaca ctgcctatcc agcaccagga ctggatgagc      1020
ggaaaggagt ttaagtgcaa ggtgaacaac aaggatctgc cctcccctat cgagaggaca      1080
atctctaaga tcaagggcct ggtgagagcc ccacaggtgt acatcctgcc acccctgct      1140 gagcagctga gcaggaagga cgtgtccctg acctgtctgg tggtgggctt caaccctgga      1200
gatatctctg tggagtggac cagcaacgga cacacagagg agaactacaa ggacacagcc      1260
ccagtgctgg actccgatgg ctcttacttc atctacagca agctgaacat gaagacctcc      1320
aagtgggaga gacagattc tttagctgc aacgtgcggc acgagggcct gaagaactac      1380
tacctgaaga agaccatctc ccgctctccc ggcaagaggg aaggaagag gagaagcggc      1440 agcggcgcca caaacttctc cctgctgaag caggctggag acgtggagga aacccaggc      1500 cccatggtgc tgcagaccca ggtgtttatc tctctgctgc tgtggatcag cggcgcctac      1560
ggagacatcg tgatgacaca gaccacactg tccctgcccg tgagcctggg cgatcaggct      1620
tctatcagct gtagaagctc ccagagcatc gtgcactcca acggaaacac ctacctggag      1680
tggtacctgc agaagcctgg ccagagccca aagctgctga tctacaaggt gtctaacagg      1740
ttcagcggcg tgcccgacag attttccgga tctggcagcg gaaccgattt cacactgaag      1800
atcagcaggt ggaggccga ggatctggga gtgtactact gcttccaggg ctcccacgtg      1860
ccttacacct ttggcggagg cacaaagctg gagatcaaga gctgacgc tgctccaaca      1920 gtgtctatct ttccacccct agcgagcag ctgacctccg gaggcgcctc tgtggtgtgc      1980
ttcctgaaca cttttaccc caaggacatc aacgtgaagt ggaagatcga tggctctgag      2040
cggcagaacg gagtgctgaa cagctggacc gaccaggata gcaaggactc cacatactct      2100
atgtcctcta ccctgacact gaccaaggat gagtacgagc gccacaactc ctacacatgc      2160
gaggcaaccc ataaaacttc aaccagccca atcgtcaaat ccttcaacag aaatgagtgc      2220
tgataa                                                                2226
```

<210> SEQ ID NO 10
<211> LENGTH: 2226
<212> TYPE: DNA
<213> ORGANISM: Artificial Sequence
<220> FEATURE:
<223> OTHER INFORMATION: Chemically synthesized, pGX93118 (9D9 dMAb mod #4)

<400> SEQUENCE: 10

```
atggactgga cttggaggat tctgtttctg gtcgccgctg ccactggaac ccacgcagag      60
gtgcagctgc agcaatcagg ccccgtgctg gtgaagccag agccagcgt gaagatgtcc     120
tgcaaggctt ctggctacac cttcacagac tactacatga actgggtgaa gcagagccac    180
ggcaagtccc tggagtggat cggagtgatc aaccccctaca acggcgacac ctcctacaac   240
cagaagttta agggaaaggc caccctgaca gtggataaga gctcctctac cgcttacatg    300
gagctgaact ccctgacatc tgaggacagc gccgtgtact actgtgctcg gtactacggc    360
tcctggttcg cctactgggg acagggcaca ctggtgaccg tgtcttctgc taagaccaca    420
ccccccagcg tgtacccact ggctcctgga tgcggcgata ccacaggcag ctccgtgacc    480
ctgggctgtc tggtgaaggg atacttccca gagtctgtga ccgtgacatg gaacagcggc    540
agcctgagca gcagcgtgca cacctttccc gctctgctgc agagcggcct gtacacaatg    600
tctagctccg tgaccgtgcc ctctagcaca tggccttccc agaccgtgac atgctctgtg    660
gcccacccag cttcctctac cacagtggac aagaagctgg agccatctgg ccccatcagc    720
accatcaacc cctgccctcc atgcaaggag tgccacaagt gtcctgcccc aaacctggag    780
ggcggacctt ccgtgttcat cttcccccct aacatcaagg atgtgctgat gatctctctg    840
acccctaagg tgacatgcgt ggtggtggac gtgagcgagg acgatccaga tgtgcagatc    900
tcctggttcg tgaacaacgt ggaggtgcac accgctcaga cccagacaca ccgggaggac    960
tacaacagca ccatccgcgt ggtgtccaca ctgcctatcc agcaccagga ctggatgagc   1020
ggaaaggagt ttaagtgcaa ggtgaacaac aaggatctgc cctcccctat cgagaggaca   1080
atctctaaga tcaagggcct ggtgagagcc ccacaggtgt acatcctgcc accccctgct   1140
gagcagctga gcaggaagga cgtgtccctg acctgtctgg tggtgggctt caaccctgga   1200
gatatctctg tggagtggac cagcaacgga cacacagagg agaactacaa ggacacagcc   1260
ccagtgctgg actccgatgg ctcttacttc atctacagca agctgaacat gaagacctcc   1320
aagtgggaga gacagattc ttttagctgc aacgtgcggc acgagggcct gaagaactac   1380
tacctgaaga agaccatctc ccgctctccc ggcaagaggg gaaggaagag gagaagcggc   1440
agcggcgcca caaacttctc cctgctgaag caggctggag acgtggagga gaacccaggc   1500
cccatggtgc tgcagaccca ggtgtttatc tctctgctgc tgtggatcag cggcgcctac   1560
ggagacatcg tgatgacaca gaccacactg tccctgcccg tgagcctggg cgatcaggct   1620
tctatcagct gtagaagctc ccagagcatc gtgcactcca acggaaacac ctacctggag   1680
tggtacctgc agaagcctgg ccagagccca agctgctga tctacaaggt gtctaacagg   1740
ttcagcggcg tgcccgacag attttccgga tctggcagcg gaaccgattt cacactgaag   1800
atcagcaggg tggaggccga ggatctggga gtgtactact gcttccaggg ctcccacgtg   1860
ccttacacct ttggcggagg cacaaagctg gagatcaaga gctgacgc tgctccaaca    1920
gtgtctatct ttccaccctc tagcgagcag ctgacctccg gaggcgcctc tgtggtgtgc   1980
ttcctgaaca cttttaccc caaggacatc aacgtgaagt ggaagatcga tggctctgag   2040
cggcagaacg gagtgctgaa cagctggacc gaccaggata gcaaggactc cacatactct   2100
atgtcctcta ccctgacact gaccaaggat gagtacgagc gccacaactc ctacacatgc   2160
gaggcaaccc ataaaacttc aaccagccca atcgtcaaat ccttcaacag aaatgagtgc   2220
tgataa                                                               2226
```

<210> SEQ ID NO 11
<211> LENGTH: 2199
<212> TYPE: DNA
<213> ORGANISM: Artificial Sequence
<220> FEATURE:
<223> OTHER INFORMATION: Chemically synthesized, pGX93139 (Ipilimumab)

<400> SEQUENCE: 11

| | | | | | |
|---|---|---|---|---|---|
| atggactgga | cctggagaat | cctgttcctg | gtggcagcag | caaccggaac | acacgcacag | 60 |
| gtgcagctgg | tggagagcgg | cggcggcgtg | gtgcagcctg | gcaggagcct | gagactgagc | 120 |
| tgcgcagcat | ccggcttcac | ctttagctcc | tacacaatgc | actgggtgag | acaggcacca | 180 |
| ggcaagggcc | tggagtgggt | gaccttcatc | tcttatgacg | gcaacaataa | gtactatgcc | 240 |
| gatagcgtga | agggccggtt | taccatctct | cgcgacaaca | gcaagaatac | actgtacctg | 300 |
| cagatgaact | ccctgcgggc | cgaggacacc | gccatctact | attgcgcaag | gacaggatgg | 360 |
| ctgggaccat | tcgattattg | gggccagggc | accctggtga | cagtgtctag | cgccagcaca | 420 |
| aagggaccat | ccgtgtttcc | actggcacct | cctctaaga | gcacctccgg | cggcacagcc | 480 |
| gccctgggct | gtctggtgaa | ggattacttc | cctgagccag | tgaccgtgtc | ctggaactct | 540 |
| ggcgccctga | ccagcggagt | gcacacattt | ccagccgtgc | tgcagagctc | cggcctgtac | 600 |
| tccctgtcta | gcgtggtgac | cgtgccttcc | tctagcctgg | gcacccagac | atatatctgc | 660 |
| aacgtgaatc | acaagccttc | caatacaaag | gtggacaaga | aggtggagcc | aaagtcttgt | 720 |
| gataagaccc | acacatgccc | tccctgtcca | gcacctgagc | tgctgggcgg | cccaagcgtg | 780 |
| ttcctgtttc | cacccaagcc | caaggacaca | ctgatgatca | gccggacccc | agaggtgaca | 840 |
| tgcgtggtgg | tggacgtgtc | ccacgaggac | cccgaggtga | agttcaactg | gtacgtggat | 900 |
| ggcgtggagg | tgcacaatgc | caagaccaag | cctaggggagg | agcagtacaa | ttctacctat | 960 |
| agagtggtga | gcgtgctgac | agtgctgcac | caggactggc | tgaacggcaa | ggagtataag | 1020 |
| tgcaaggtgt | ctaataaggc | cctgccagcc | cccatcgaga | agaccatcag | caaggcaaag | 1080 |
| ggacagccaa | gggagccaca | ggtgtacaca | ctgcctccaa | gcagagacga | gctgaccaag | 1140 |
| aaccaggtgt | ccctgacatg | tctggtgaag | ggcttctatc | cctccgatat | cgccgtggag | 1200 |
| tgggagtcta | atggccagcc | tgagaacaat | tacaagacca | ccccctgt | gctggacagc | 1260 |
| gatggctcct | ctttctgta | tagcaagctg | accgtggaca | agtccaggtg | gcagcaggggc | 1320 |
| aacgtgtttt | cttgcagcgt | gatgcacgag | gccctgcaca | atcactacac | ccagaagtcc | 1380 |
| ctgtctctga | gcccaggcaa | gagggggaagg | aagaggagat | ccggctctgg | cgccacaaac | 1440 |
| ttcagcctgc | tgaagcaggc | cggcgatgtg | gaggagaatc | ctggcccaat | ggtgctgcag | 1500 |
| acccaggtgt | ttatctccct | gctgctgtgg | atctctggcg | cctacggaga | gatcgtgctg | 1560 |
| acccagtccc | caggcacact | gagcctgtcc | cctggagaga | gggccaccct | gtcttgtaga | 1620 |
| gcctctcaga | gcgtgggctc | ctcttacctg | gcctggtatc | agcagaagcc | tggccaggcc | 1680 |
| ccaagactgc | tgatctacgg | agccttcagc | cgggccaccg | gcatccccga | ccgcttctcc | 1740 |
| ggctctggca | gcggcacaga | cttcaccctg | acaatctccc | ggctggagcc | tgaggacttc | 1800 |
| gccgtgtact | attgccagca | gtatggcagc | tccccatgga | cctttggcca | gggcacaaag | 1860 |
| gtggagatca | agaggaccgt | ggcagcacca | agcgtgttca | tctttccacc | cagcgacgag | 1920 |
| cagctgaagt | ccggcacagc | ctctgtggtg | tgcctgctga | acaatttcta | ccctcgggag | 1980 |
| gccaaggtgc | agtggaaggt | ggataacgcc | ctgcagtctg | gcaatagcca | ggagtccgtg | 2040 |
| accgagcagg | actctaagga | tagcacatat | tccctgtcta | gcaccctgac | actgagcaag | 2100 |

```
gccgattacg agaagcacaa ggtgtatgca tgcgaggtga cccaccaggg cctgtcctct    2160
cccgtgacaa agtcctttaa ccgcggcgag tgttgataa                           2199

<210> SEQ ID NO 12
<211> LENGTH: 2205
<212> TYPE: DNA
<213> ORGANISM: Artificial Sequence
<220> FEATURE:
<223> OTHER INFORMATION: Chemically synthesized, pGX93140 (Tremelimumab)

<400> SEQUENCE: 12
atggactgga cctggagaat cctgttcctg gtggcagcag caaccggaac acacgcacag      60
gtgcagctgg tggagagcgg cggcggcgtg gtgcagccag caggagcct gagactgagc     120 tgcgcagcat ccggcttcac ctttagctcc tatggaatgc actgggtgag gcaggcacca    180
ggcaagggcc tggagtgggt ggccgtgatc tggtacgacg gctctaacaa gtactatgcc    240
gatagcgtga agggcaggtt cacaatctct agagacaaca gcaagaatac cctgtacctg    300
cagatgaatt ccctgagagc cgaggacaca gccgtgtact attgtgccag ggaccccagg    360
ggcgccaccc tgtactatta ctattacgga atggacgtgt ggggccaggg aaccacagtg    420
acagtgtcta gcgcctctac caagggccct agcgtgtttc ccctggcccc ttgcagcaga    480
tccacatctg agagcaccgc cgccctggga tgtctggtga aggactactt ccccgagcct    540
gtgacagtgt cttggaacag cggcgccctg acatccggag tgcacacctt cctgccgtg    600 ctgcagtcct ctggcctgta ttctctgagc tccgtggtga ccgtgccatc tagcaatttc    660
ggcacccaga catacacctg caacgtggac cacaagccca gcaatacaaa ggtggataag    720
accgtggaga ggaagtgctg cgtggagtgc cctccctgtc cagccccacc cgtggcagga    780
ccatccgtgt tcctgtttcc tccaaagcct aaggacacac tgatgatcag cagaacacca    840
gaggtgacct gctggtggt ggacgtgtcc cacgaggacc ccgaggtgca gtttaactgg    900
tacgtggatg gcgtggaggt gcacaatgcc aagaccaagc caagggagga gcagttcaac    960
agcaccttca gggtggtgtc tgtgctgacc gtggtgcacc aggattggct gaacggcaag   1020
gagtacaagt gcaaggtgtc taataagggc ctgccagccc ccatcgagaa gacaatcagc   1080
aagaccaagg gacagccacg ggagccacag gtgtataccc tgcccccttc ccgcgaggag   1140
atgacaaaga accaggtgtc tctgacctgt ctggtgaagg gcttctaccc ctctgacatc   1200
gccgtggagt gggagagcaa tggccagcct gagaacaatt ataagaccac cacccatg    1260 ctggactccg atggctcttt cttctctgta ctccaagctga ccgtggataa gtctcggtgg   1320
cagcagggca acgtgttttc ctgctctgtg atgcacgagg ccctgcacaa tcactacaca   1380
cagaagagcc tgtccctgtc tccaggcaag aggggaagga agaggagaag cggctccgga   1440
gcaaccaact tcagcctgct gaagcaggca ggcgacgtgg aggagaatcc tggaccaatg   1500
gtgctgcaga cacaggtgtt tatcagcctg ctgctgtgga tctccggcgc ctatggcgac   1560
atccagatga cccagagccc ctcctctctg tctgccagcg tgggcgatcg ggtgacaatc   1620
acctgtcgcg cctcccagtc tatcaactcc tatctggatt ggtaccagca gaagcctggc   1680
aaggccccaa agctgctgat ctacgcagcc agctccctgc agtccggagt gccctctcgc   1740
ttcagcggct ccggctctgg cacagacttt acactgacca tctctagcct gcagcctgag   1800
gatttcgcca cctattactg ccagcagtat acagcacac ccttcacctt tggccctggc   1860
acaaaggtgg agatcaagag gaccgtggca gcacctagcg tgttcatctt tcctccatcc   1920
```

-continued

```
gacgagcagc tgaagagcgg aaccgcatcc gtggtgtgcc tgctgaacaa cttctaccca    1980
cgcgaggcca aggtgcagtg gaaggtggat aacgccctgc agagcggcaa ttcccaggag    2040
tctgtgacag agcaggacag caaggattcc acctacagcc tgtccaacac actgaccctg    2100
agcaaggccg actatgagaa gcacaaggtg tacgccctgc aggtgacaca ccagggcctg    2160
tcctctcccg tgaccaagtc cttcaatcgg ggcgagtgtt gataa                   2205
```

<210> SEQ ID NO 13
<211> LENGTH: 6
<212> TYPE: PRT
<213> ORGANISM: Artificial Sequence
<220> FEATURE:
<223> OTHER INFORMATION: Chemically Synthesized, unmodified N terminus
      sequence

<400> SEQUENCE: 13

Glu Ala Lys Leu Gln Glu
1               5

<210> SEQ ID NO 14
<211> LENGTH: 5
<212> TYPE: PRT
<213> ORGANISM: Artificial Sequence
<220> FEATURE:
<223> OTHER INFORMATION: Chemically Synthesized, unmodified C terminus
      sequence

<400> SEQUENCE: 14

Ile Thr Val Ser Thr
1               5

<210> SEQ ID NO 15
<211> LENGTH: 6
<212> TYPE: PRT
<213> ORGANISM: Artificial Sequence
<220> FEATURE:
<223> OTHER INFORMATION: Chemically Synthesized, modified C terminus
      sequence

<400> SEQUENCE: 15

Glu Val Gln Leu Gln Gln
1               5

<210> SEQ ID NO 16
<211> LENGTH: 5
<212> TYPE: PRT
<213> ORGANISM: Artificial Sequence
<220> FEATURE:
<223> OTHER INFORMATION: Chemically Synthesized, modified N terminus
      sequence

<400> SEQUENCE: 16

Val Thr Val Ser Ser
1               5

<210> SEQ ID NO 17
<211> LENGTH: 7
<212> TYPE: PRT
<213> ORGANISM: Artificial Sequence
<220> FEATURE:
<223> OTHER INFORMATION: Chemically synthesized, furin cleavage sequence

<400> SEQUENCE: 17

Arg Gly Arg Lys Arg Arg Ser
1               5